United States Patent
Ibrahim et al.

(10) Patent No.: US 10,584,122 B2
(45) Date of Patent: Mar. 10, 2020

(54) SOLID FORMS OF A COMPOUND MODULATING KINASES

(71) Applicant: Plexxikon Inc., Berkeley, CA (US)

(72) Inventors: Prabha N. Ibrahim, Mountain View, CA (US); Gary Conard Visor, Castro Valley, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days.

(21) Appl. No.: 16/219,730

(22) Filed: Dec. 13, 2018

(65) Prior Publication Data

US 2019/0119273 A1    Apr. 25, 2019

Related U.S. Application Data

(60) Continuation of application No. 15/725,197, filed on Oct. 4, 2017, now Pat. No. 10,189,833, which is a
(Continued)

(51) Int. Cl.
*C07D 471/04* (2006.01)
*A61K 31/437* (2006.01)
(Continued)

(52) U.S. Cl.
CPC .......... *C07D 471/04* (2013.01); *A61K 31/337* (2013.01); *A61K 31/352* (2013.01);
(Continued)

(58) Field of Classification Search
CPC .............. C07D 471/04; A61K 31/4188; A61K 31/444; A61K 31/437; C07B 2200/13
See application file for complete search history.

(56) References Cited

U.S. PATENT DOCUMENTS 7,202,266 B2    4/2007 Arnold et al.
7,348,338 B2    3/2008 Arnold et al.
(Continued)

FOREIGN PATENT DOCUMENTS

WO    WO-2008/063888    5/2008

OTHER PUBLICATIONS

Asai et al., "Depletion of microglia and inhibition of exosome synthesis halt tau propagation", Nature Neuroscience, 2015, vol. 18, No. 11, pp. 1584-1593.
(Continued)

*Primary Examiner* — Angela C Brown-Pettigrew
(74) *Attorney, Agent, or Firm* — Sheppard Mullin Richter & Hampton LLP

(57) ABSTRACT

Solid forms of the compound, [5-(5-chloro-1H-pyrrolo[2,3-b]pyridin-3-ylmethyl)-pyridin-2-yl]-(6-trifluoromethyl-pyridin-3-ylmethyl)-amine HCl salt (Compound I) and its free base, active on the receptor protein kinases c-Kit and/or c-Fms and/or Flt3, were prepared and characterized:

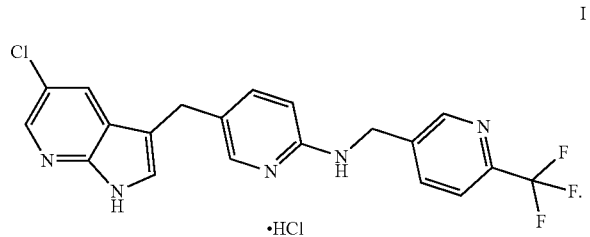

Also provided are methods of using the solid forms.

4 Claims, 23 Drawing Sheets

Related U.S. Application Data division of application No. 15/147,692, filed on May 5, 2016, now Pat. No. 9,802,932.

(60) Provisional application No. 62/157,902, filed on May 6, 2015.

(51) Int. Cl.
*A61K 31/337* (2006.01)
*A61K 31/352* (2006.01)
*A61K 31/4188* (2006.01)
*A61K 31/436* (2006.01)
*A61K 31/444* (2006.01)
*A61K 45/06* (2006.01)

(52) U.S. Cl.
CPC ........ *A61K 31/4188* (2013.01); *A61K 31/436* (2013.01); *A61K 31/437* (2013.01); *A61K 31/444* (2013.01); *A61K 45/06* (2013.01)

(56) References Cited

U.S. PATENT DOCUMENTS

| | | | |
|---|---|---|---|
| 7,476,746 B2 | 1/2009 | Artis et al. |
| 7,491,831 B2 | 2/2009 | Artis et al. |
| 7,504,509 B2 | 3/2009 | Ibrahim et al. |
| 7,517,970 B2 | 4/2009 | West |
| 7,572,806 B2 | 8/2009 | Arnold et al. |
| 7,585,859 B2 | 9/2009 | Ibrahim et al. |
| 7,605,168 B2 | 10/2009 | Ibrahim et al. |
| 7,723,374 B2 | 5/2010 | Artis et al. |
| 7,759,475 B2 | 7/2010 | West |
| 7,846,941 B2 | 12/2010 | Zhang et al. |
| 7,863,288 B2 | 1/2011 | Ibrahim et al. |
| 7,893,075 B2 | 2/2011 | Zhang et al. |
| 8,067,434 B2 | 11/2011 | Ibrahim et al. |
| 8,110,576 B2 | 2/2012 | Ibrahim et al. |
| 8,119,637 B2 | 2/2012 | Ibrahim et al. |
| 8,143,271 B2 | 3/2012 | Ibrahim et al. |
| 8,153,641 B2 | 4/2012 | Ibrahim et al. |
| 8,158,636 B2 | 4/2012 | Ibrahim et al. |
| 8,268,858 B2 | 9/2012 | Wu et al. |
| 8,367,828 B2 | 2/2013 | Arnold et al. |
| 8,404,700 B2 | 3/2013 | Ibrahim et al. |
| 8,415,469 B2 | 4/2013 | Ibrahim et al. |
| 8,461,169 B2 | 6/2013 | Zhang et al. |
| 8,470,818 B2 | 6/2013 | Ibrahim et al. |
| 8,470,821 B2 | 6/2013 | Ibrahim et al. |
| 8,642,606 B2 | 2/2014 | Ibrahim et al. |
| 8,673,928 B2 | 3/2014 | Ibrahim et al. |
| 8,722,702 B2 | 5/2014 | Zhang et al. |
| 8,865,735 B2 | 10/2014 | Ibrahim et al. |
| 8,901,118 B2 | 12/2014 | Zhang et al. |
| 8,901,301 B2 | 12/2014 | Ibrahim et al. |
| 8,912,204 B2 | 12/2014 | Ibrahim et al. |
| 9,096,593 B2 | 8/2015 | Zhang et al. |
| 9,150,570 B2 | 10/2015 | Ibrahim |
| 9,169,250 B2 | 10/2015 | Zhang et al. |
| 9,260,437 B2 | 2/2016 | Ibrahim et al. |
| 9,358,235 B2 | 6/2016 | Bollag et al. |
| 9,440,969 B2 | 9/2016 | Ibrahim et al. |
| 9,447,089 B2 | 9/2016 | Desai et al. |
| 9,469,640 B2 | 10/2016 | Wu et al. |
| 9,487,515 B2 | 11/2016 | Zhang et al. |
| 9,550,768 B2 | 1/2017 | Zhang et al. |
| 9,617,267 B2 | 4/2017 | Ibrahim et al. |
| 9,624,213 B2 | 4/2017 | Ibrahim et al. |
| 9,663,517 B2 | 5/2017 | Desai et al. |
| 9,676,748 B2 | 6/2017 | Wu et al. |
| 9,682,981 B2 | 6/2017 | Zhang et al. |
| 9,695,169 B2 | 7/2017 | Ibrahim |
| 9,718,847 B2 | 8/2017 | Zhang et al. |
| 9,730,918 B2 | 8/2017 | Bollag et al. |
| 9,745,298 B2 | 8/2017 | Ibrahim et al. |
| 9,771,363 B2 | 9/2017 | Ibrahim et al. |
| 9,771,369 B2 | 9/2017 | Lin et al. |
| 9,776,998 B2 | 10/2017 | Ibrahim et al. |
| 9,814,714 B2 | 11/2017 | Ibrahim et al. |
| 9,822,109 B2 | 11/2017 | Zhang et al. |
| 9,844,539 B2 | 12/2017 | Wu et al. |
| 9,856,259 B2 | 1/2018 | Shi et al. |
| 9,873,700 B2 | 1/2018 | Zhang et al. |
| 9,994,567 B2 | 6/2018 | Ibrahim et al. |
| 2014/0128390 A1 | 5/2014 | Lin et al. |
| 2016/0326162 A1 | 11/2016 | Lin et al. |
| 2016/0340357 A1 | 11/2016 | Ibrahim et al. |
| 2017/0029413 A1 | 2/2017 | Holladay et al. |
| 2017/0157120 A1 | 6/2017 | Ibrahim et al. |
| 2017/0158690 A1 | 6/2017 | Wu et al. |
| 2017/0247370 A1 | 8/2017 | Zhang et al. |
| 2017/0267660 A1 | 9/2017 | Lin et al. |
| 2017/0283423 A1 | 10/2017 | Zhang et al. |
| 2017/0319559 A1 | 11/2017 | Wu et al. |
| 2017/0320899 A1 | 11/2017 | Zhang et al. |
| 2017/0334909 A1 | 11/2017 | Ibrahim et al. |
| 2017/0349572 A1 | 12/2017 | Wu et al. |
| 2017/0362231 A1 | 12/2017 | Ibrahim et al. |
| 2018/0030051 A1 | 2/2018 | Ibrahim et al. |
| 2018/0055828 A1 | 3/2018 | Bollag et al. |
| 2018/0072722 A1 | 3/2018 | Zhang et al. |
| 2018/0099939 A1 | 4/2018 | Zhang et al. |
| 2018/0099975 A1 | 4/2018 | Zhang et al. |
| 2018/0111929 A1 | 4/2018 | Ibrahim et al. |
| 2018/0111930 A1 | 4/2018 | Desai et al. |
| 2018/0215763 A1 | 8/2018 | Wu et al. |
| 2018/0265508 A1 | 9/2018 | Lin et al. |
| 2018/0327403 A1 | 11/2018 | Ibrahim et al. |

OTHER PUBLICATIONS

Bosch et al., "Neuroinflammatory paradigms in lysosomal storage diseases", Frontiers in Neuroscience, 2015, vol. 9, Article 417. (11 pages).

Cheng et al., "High expression of FLT3 is a risk factor in leukemia", Molecular Medicine Reports, 2018, 17, pp. 2885-2892.

Cioce et al., "Autocrine CSF-1R signaling drives mesothelioma chemoresistance via AKT activation", Cell Death and Disease, 2014, 5, p. e1167.

Escamilla et al., "CSF1 Receptor Targeting in Prostate Cancer Reverses Macrophage-Mediated Resistance to Androgen Blockade Therapy", Cancer Res, 2015, 75(6), pp. 950-962.

Han et al., "An updated assessment of microglia depletion: current concepts and future directions", Molecular Brain, 2017, 10:25. (8 pages).

He et al., "c-Fms Signaling Mediates Neurofibromatosis Type-1 Osteoclast Gain-in-Functions", PLOS ONE, 2012, vol. 7, Issue 11, p. e46900.

Huang et al., "The possible mechanisms of tumor progression via CSF-1/CSF-1R pathway activation", Rom J Morphol Embryol, 2014, 55(2 Suppl), pp. 501-506.

International Preliminary Report on Patentability for International Application No. PCT/US2016/031027 dated Nov. 7, 2017. (6 pages).

International Search Report and Written Opinion for International Application No. PCT/US2016/031027 dated Aug. 3, 2016, 11 pages.

Jia et al., "High Expression of Macrophage Colony-Stimulating Factor-1 Receptor in Peritumoral Liver Tissue Is Associated with Poor Outcome in Hepatocellular Carcinoma After Curative Resection", The Oncologist, 2010, 15. (13 pages).

Kacinski et al., "High level expression of fms proto-oncogene mRNA is observed in clinically aggressive human endometrial adenocarcinomas", International Journal of Radiation Oncology*Biology*Physics, 1988, vol. 15, Issue 4, pp. 823-829. Abstract.

Kamenz et al., "Expression of c-kit receptor in human cholangiocarcinoma and in vivo treatment with imatinib mesilate in chimeric mice", World J Gastroenterol, 2006, 12(10), pp. 1583-1590.

(56) References Cited

OTHER PUBLICATIONS

Knight et al., "Increased Microglial CSF1R Expression in the SIV/Macaque Model of HIV CNS Disease", Journal of Neuropathology & Experimental Neurology, vol. 77, Issue 3, 2018, pp. 199-206. Abstract.
Li et al., "Colony stimulating factor I receptor inhibition eliminates microglia and attenuates brain injury after intracerebral hemorrhage", Journal of Cerebral Blood Flow & Metabolism, 2017, 37(7), pp. 2383-2395.
Littlejohn, G., "Neurogenic neuroinflammation in fibromyalgia and complex regional pain syndrome." Nat Rev Rheumatol, 2015, 11(11), pp. 639-648. Abstract.
Mallard et al., "Astrocytes and microglia in acute cerebral injury underlying cerebral palsy associated with preterm birth", Pediatric Research, 2014, vol. 75, No. 1, pp. 234-240.
McCarron et al., Plexiform neurofibroma with and without associated malignant peripheral nerve sheath tumor: a clinicopathologic and immunohistochemical analysis of 54 cases. Mod Pathol. 1998, 11(7), pp. 612-617. Abstract.
Melao, A., "#MSParis2017—Inhibiting Protein in Brain Cells Can Rejuvenate Protective Nerve Cell Coating, Study Shows", Multiple Sclerosis News Today, 2017. (2 pages).
Menke et al., "Autocrine CSF-1 and CSF-1 Receptor Coexpression Promotes Renal Cell Carcinoma Growth", Cancer Res, 2011, 72(1), pp. 1-14.
Morandi et al., "The Colony-Stimulating Factor-1 (CSF-1) Receptor Sustains ERK1/2 Activation and Proliferation in Breast Cancer Cell Lines", PLoS ONE, 2011, vol. 6, Issue 11, p. e27450.
Moskowitz et al., "CSF1R Inhibition by PLX3397 in Patients with Relapsed or Refractory Hodgkin Lymphoma: Results From a Phase 2 Single Agent Clinical Trial", Blood, 2012, 120, p. 1638. Abstract.
Mughal et al (Biologics: Targets & Therapy 2010:4, 315-323 (Year: 2010).
Olmos-Alonso et al., "Pharmacological targeting of CSF1R inhibits microglial proliferation and prevents the progression of Alzheimer's-like pathology", Brain, 2016, 139, pp. 891-907.
Passamonti et al., "[11C]PK11195 PET in Alzheimer's disease and progressive supranuclear palsy: The NIMROD Study", 2017. (1 page).
Patwardhan et al., "Sustained inhibition of receptor tyrosine kinases and macrophage depletion by PLX3397 and rapamycin as a potential new approach for the treatment of MPNSTs", Clin Cancer Res., 2014, 20(12), pp. 3146-3158.
Pyonteck et al., "CSF-1R inhibition alters macrophage polarization and blocks glioma progression", Nat Med., 2013, 19(10), pp. 1264-1272.
Ries et al., "Targeting Tumor-Associated Macrophages with Anti-CSF-1R Antibody Reveals a Strategy for Cancer Therapy", Cancer Cell, 2014, 25, pp. 846-859.
Salehinejad J. et al., "Evaluation of c-kit protein (CD117) expression in common salivary gland neoplasms." J Oral Maxillofac Pathol, 2014, 18(2), pp. 177-182. Abstract.
Siehl, J. et al., "C-kit, GIST, and imatinib." Recent Results Cancer Res., 2007, 176, pp. 145-151. Abstract.
Sluijter et al., "Inhibition of CSF-1R Supports T-Cell Mediated Melanoma Therapy", PLOS ONE, 2014, vol. 9, Issue 8, p. e104230.
Spangenberg et al., "Eliminating microglia in Alzheimer's mice prevents neuronal loss without modulating amyloid-β pathology", Brain, 2016, 139, pp. 1265-1281.
Srivastava et al., "A systems-level framework for drug discovery identifies CSF1R as a novel anti-epileptic drug target", bioRxiv preprint first posted online May 22, 2017.
Stefaniak et al., "Imaging of neuroinflammation in dementia: a review." J Neurol Neurosurg Psychiatry, 2016, 87(1), pp. 21-28. Abstract.
Tap, W.D., "Phase I Data Suggest PLX3397 Is a Potential Therapy for Patients with Advanced Pigmented Villonodular Synovitis", Pressroom/Press Releases, Memorial Sloan Kettering Cancer Center, 2014. (3 pages).
Terada et al., "Esophageal combined carcinomas: Immunohoistochemical and molecular genetic studies", World J Gastroenterol, 2012, 18(13), pp. 1545-1551.
Terry, M., Daiichi Sankyo's Tumor Drug Meets Primary Endpoint in Late-Stage Study. Published: Oct. 31, 2017. (3 pages).
Wei et al., "Regulation of Csf1r and Bcl6 in Macrophages Mediates the Stage-Specific Effects of MicroRNA-155 on Atherosclerosis", Arterioscler Thromb Vasc Biol, 2015, 35, pp. 796-803.
Williams et al., "Neuroinflammation in glaucoma: A new opportunity[1]", Exp Eye Res., 2017, 157, pp. 20-27.
Wong, W.T., "Immune cells in the retina can spontaneously regenerate", ScienceDaily, NIH/National Eye Institute, 2018. (5 pages).
Yu et al., "CSF-1R regulates non-small cell lung cancer cells dissemination through Wnt3a signaling", Am J Cancer Res 2017, 7(11), pp. 2144-2156.

SOLID FORMS OF A COMPOUND MODULATING KINASES

CROSS-REFERENCE TO RELATED APPLICATIONS

This application is a continuation of U.S. application Ser. No. 15/725,197, filed Oct. 4, 2017, now U.S. Pat. No. 10,189,833, which is a divisional of U.S. application Ser. No. 15/147,692, filed May 5, 2016, now U.S. Pat. No. 9,802,932, which application claims the benefit under 35 U.S.C. § 119(e) to U.S. Provisional Application No. 62/157,902, filed May 6, 2015, all of which are hereby incorporated by reference in their entireties.

FIELD

The present disclosure relates generally to solid forms of Compound I, named [5-(5-chloro-1H-pyrrolo[2,3-b]pyridin-3-ylmethyl)-pyridin-2-yl]-(6-trifluoromethyl-pyridin-3-yl-methyl)-amine HCl salt, solid form of its free base, Compound II, processes for making the solid forms, and their therapeutic methods of use.

BACKGROUND

There remains a need to develop effective treatments for subjects suffering from or at risk of a c-Kit and/or c-Fms and/or Flt3 mediated disease or condition. Suitable compounds, including Compound I and Compound II, for the treatment of such diseases and conditions are disclosed in U.S. Pat. No. 7,893,075, U.S. Publication No. 2014-0037617 and U.S. Publication No. 2013-0274259, the disclosures of all of which is incorporated herein by reference in their entirety.

However, Compound I was not heretofore known in any of the specific crystalline forms A-D as described herein. Also, Compound II was not heretofore known in the specific crystalline form as described herein.

SUMMARY

The present disclosure fulfills these needs and others by providing solid forms of Compound I or Compound II. The present disclosure also provides crystalline forms of Compound I or Compound II.

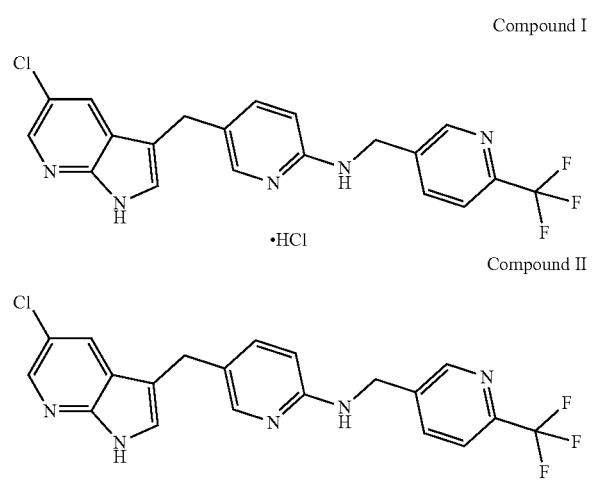

The present disclosure also provides pharmaceutical compositions comprising the solid forms of Compound I or Compound II. The disclosure also provides processes for making the solid forms and methods for using them in the treatment of c-Kit and/or c-Fms and/or Flt3 mediated diseases or conditions.

Thus, one embodiment is directed to a solid form of Compound I. Another embodiment is directed to a polymorphic form of Compound I. Another embodiment is directed to a crystalline form of Compound I. In one embodiment, the crystalline form of Compound I is Compound I Form A. In another embodiment, the crystalline form of Compound I is Compound I Form B. In another embodiment, the crystalline form of Compound I is Compound I Form C. In another embodiment, the crystalline form of Compound I is Compound I Form D. This disclosure also provides a solid form of Compound II. Another embodiment is directed to a crystalline form of Compound II.

Thus, one embodiment is directed to crystalline [5-(5-chloro-1H-pyrrolo[2,3-b]pyridin-3-ylmethyl)-pyridin-2-yl]-(6-trifluoromethyl-pyridin-3-ylmethyl)-amine HCl salt (Compound I Form A). Compound I Form A is characterized by an X-ray powder diffractogram comprising the following peaks (±0.2°): at 7.1, 22.9 and 27.6° 2θ, as determined on a diffractometer using Cu-Kα radiation.

Another embodiment is directed to crystalline [5-(5-chloro-1H-pyrrolo[2,3-b]pyridin-3-ylmethyl)-pyridin-2-yl]-(6-trifluoromethyl-pyridin-3-ylmethyl)-amine HCl salt (Compound I Form B). Compound I Form B is characterized by an X-ray powder diffractogram comprising the following peaks (±0.2°): at 6.6, 23.2 and 28.1° 2θ, as determined on a diffractometer using Cu-Kα radiation.

Another embodiment is directed to crystalline [5-(5-chloro-1H-pyrrolo[2,3-b]pyridin-3-ylmethyl)-pyridin-2-yl]-(6-trifluoromethyl-pyridin-3-ylmethyl)-amine HCl salt (Compound I Form C). Compound I Form C is characterized by an X-ray powder diffractogram comprising the following peaks (±0.2°): at 7.3, 23.3 and 28.2° 2θ, as determined on a diffractometer using Cu-Kα radiation.

Another embodiment is directed to crystalline [5-(5-chloro-1H-pyrrolo[2,3-b]pyridin-3-ylmethyl)-pyridin-2-yl]-(6-trifluoromethyl-pyridin-3-ylmethyl)-amine HCl salt methanol solvate (Compound I Form D). Compound I Form D is characterized by an X-ray powder diffractogram comprising the following peaks (±0.2°): at 6.9, 20.9 and 26.7° 2θ, as determined on a diffractometer using Cu-Kα radiation.

Another embodiment is directed to crystalline [5-(5-chloro-1H-pyrrolo[2,3-b]pyridin-3-ylmethyl)-pyridin-2-yl]-(6-trifluoromethyl-pyridin-3-ylmethyl)-amine (Compound II). Compound II is characterized by an X-ray powder diffractogram comprising the following peaks (±0.2°): at 10.9, 19.7 and 26.4° 2θ, as determined on a diffractometer using Cu-Kα radiation.

One embodiment is a pharmaceutical composition comprising a compound selected from the group consisting of Compound I Form A, Compound I Form B, Compound I Form C and Compound I Form D, crystalline Compound II and a pharmaceutically acceptable excipient.

Another embodiment is directed to a method for treating a subject suffering from or at risk of a disease or condition mediated by a protein kinase selected from c-Fms, c-Kit, Flt3 or combinations thereof and/or macrophages or microglia, comprising administering to the subject a therapeutically effective amount of Compound I Form A, Compound I Form B, Compound I Form C, Compound I Form D or crystalline Compound II.

Another embodiment is directed to a method for treating a subject suffering from or at risk of a disease or condition mediated by a protein kinase selected from c-Fms, c-Kit, Flt3 or combinations thereof and/or macrophages or microglia, comprising administering to the subject a composition comprising a therapeutically effective amount of Compound I Form A, Compound I Form B, Compound I Form C, Compound I Form D or crystalline Compound II and a pharmaceutically acceptable excipient.

Another embodiment is directed to a method for treating a subject suffering from or at risk of tenosynovial giant cell tumor (TGCT) comprising administering to the subject a therapeutically effective amount of Compound I Form A, Compound I Form B, Compound I Form C, Compound I Form D or crystalline Compound II.

Another embodiment is directed to a method for treating a subject suffering from or at risk of pigmented villonodular synovitis (PVNS) comprising administering to the subject a therapeutically effective amount of Compound I Form A, Compound I Form B, Compound I Form C, Compound I Form D, crystalline Compound II or a composition thereof.

Another embodiment is directed to a method for treating a subject suffering from or at risk of malignant peripheral nerve sheath tumors (MPNST) comprising administering to the subject a therapeutically effective amount of Compound I Form A, Compound I Form B, Compound I Form C, Compound I Form D, crystalline Compound II or a composition thereof.

Another embodiment is directed to a method for treating a subject suffering from or at risk of breast cancer comprising administering to the subject a therapeutically effective amount of Compound I Form A, Compound I Form B, Compound I Form C, Compound I Form D, crystalline Compound II or a composition thereof.

Another embodiment is directed to a method for treating a subject suffering from or at risk of plexiform neurofibromas comprising administering to the subject a therapeutically effective amount of Compound I Form A, Compound I Form B, Compound I Form C, Compound I Form D, crystalline Compound II or a composition thereof.

Another embodiment is directed to a method for treating a subject suffering from or at risk of melanoma, or unresectable or metastatic melanoma with a KIT mutation, comprising administering to the subject a therapeutically effective amount of Compound I Form A, Compound I Form B, Compound I Form C, Compound I Form D, crystalline Compound II or a composition thereof.

Another embodiment is directed to a method for treating a subject suffering from or at risk of glioblastoma comprising administering to the subject a therapeutically effective amount of Compound I Form A, Compound I Form B, Compound I Form C, Compound I Form D, crystalline Compound II or a composition thereof.

Another embodiment is directed to a method for treating a subject suffering from or at risk of acute myeloid leukemia comprising administering to the subject a therapeutically effective amount of Compound I Form A, Compound I Form B, Compound I Form C, Compound I Form D, crystalline Compound II or a composition thereof.

Another embodiment is directed to a method for treating a subject suffering from or at risk of ovarian cancer comprising administering to the subject a therapeutically effective amount of Compound I Form A, Compound I Form B, Compound I Form C, Compound I Form D, crystalline Compound II or a composition thereof.

Another embodiment is directed to preparing a capsule comprising Compound I Form C comprising combining Compound I Form C with a pharmaceutically acceptable carrier or excipient.

Another embodiment is directed to preparing a tablet comprising Compound I Form C comprising combining Compound I Form C with a pharmaceutically acceptable carrier or excipient.

Still an additional embodiment includes, optionally in combination with any other embodiment described herein, is the use of any one of Compound I Forms A-D or crystalline Compound II in the manufacture of a medicament for treating subjects suffering from or at risk of a disease or condition mediated by a protein kinase selected from c-Fms, c-Kit, Flt3 or combinations thereof and/or macrophages or microglia.

DETAILED DESCRIPTION

Figure 1:
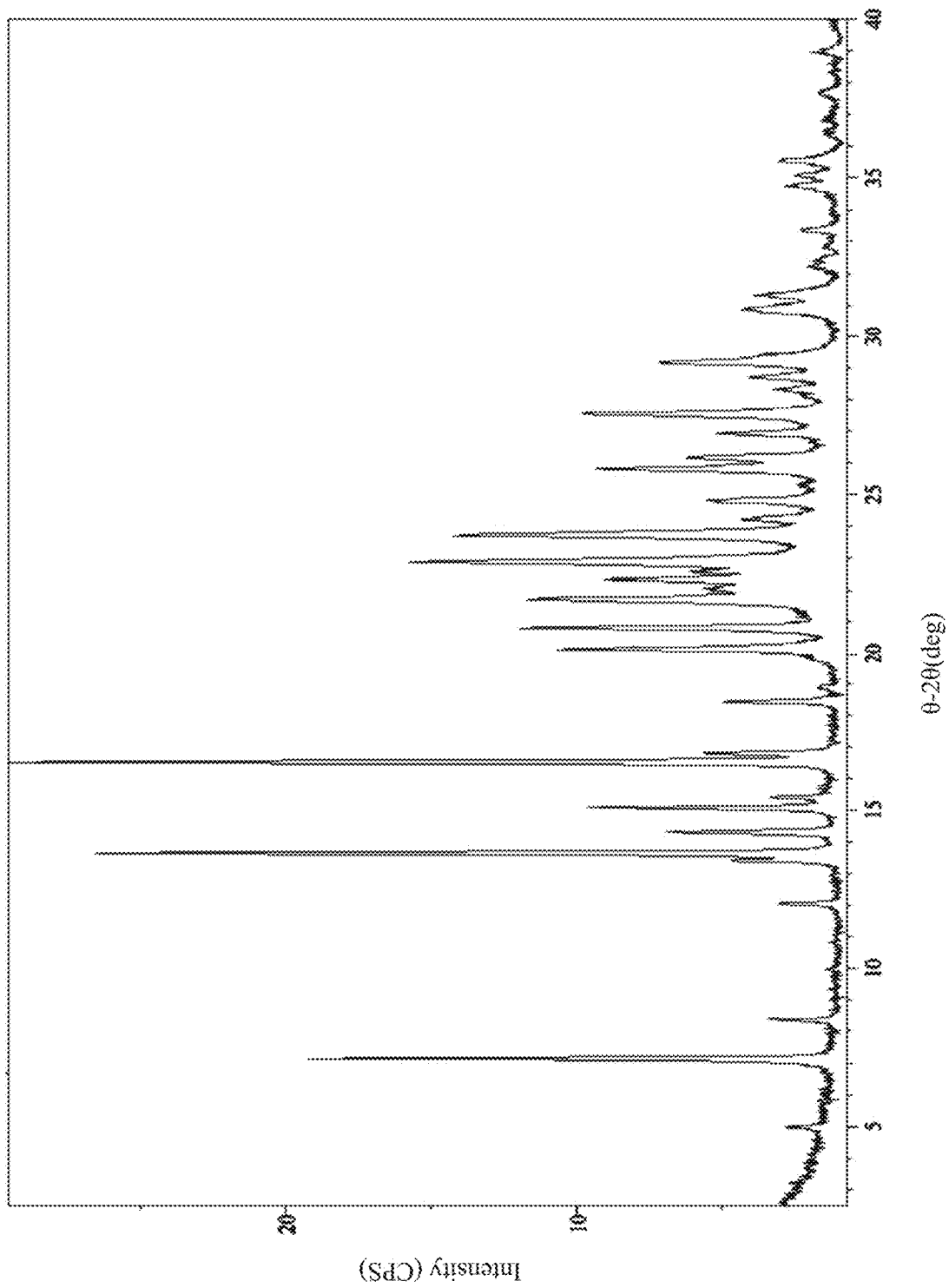
FIG. 1 is an X-ray powder diffraction pattern of Compound I Form A.

The compound named [5-(5-chloro-1H-pyrrolo[2,3-b]pyridin-3-ylmethyl)-pyridin-2-yl]-(6-trifluoromethyl-pyridin-3-ylmethyl)-amine HCl salt (Compound I), or its free base (Compound II), is useful in treatments for subjects suffering from or at risk of a c-Kit and/or c-Fms mediated disease or condition and has the following structure:

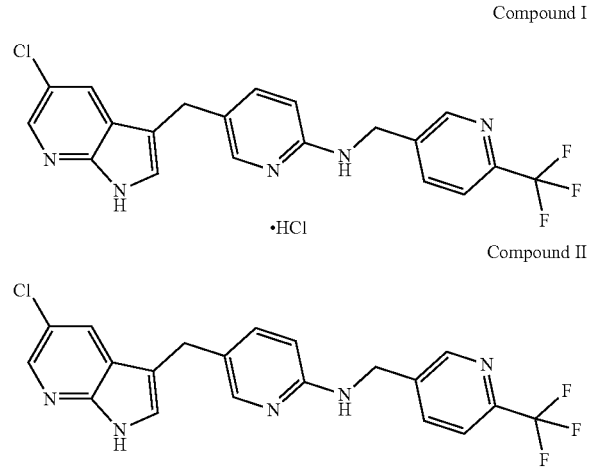

The present disclosure relates to solid forms of Compounds I and II. The present disclosure also relates to polymorphic forms of Compounds I and II. The present disclosure also relates to various crystalline forms of Compound I or a crystalline form of Compound II and processes for making the crystalline forms. The crystalline forms of Compound I are described herein as "Compound I Form A," "Compound I Form B," "Compound I Form C," and "Compound I Form D." In some embodiments, such forms of Compound I may be a solvate.

Definitions

As used herein the following definitions apply unless clearly indicated otherwise.

All atoms designated within a Formula described herein, either within a structure provided, or within the definitions of variables related to the structure, is intended to include any isotope thereof, unless clearly indicated to the contrary. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^1H$, $^2H$, $^3H$; carbon includes for example $^{11}C$, $^{12}C$, $^{13}C$, $^{14}C$; oxygen includes for example $^{16}O$, $^{17}O$, $^{18}O$ nitrogen includes for example $^{13}N$, $^{14}N$, $^{15}N$; sulfur includes for example $^{32}S$, $^{33}S$, $^{34}S$, $^{35}S$, $^{36}S$, $^{37}S$, $^{38}S$; fluoro includes for example $^{17}F$, $^{18}F$, $^{19}F$; chloro includes for example $^{35}Cl$, $^{36}Cl$, $^{37}Cl$, $^{38}Cl$, $^{39}Cl$; and the like.

Certain compounds contemplated for use in accordance with the present disclosure can exist in unsolvated forms as well as solvated forms, including hydrated forms. "Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate, hemi-hydrate, channel hydrate etc. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure. Certain compounds contemplated for use in accordance with the present disclosure may exist in multiple crystalline or amorphous forms. In general, all physical forms are equivalent for the uses contemplated by the present disclosure and are intended to be within the scope of the present disclosure.

The term "desolvated" refers to a Compound I form that is a solvate as described herein, and from which solvent molecules have been partially or completely removed. Desolvation techniques to produce desolvated forms include, without limitation, exposure of a Compound I form (solvate) to a vacuum, subjecting the solvate to elevated temperature, exposing the solvate to a stream of gas, such as air or nitrogen, or any combination thereof. Thus, a desolvated Compound I form can be anhydrous, i.e., completely without solvent molecules, or partially solvated wherein solvent molecules are present in stoichiometric or non-stoichiometric amounts.

As used herein, the term "solid form" refers to a type of solid-state material that includes amorphous as well as crystalline forms. The term "crystalline form" refers to polymorphs as well as solvates, hydrates, etc. The term "polymorph" refers to a particular crystal structure having particular physical properties such as X-ray diffraction, melting point, and the like.

The term "condis crystal" refers to mesophase or liquid crystal, and it is a state of matter that falls between a crystal and a liquid. It is a crystal in which the positional and conformational order in the packing of macromolecules arranged in parallel is lost to some degree. Condis crystal particles may look like solid crystals, but may flow like a liquid when these crystals are pressed upon.

As used herein, the terms "treat", "treating", "therapy", "therapies", and like terms refer to the administration of material, e.g., any one or more compound(s) as described herein in an amount effective to prevent, alleviate, or ameliorate one or more symptoms of a disease or condition, i.e., indication, and/or to prolong the survival of the subject being treated.

Compound I and Compound II are inhibitors of Fms, Kit and Flt3 protein kinases. The Kinase assays that can measure the $IC_{50}$ values for these targets are described in US Publication Nos. US 2007/0032519, US 2009/0076046 and US 2011/0112127. Compound I and II have $IC_{50}$ values of less than 0.05 μM for each of these three kinase targets.

As used herein, the term "Fms and/or Kit and/or Flt3 protein kinase mediated disease or condition" refers to a disease or condition in which the biological function of a Fms protein kinase, including any mutation thereof, a Kit protein kinase, including any mutation thereof, a Flt3 protein kinase, including any mutation thereof or both a Fms and Kit protein kinase, including any mutations thereof, affects the development, course, and/or symptoms of the disease or condition, and/or in which modulation of the Fms and/or Kit and/r Flt3 protein kinase alters the development, course, and/or symptoms of the disease or condition. A Fms and/or Kit and/or Flt3 protein kinase mediated disease or condition includes a disease or condition for which modulation provides a therapeutic benefit, e.g. wherein treatment with Fms and/or Kit and/or Flt3 protein kinase inhibitor(s), including one or more solid, crystalline or polymorphs of Compound I or solid or crystalline forms of Compound II as described herein, or a composition thereof as described herein, and optionally in combination with another therapeutic agent or therapy as described herein provides a therapeutic benefit to the subject suffering from or at risk of the disease or condition.

As used herein, the terms "Fms protein kinase mediated disease or condition," "c-Fms mediated disease or condition," and the like refer to a disease or condition in which the biological function of a Fms protein kinase, including any mutations thereof, affects the development, course, and/or symptoms of the disease or condition, and/or in which modulation of the Fms protein kinase alters the development, course, and/or symptoms of the disease or condition. The Fms protein kinase mediated disease or condition includes a disease or condition for which Fms inhibition provides a therapeutic benefit, e.g. wherein treatment with Fms inhibitor(s), including one or more solid, crystalline or polymorphs of Compound I or solid or crystalline forms of Compound II as described herein, or a composition thereof as described herein, and optionally in combination with another therapeutic agent or therapy as described herein provides a therapeutic benefit to the subject suffering from or at risk of the disease or condition.

As used herein, the terms "Kit protein kinase mediated disease or condition," "c-Kit mediated disease or condition," and the like refer to a disease or condition in which the biological function of a Kit protein kinase, including any mutations thereof, affects the development, course, and/or symptoms of the disease or condition, and/or in which modulation of the Kit protein kinase alters the development, course, and/or symptoms of the disease or condition. The Kit protein kinase mediated disease or condition includes a disease or condition for which Kit inhibition provides a therapeutic benefit, e.g. wherein treatment with Kit inhibitor(s), including one or more solid, crystalline or polymorphs of Compound I or solid or crystalline forms of Compound II as described herein, or a composition thereof as described herein, and optionally in combination with another therapeutic agent or therapy as described herein provides a therapeutic benefit to the subject suffering from or at risk of the disease or condition.

As used herein, the term "composition" refers to a pharmaceutical preparation suitable for administration to an intended subject for therapeutic purposes that contains at least one pharmaceutically active compound, including any solid form thereof. The composition may include at least one pharmaceutically acceptable component to provide an improved formulation of the compound, such as a suitable carrier or excipient.

As used herein, the term "subject" refers to a living organism that is treated with compounds as described herein, including, but not limited to, any mammal, such as a human, other primates, sports animals, animals of commercial interest such as cattle, farm animals such as horses, or pets such as dogs and cats.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated. The therapeutically effective amount will vary depending on the compound, the disorder or condition and its severity and the age, weight, etc., of the mammal to be treated. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art.

As used herein, the term "modulating" or "modulate" refers to an effect of altering a biological activity, especially a biological activity associated with a particular biomolecule such as a protein kinase. For example, an inhibitor of a particular biomolecule modulates the activity of that biomolecule, e.g., an enzyme, by decreasing the activity of the biomolecule, such as an enzyme. Such activity is typically indicated in terms of an inhibitory concentration ($IC_{50}$) of the compound for an inhibitor with respect to, for example, an enzyme.

As used herein, the phrase "substantially as shown in Figure" as applied to DSC thermograms is meant to include a variation of ±3° Celsius and as applied to thermogravimetric analysis (TGA) is meant to include a variation of ±2% in weight loss.

As used herein, the phrase "major peaks" in the XRPD pattern refers to a subset of the entire observed peak list. Major peaks are selected from observed peaks by identifying preferably non-overlapping, low-angle peaks, with strong intensity.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

In addition, abbreviations as used herein have respective meanings as follows:

| | |
|---|---|
| D | Days |
| DMSO | Dimethylsulfoxide |
| DSC | differential scanning calorimetry |
| DVS | dynamic vapor sorption |
| EtOAc | ethyl acetate |
| EtOH | Ethanol |
| HPLC | High pressure liquid chromatography |
| IPA | Isopropanol |
| IR | Infrared spectrum |
| kV | Kilovolt |
| mA | Milliampere |
| MeOH | Methanol |
| Pks | Peaks |
| RH | relative humidity |
| RT | room temperature |
| TGA | thermogravimetric analysis |
| μL | Microliter |
| μm | Micrometer |
| μM | Micromolar |
| v/v | volume to volume |
| XRPD | X-ray powder diffraction |

Compounds I and II

Compounds I and II were synthesized according to the following synthetic procedure of Scheme I:

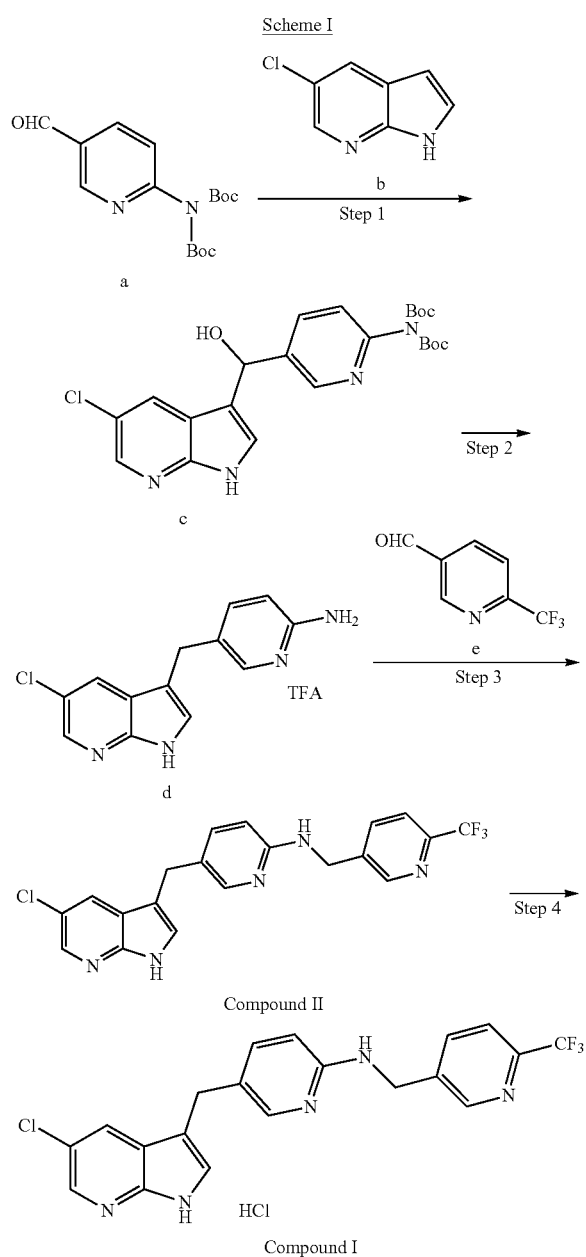

Scheme I

Step 1: Conversion of (a) to (c)

The reactor was charged with isopropyl alcohol, and the chamber was flushed with nitrogen. Tert-butyl[(tert-butoxy)-N-(5-formyl-(2-pyridyl))carbonylamino]formate (a) was dissolved in isopropyl alcohol with stirring, and the reaction mixture was cooled to about 0-5° C. 5-Chloro-7-azaindole (b), potassium carbonate, and tetrabutylammonium bisulfate were added one by one to the reactor, and the reaction mixture was stirred at room temperature for about 24 hours. The reaction progress was monitored by analyzing the reaction mixture by HPLC. When the content of (a) was 2% or less, the reaction was cooled to about 5-10° C., and purified water was added to precipitate crude tert-butyl[(tert-butoxy)-N-{5-[(5-chloropyrrolo[2,3-b]pyridine-3-yl)hydroxymethyl]-(2-pyridyl)}carbonylamino)formate (c). The precipitate was filtered, washed with purified water, dried, and tested for purity. If the purity was ≥90% no further work-up was conducted. If the purity was <90%, the crude product was stirred with hot ethyl acetate for about 1 hour, cooled to about 0-5° C., and filtered. The filtered solids were washed with ethyl acetate and dried.

Step 2: Conversion of (c) to (d)

The reactor was charged with acetonitrile, and the chamber was flushed with nitrogen. Compound (c) was dissolved in acetonitrile with stirring, and the reaction mixture was cooled to about 0-5° C. Triethylsilane and trifluoroacetic acid were added to the reactor, and the reaction mixture was stirred at room temperature for about 24 hours and then refluxed for about 8 hours. The reaction progress was monitored by analyzing the reaction mixture by HPLC. When the (c) content was ≤1.0%, crude 5-(5-chloro-1H-pyrrolo[2,3-b]pyridin-3-ylmethyl]-pyridin-2-ylamine trifluoroacetic acid salt (d) was precipitated by concentrating the volume, adding water, and concentrating again. The suspension was stirred for 1 to 1.5 hours at about 60-65° C., cooled to about 0-5° C., and filtered, and the resulting solids were washed with purified water. The solids were then stirred with ethyl acetate for about 3 hours, filtered, washed with ethyl acetate and dried.

Step 3: Conversion of (d) to Compound II (Free Base)

The reactor was charged with acetonitrile, and the chamber was flushed with nitrogen. Compound (d) and 6-trifluoromethyl-pyridine-3-carboxaldehyde (e) were dissolved in acetonitrile with stirring, and the reaction mixture was cooled to about 0-5° C. Trifluoroacetic acid was added to the reactor, and the reaction mixture was stirred for about 6 hours at about 10° C. Triethylsilane was then added to the reactor, and the reaction mixture was refluxed for about 24 hours. The reaction progress was monitored by analyzing the reaction mixture by HPLC. When Compound II content was ≤1.0% the reaction was worked up by concentrating the volume, adding water, and concentrating again. Ammonium hydroxide was then added to raise the pH of the liquid to be between 8 and 9 and precipitate crude Compound II. The solids were filtered, washed with purified water and dried.

Step 4: Conversion of Compound II to Compound I.

The reactor was charged with ethyl acetate, and the chamber was flushed with nitrogen. Compound II was heated with ethyl acetate at about 55° C. for 7 to 8 hours, cooled to room temperature, stirred for about 16 hours, filtered, and dried. Compound II was reacted with 1.25 equivalents of hydrochloric acid in methanol at <30° C. then heated at reflux for about 1 hour, filtered then cooled to room temperature. The slurry was filtered and the solids were refluxed in methyl tert-butyl ether, cooled to room temperature, filtered, and dried to isolate Compound I.

Crystalline Forms of Compound I

As described generally above, the present disclosure provides crystalline forms of Compound I, and a crystalline form of its free base, Compound II, which are disclosed herein.

In one embodiment, this disclosure provides a process of preparing Compound I Form A comprising recrystallizing Compound I from a mixture of methanol and water.

Compound I Form A is characterized by an X-ray powder diffractogram comprising peaks (±0.2°) at 7.1, 22.9 and 27.6° 2θ, as determined on a diffractometer using Cu-Kα radiation. The diffractogram comprises additional peaks (±0.2°) at 21.7 and 23.7° 2θ. Form A is also characterized by its full X-ray powder diffractogram as substantially shown in FIG. 1. Major peaks in the XRPD pattern are shown in Table 1 below. In one embodiment, this disclosure provides Compound I Form A comprising two or more peaks (±0.2°) listed in the Table 1 below as determined on a diffractometer using Cu-Kα radiation.

TABLE 1

Major Peaks in the XRPD Pattern for Compound I Form A

| °2θ (±0.2°) | d-space [Å] |
|---|---|
| 7.14 | 12.368 ± 0.346 |
| 13.65 | 6.482 ± 0.095 |
| 14.32 | 6.179 ± 0.086 |
| 15.08 | 5.870 ± 0.077 |
| 16.52 | 5.363 ± 0.064 |
| 16.78 | 5.278 ± 0.062 |
| 20.16 | 4.402 ± 0.043 |
| 20.81 | 4.265 ± 0.041 |
| 21.72 | 4.089 ± 0.037 |
| 22.04 | 4.030 ± 0.036 |
| 22.34 | 3.977 ± 0.035 |
| 22.59 | 3.933 ± 0.034 |
| 22.89 | 3.882 ± 0.033 |
| 23.74 | 3.745 ± 0.031 |
| 24.80 | 3.587 ± 0.028 |
| 25.81 | 3.450 ± 0.026 |
| 26.16 | 3.404 ± 0.026 |
| 27.55 | 3.235 ± 0.023 |
| 29.17 | 3.059 ± 0.021 |

Figure 2:
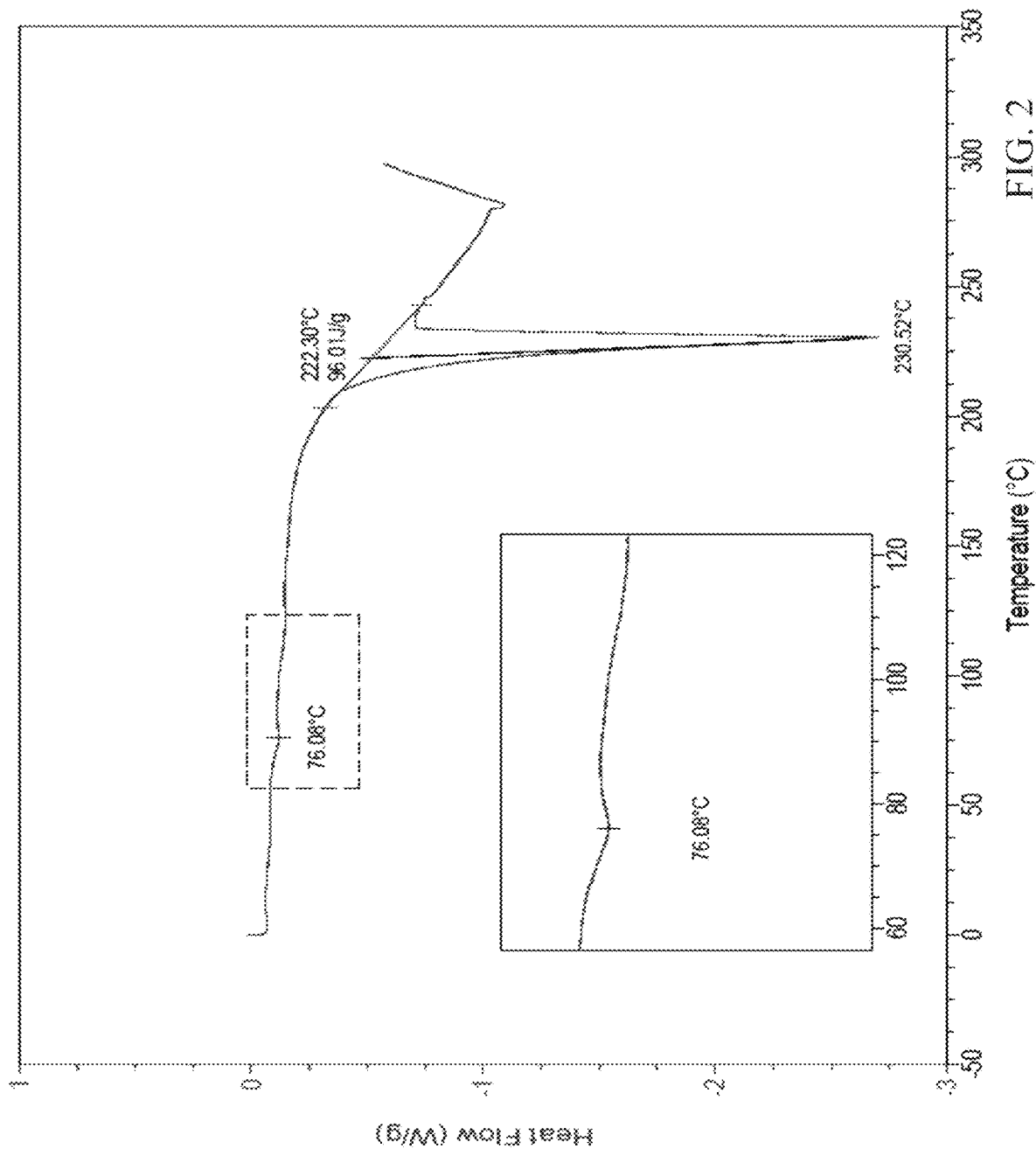
FIG. 2 is differential scanning calorimetry (DSC) curve of Compound I Form A.

In some embodiments, Form A is also characterized by its differential scanning calorimetry (DSC) curve comprising an endotherm comprising signal maximum at about 231° C. with an onset temperature at about 222° C. In another embodiment, the DSC curve is substantially as shown in FIG. 2.

Figure 3:
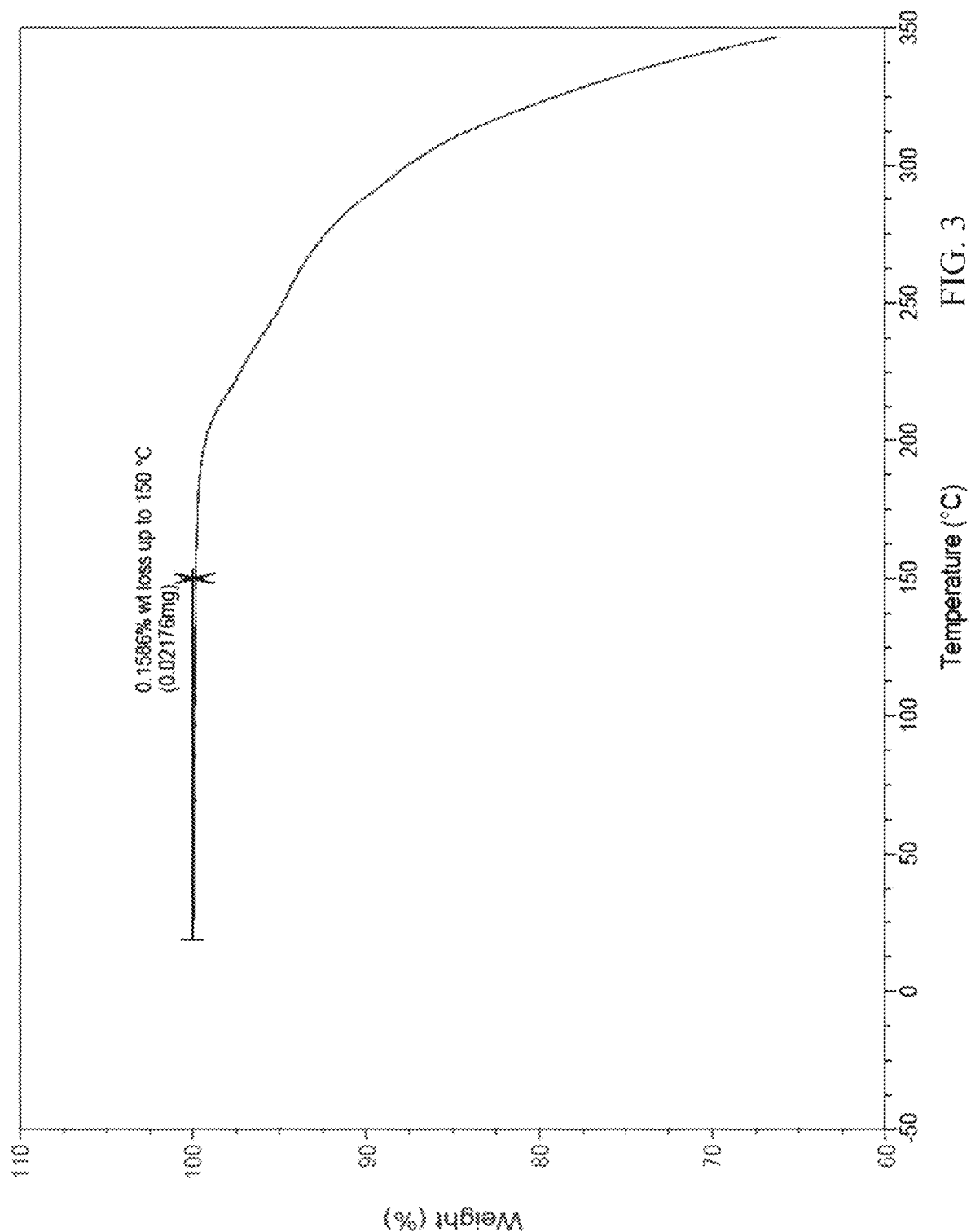
FIG. 3 is thermogravimetric analysis (TGA) of Compound I Form A.

In some embodiments, Form A is also characterized by thermogravimetric analysis (TGA) comprising a thermogram substantially as shown in FIG. 3.

Figure 4:
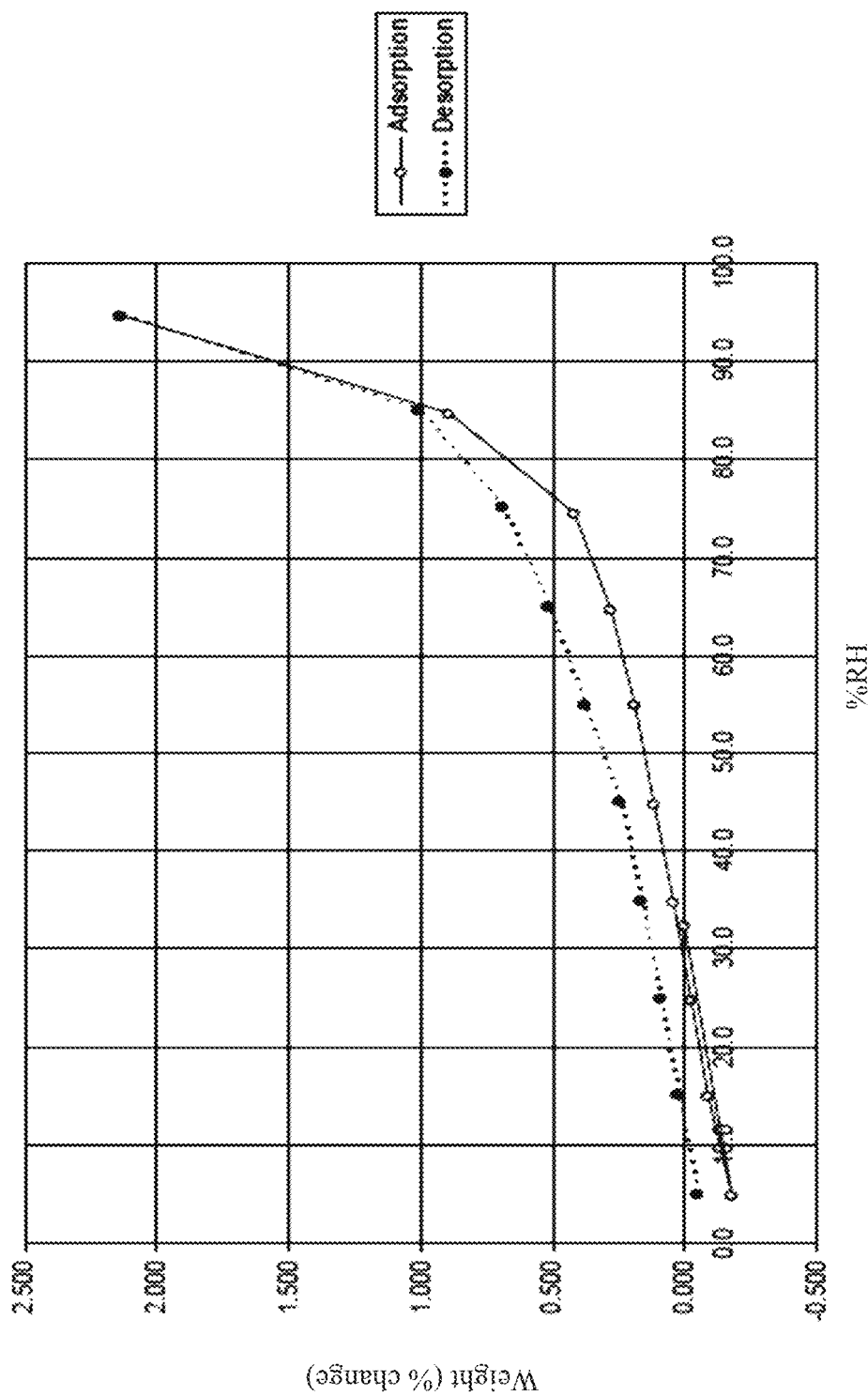
FIG. 4 is dynamic vapor sorption (DVS) curve of Compound I Form A.

In some embodiments, Form A is also characterized by a dynamic vapor sorption (DVS) curve substantially as shown in FIG. 4.

Figure 5:
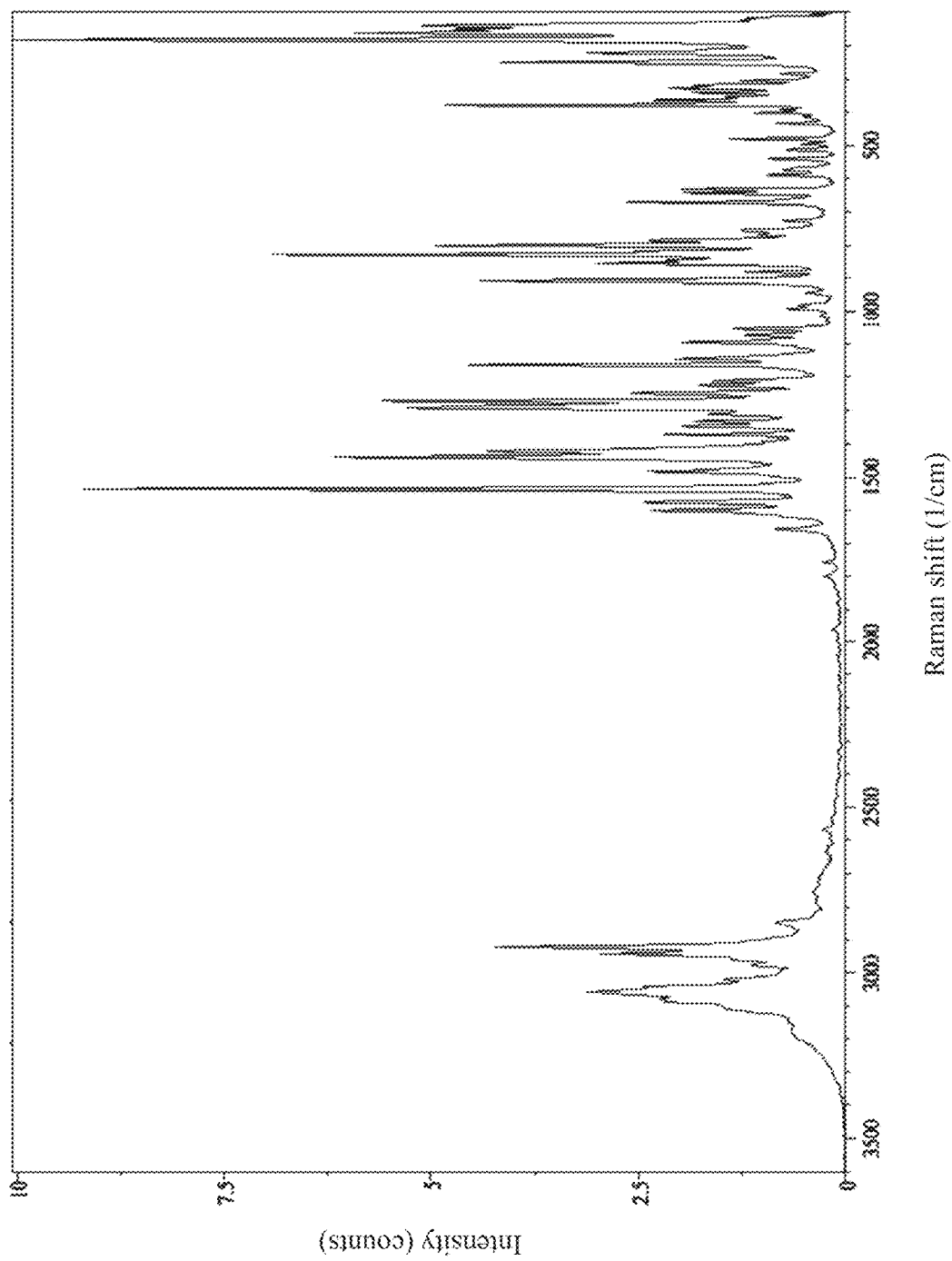
FIG. 5 is Raman spectrum of Compound I Form A.

In some embodiments, Form A is also characterized by a Raman spectrum substantially as shown in FIG. 5.

Figure 15:
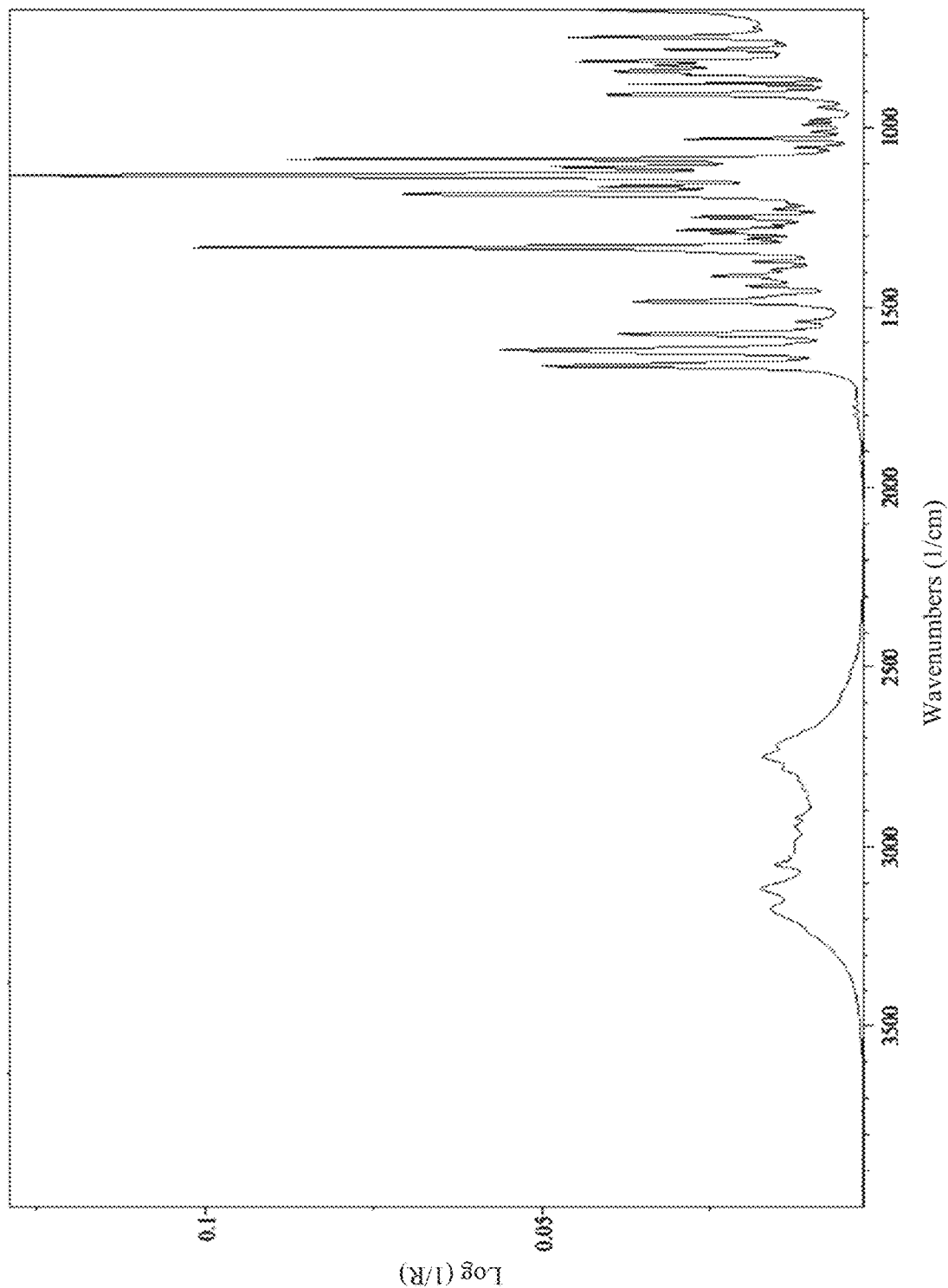
FIG. 15 is IR spectra of Compound I Form A.

In some embodiments, Compound I Form A is also characterized by its IR spectrum as shown in FIG. 15.

In another embodiment, this disclosure provides a process of preparing Compound I Form B comprising contacting Compound II (free base) with hydrochloric acid. Compound I Form B is characterized by an X-ray powder diffractogram comprising peaks (±0.2°) at 6.6, 23.2 and 28.1° 2θ, as determined on a diffractometer using Cu-Kα radiation. The diffractogram comprises additional peaks (±0.2°) at 22.3 and 26.7° 2θ. Form B is also characterized by its full X-ray powder diffractogram as substantially shown in FIG. 6. Major peaks in the XRPD pattern are shown in Table 2 below. In one embodiment, this disclosure provides Compound I Form B comprising two or more peaks (±0.2°) listed in the Table 2 below as determined on a diffractometer using Cu-Kα radiation.

TABLE 2

Major Peaks in the XRPD Pattern for Compound I Form B

| °2θ (±0.2°) | d-space [Å] |
|---|---|
| 6.63 | 13.320 ± 0.401 |
| 7.15 | 12.360 ± 0.345 |
| 8.37 | 10.560 ± 0.252 |
| 13.66 | 6.477 ± 0.094 |
| 14.34 | 6.170 ± 0.086 |
| 15.10 | 5.862 ± 0.077 |
| 16.54 | 5.356 ± 0.064 |
| 17.45 | 5.078 ± 0.058 |
| 20.19 | 4.395 ± 0.043 |
| 20.83 | 4.261 ± 0.040 |
| 21.27 | 4.175 ± 0.039 |
| 21.59 | 4.113 ± 0.038 |
| 21.86 | 4.063 ± 0.037 |
| 22.34 | 3.975 ± 0.035 |
| 22.59 | 3.934 ± 0.034 |
| 23.17 | 3.836 ± 0.033 |
| 23.76 | 3.741 ± 0.031 |
| 23.96 | 3.712 ± 0.031 |
| 25.98 | 3.427 ± 0.026 |
| 26.22 | 3.397 ± 0.025 |
| 26.46 | 3.365 ± 0.025 |
| 26.67 | 3.340 ± 0.025 |
| 28.14 | 3.168 ± 0.022 |
| 28.72 | 3.106 ± 0.021 |
| 29.92 | 2.984 ± 0.019 |

Figure 7:
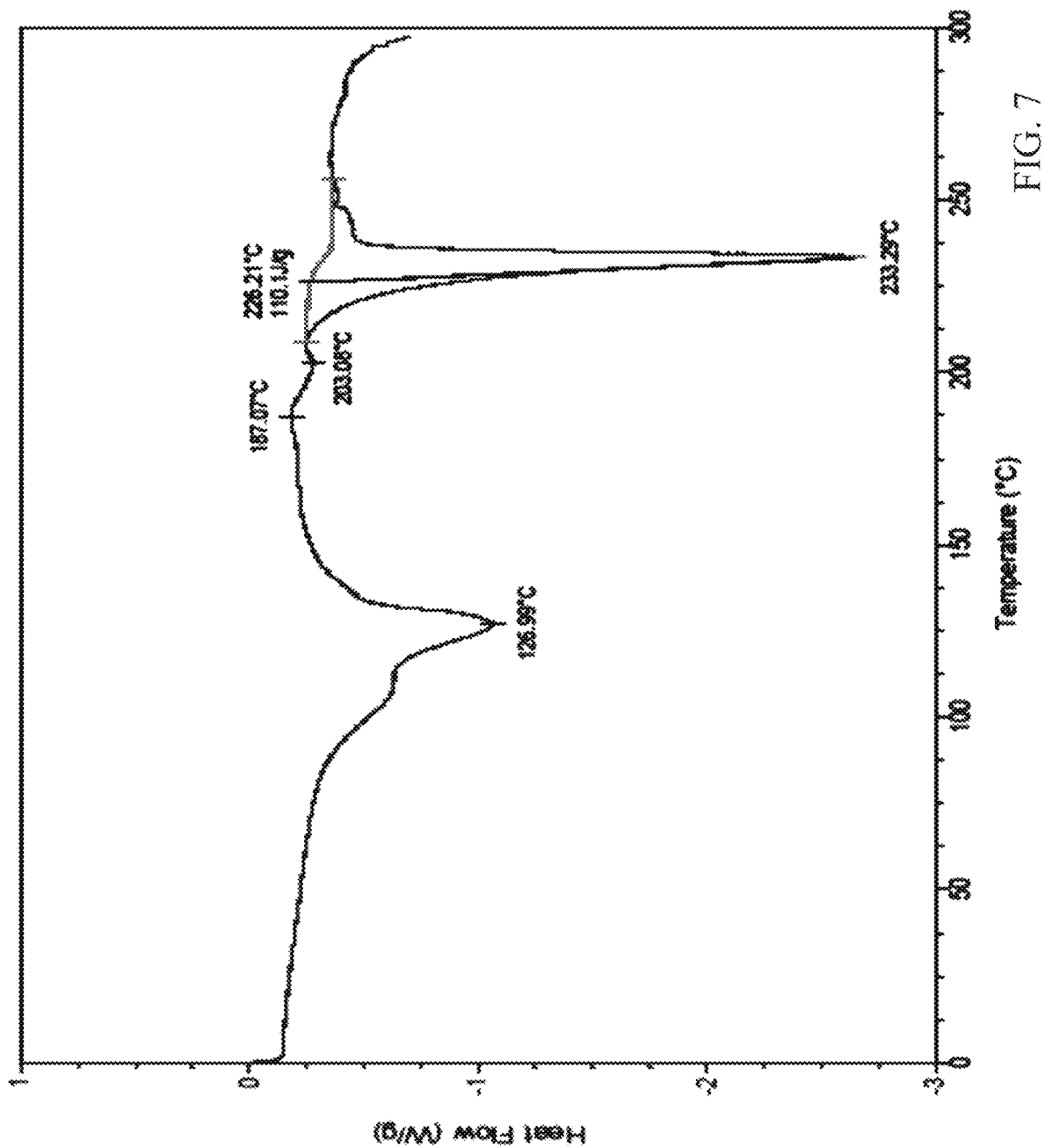
FIG. 7 is differential scanning calorimetry (DSC) curve of Compound I Form B.

In some embodiments, Form B is also characterized by its differential scanning calorimetry (DSC) curve comprising endotherms comprising signal maximums at about 127° C. and 233° C. (with an onset temperature at about 226° C.). In another embodiment, the DSC curve is substantially as shown in FIG. 7.

Figure 8:
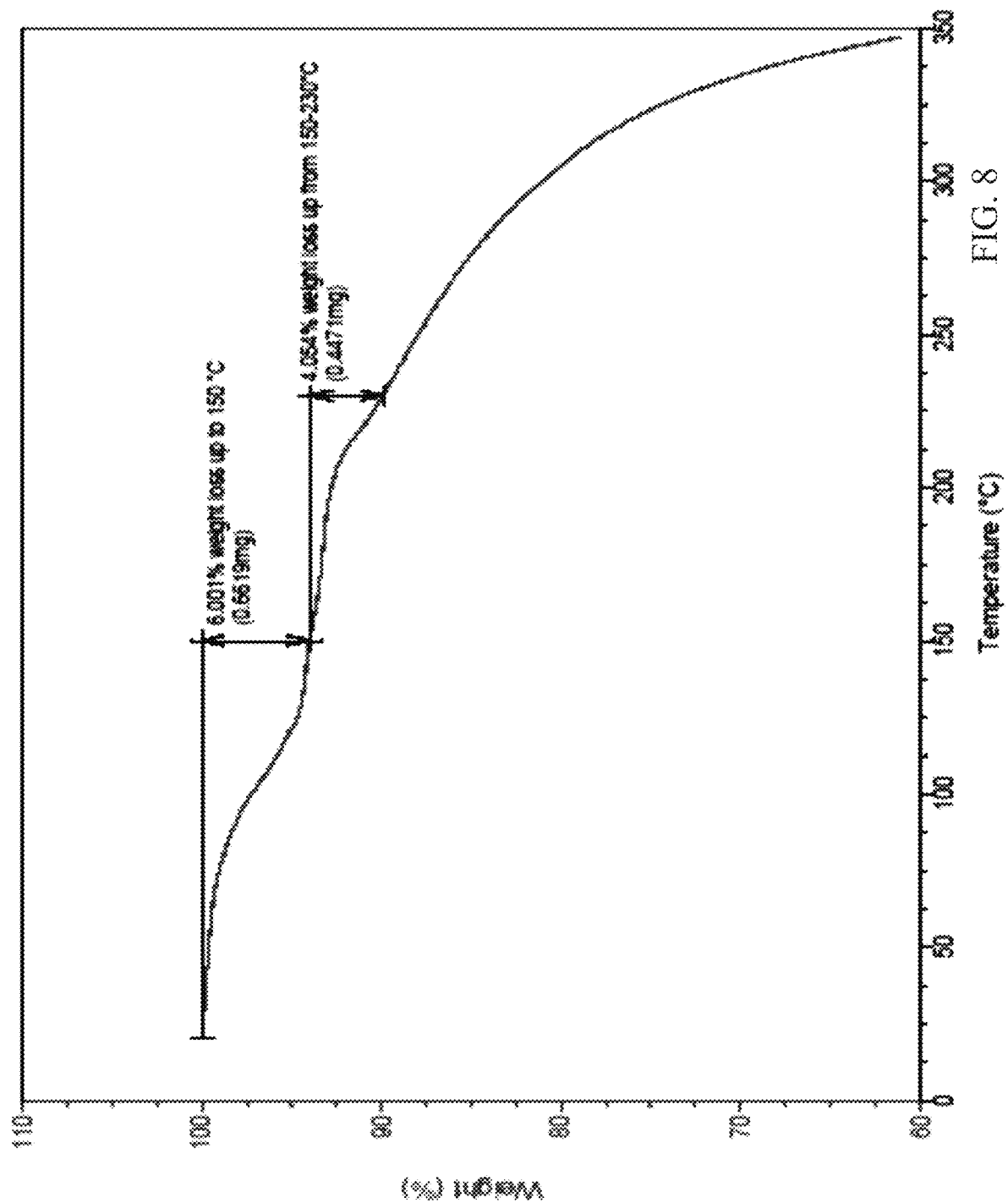
FIG. 8 is thermogravimetric analysis (TGA) of Compound I Form B.

In some embodiments, Form B is also characterized by thermogravimetric analysis (TGA) comprising a thermogram substantially as shown in FIG. 8.

Figure 9:
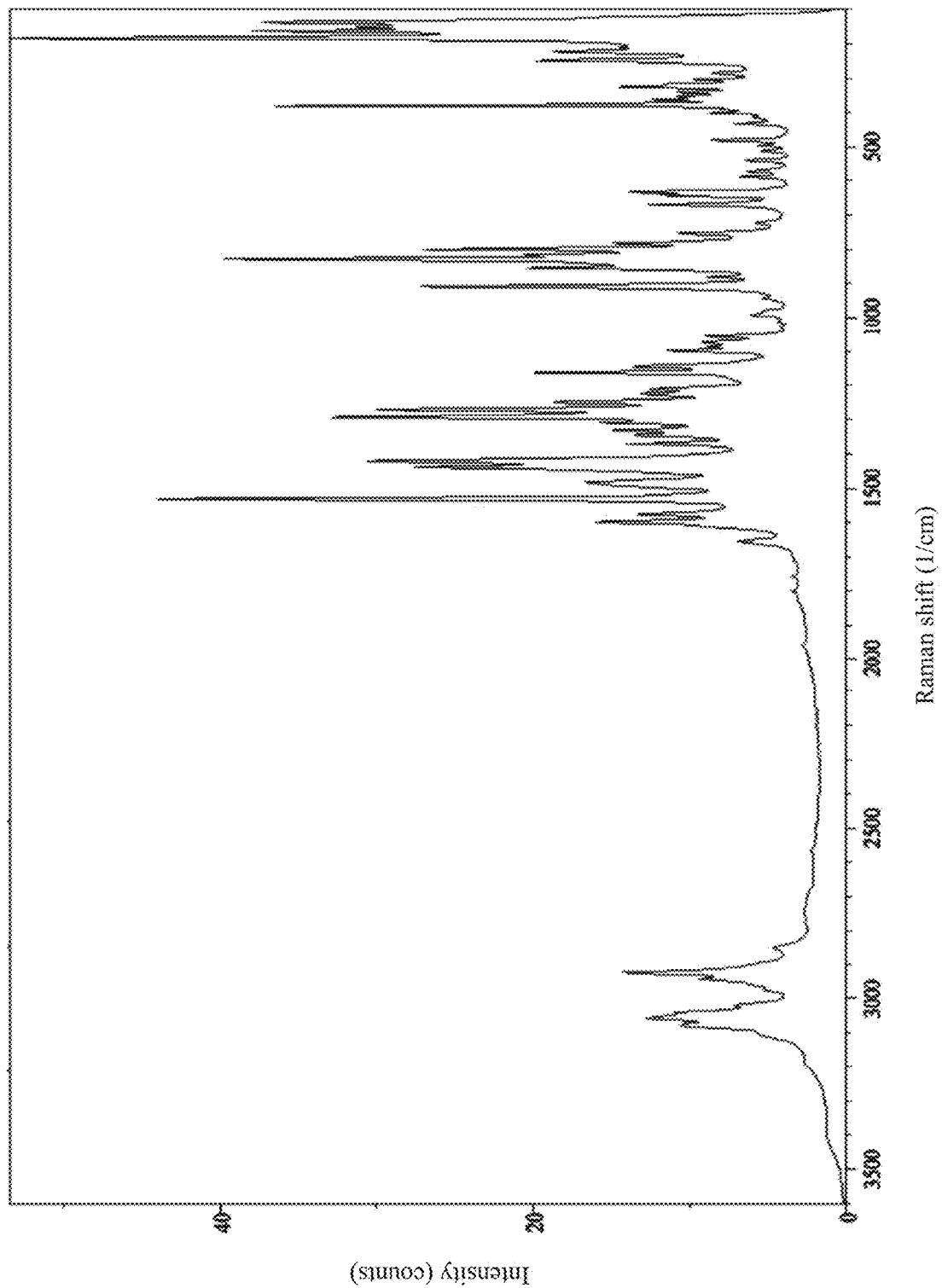
FIG. 9 is Raman spectrum of Compound I Form B.

In some embodiments, Form B is also characterized by a Raman spectrum substantially as shown in FIG. 9.

Figure 16:
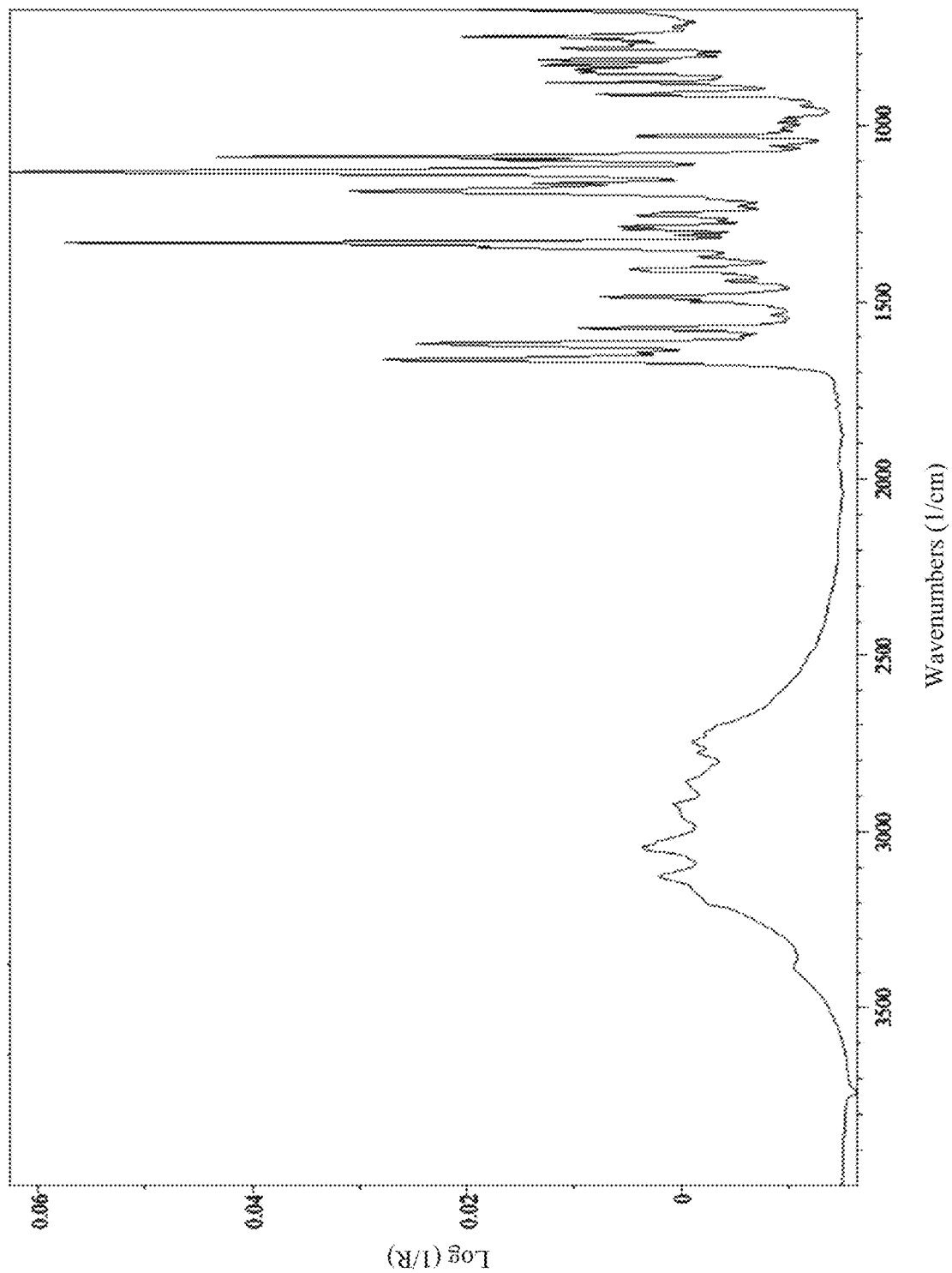
FIG. 16 is IR spectra of Compound I Form B.

In some embodiments, Compound I Form B is also characterized by its IR spectrum as shown in FIG. 16.

In another embodiment, this disclosure provides a process of preparing Compound I Form C comprising recrystallizing Compound I Form A from a solvent selected from acetone, 1,4-dioxane, ethanol, methanol, and a mixture of isopropanol and water. In another embodiment, this disclosure provides a process of preparing Compound I Form C comprising recrystallizing Compound I Form A from ethanol.

Compound I Form C is characterized by an X-ray powder diffractogram comprising peaks (±0.2°) at 7.3, 23.3 and 28.2° 2θ, as determined on a diffractometer using Cu-Kα radiation. The diffractogram comprises additional peaks (±0.2°) at 16.6 and 20.9° 2θ. Form C is also characterized by its full X-ray powder diffractogram as substantially shown in FIG. 10. Major peaks in the XRPD pattern are shown in Table 3 below. In one embodiment, this disclosure provides Compound I Form C comprising two or more peaks (±0.2°) listed in the Table 3 below as determined on a diffractometer using Cu-Kα radiation.

TABLE 3

Major Peaks in the XRPD Pattern for Compound I Form C

| °2θ (±0.2°) | d-space [Å] |
|---|---|
| 7.3 | 12.176 ± 0.335 |
| 8.5 | 10.422 ± 0.245 |
| 13.8 | 6.427 ± 0.093 |
| 14.4 | 6.127 ± 0.084 |
| 15.2 | 5.820 ± 0.076 |
| 16.6 | 5.321 ± 0.063 |
| 16.9 | 5.240 ± 0.062 |
| 20.3 | 4.372 ± 0.043 |

TABLE 3-continued

Major Peaks in the XRPD Pattern for Compound I Form C

| °2θ (±0.2°) | d-space [Å] |
|---|---|
| 20.9 | 4.239 ± 0.040 |
| 21.3 | 4.159 ± 0.039 |
| 22.4 | 3.968 ± 0.035 |
| 23.3 | 3.816 ± 0.032 |
| 26.7 | 3.331 ± 0.024 |
| 28.2 | 3.160 ± 0.022 |

Figure 11:
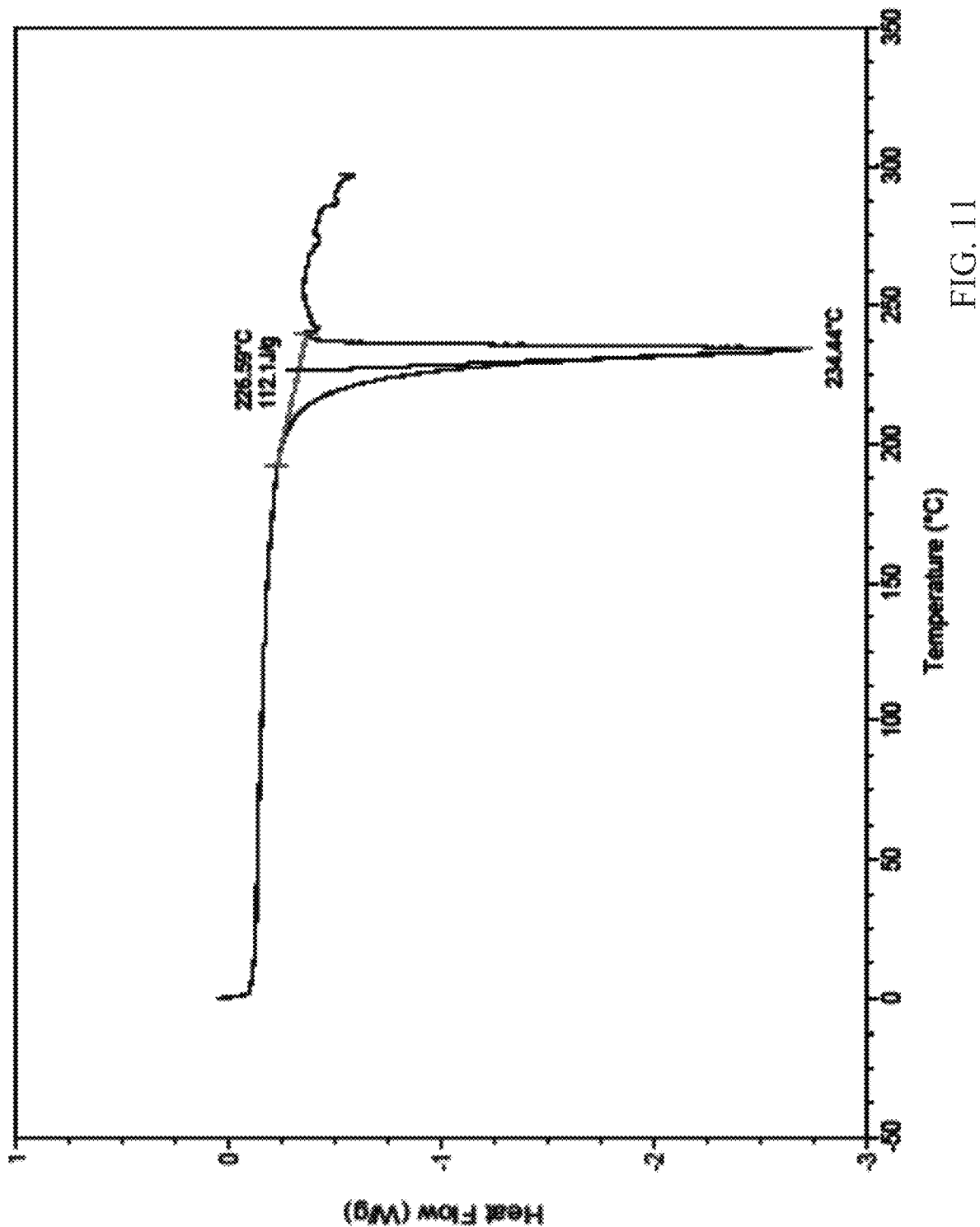
FIG. 11 is differential scanning calorimetry (DSC) curve of Compound I Form C.

In some embodiments, Form C is also characterized by its differential scanning calorimetry (DSC) curve comprising an endotherm comprising signal maximum at about 234° C. with an onset temperature of about 227° C. In another embodiment, the DSC curve is substantially as shown in FIG. 11.

Figure 12:
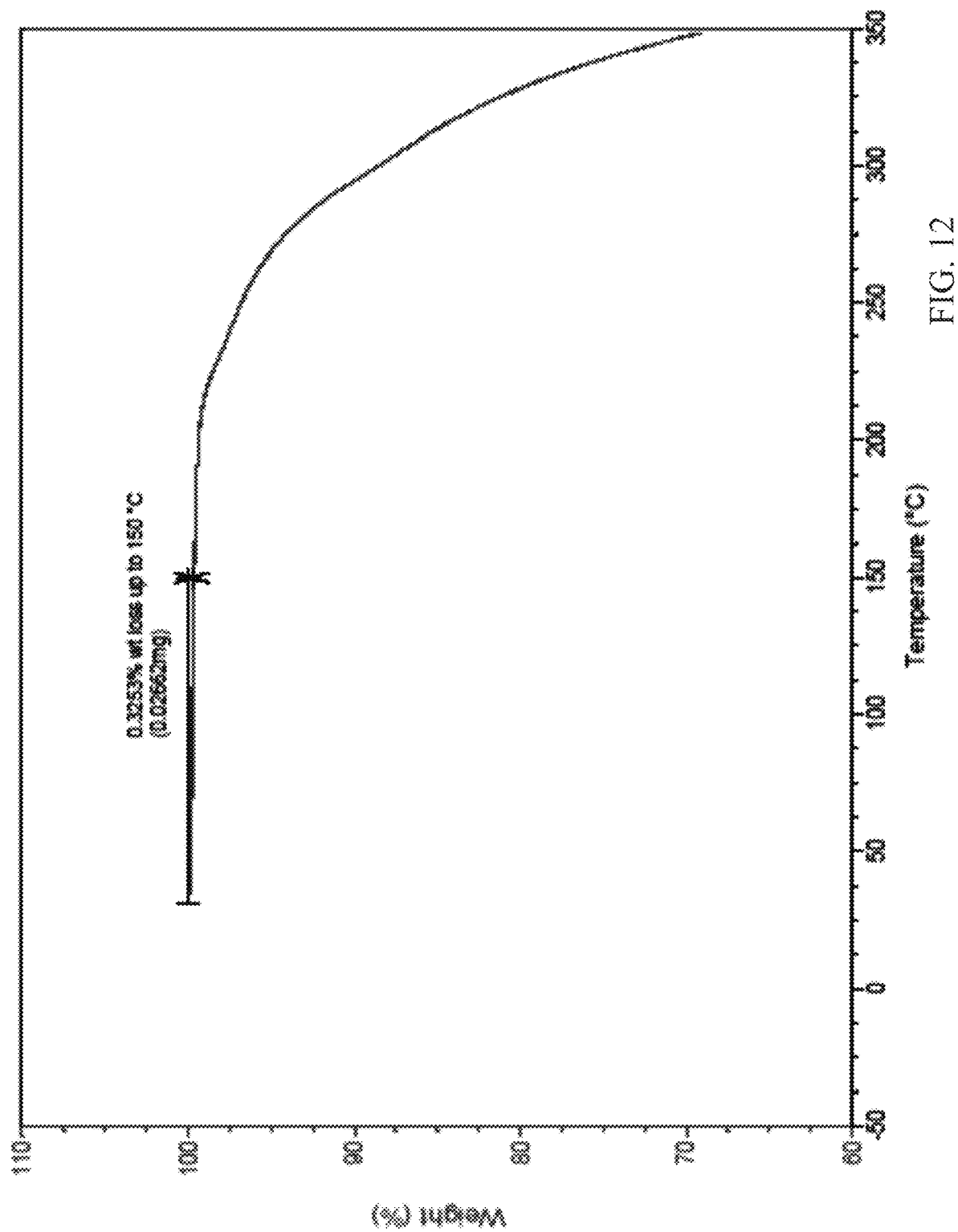
FIG. 12 is thermogravimetric analysis (TGA) of Compound I Form C.

In some embodiments, Form C is also characterized by thermogravimetric analysis (TGA) comprising a thermogram substantially as shown in FIG. 12.

Figure 13:
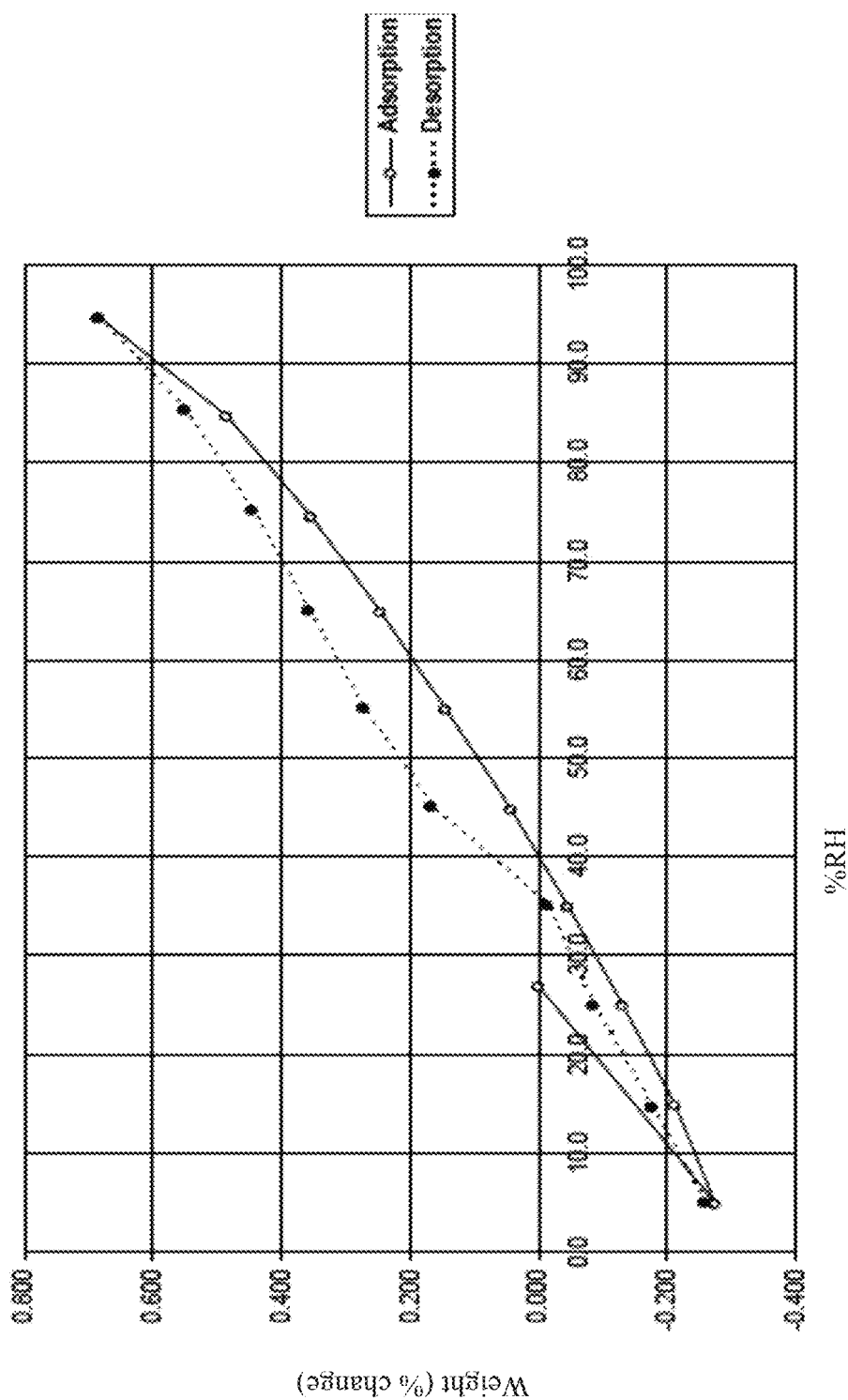
FIG. 13 is dynamic vapor sorption (DVS) curve of Compound I Form C.

In some embodiments, Form C is also characterized by a dynamic vapor sorption (DVS) curve substantially as shown in FIG. 13.

Figure 14:
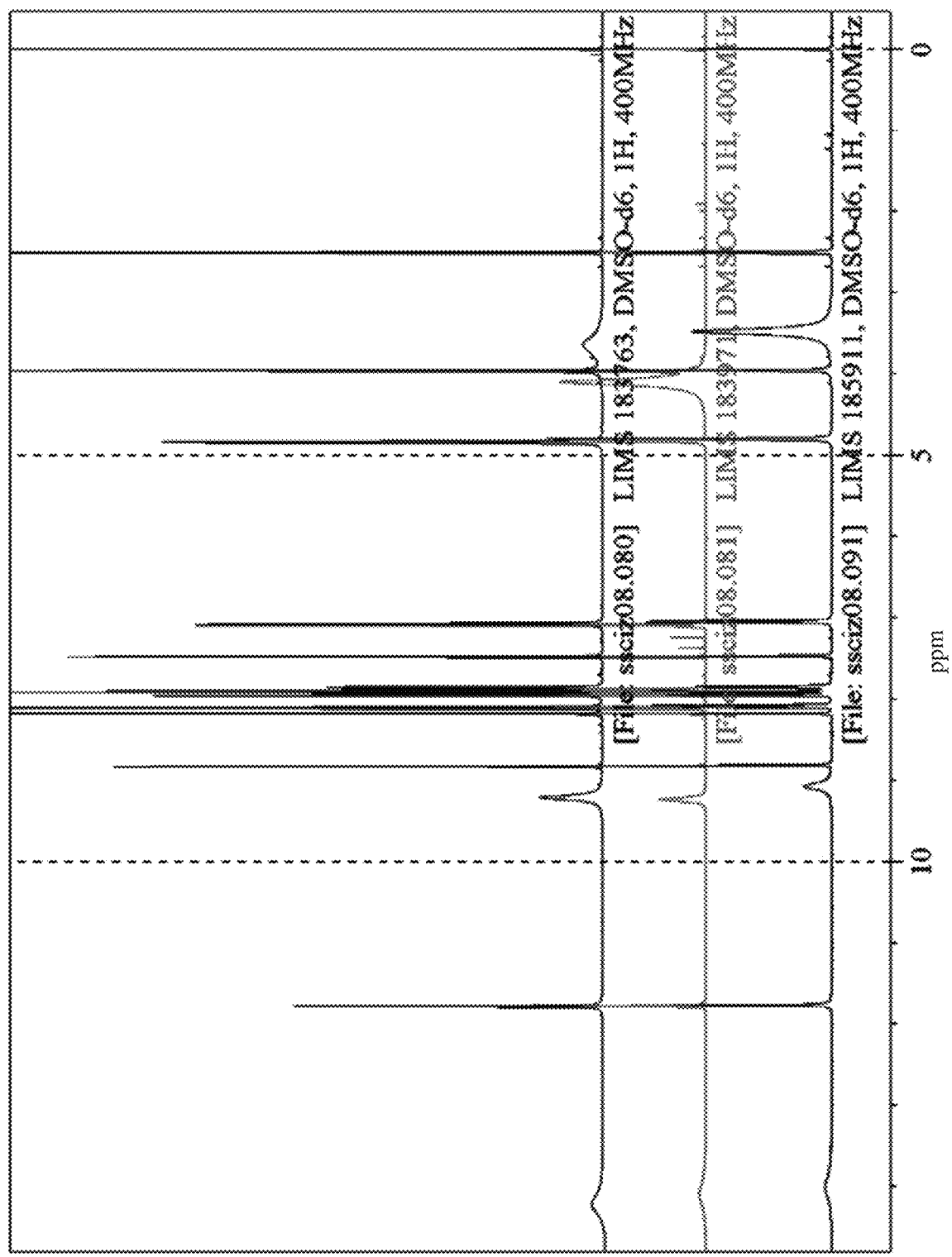
FIG. 14 is a nuclear magnetic resonance spectra ($^1$H NMR) of Compound I Forms A-C (from top to bottom).

In some embodiments, Compound I Forms A-C (from top to bottom) are also characterized by their nuclear magnetic resonance spectra ($^1$H NMR) as shown in FIG. 14.

In another embodiment, this disclosure provides a process of preparing Compound I Form D comprising recrystallizing Compound I Form A from a mixture of acetone and methanol.

Compound I Form D is characterized by an X-ray powder diffractogram comprising peaks (±0.2°) at 6.9, 20.9 and 26.7° 2θ, as determined on a diffractometer using Cu-Kα radiation. The diffractogram comprises additional peaks (±0.2°) at 12.9 and 24.0° 2θ. Form D is also characterized by its full X-ray powder diffractogram as substantially shown in FIG. 17. Major peaks in the XRPD pattern are shown in Table 4 below. In one embodiment, this disclosure provides Compound I Form D comprising two or more peaks (±0.2°) listed in the Table 4 below as determined on a diffractometer using Cu-Kα radiation.

Figure 23:
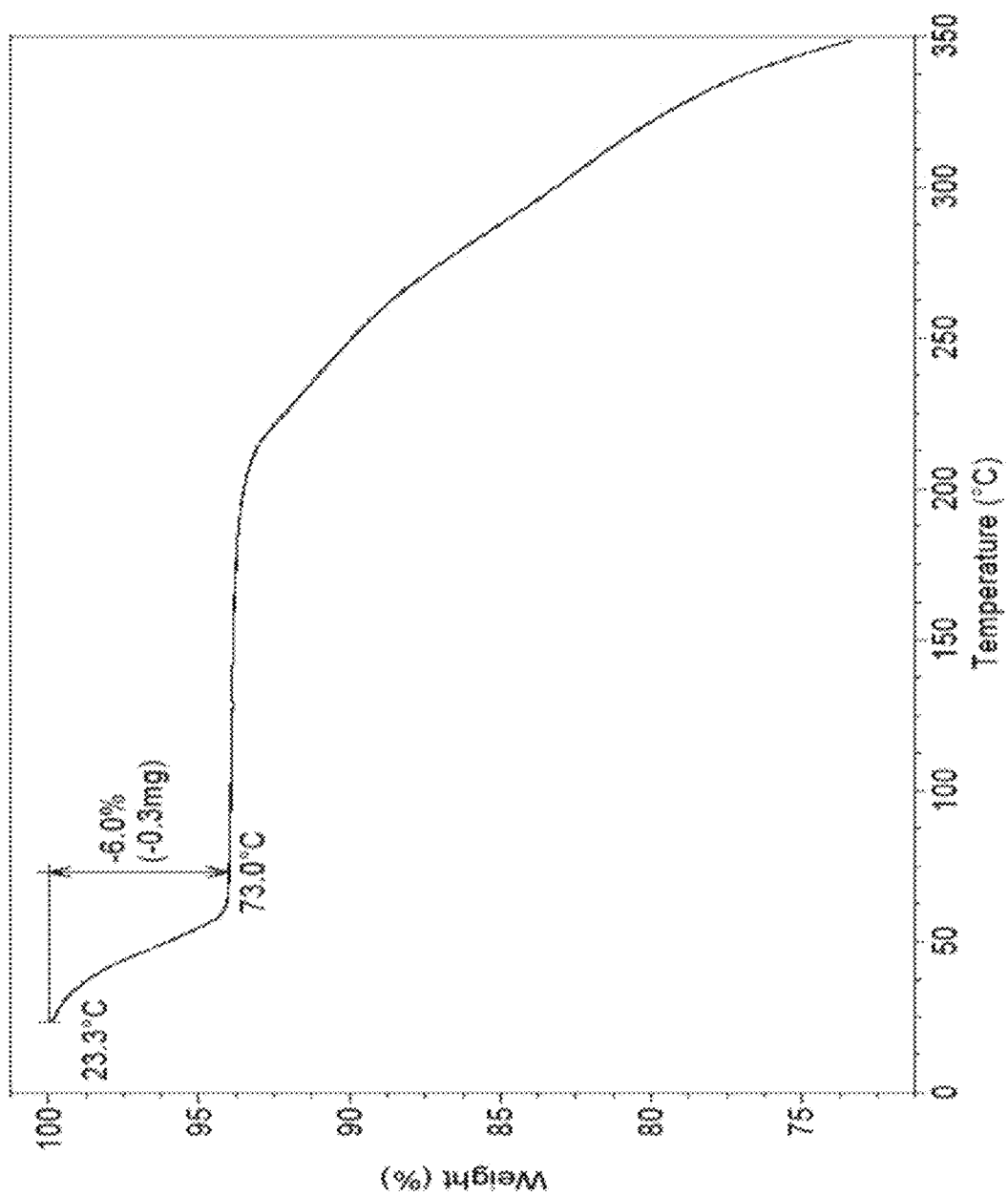
FIG. 23 is thermogravimetric analysis (TGA) of Compound I Form D.

In some embodiments, Form D is also characterized by thermogravimetric analysis (TGA) comprising a thermogram substantially as shown in FIG. 23.

TABLE 4

Major Peaks in the XRPD Pattern for Compound I Form D

| °2θ (±0.2°) | d-space [Å] |
|---|---|
| 6.90 | 12.809 ± 0.371 |
| 12.91 | 6.854 ± 0.106 |
| 16.21 | 5.463 ± 0.067 |
| 19.52 | 4.545 ± 0.046 |
| 20.91 | 4.245 ± 0.040 |
| 22.07 | 4.024 ± 0.036 |
| 23.96 | 3.710 ± 0.031 |
| 25.22 | 3.529 ± 0.028 |
| 26.73 | 3.332 ± 0.024 |
| 28.62 | 3.117 ± 0.021 |

Crystalline Form of Compound II

Figure 20:
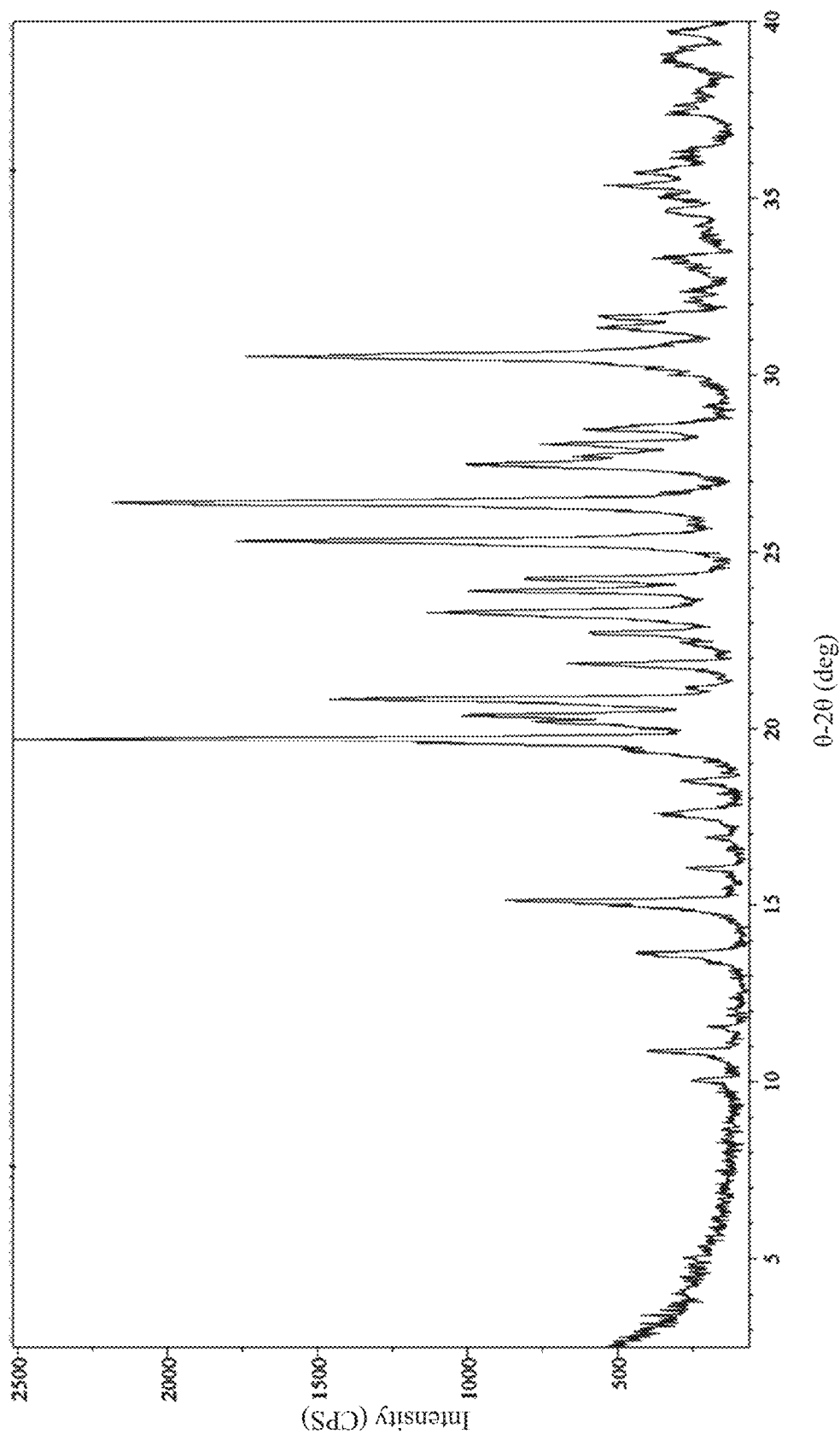
FIG. 20 is X-ray powder diffraction pattern of crystalline Compound II.

Compound II is characterized by an X-ray powder diffractogram comprising peaks) (±0.2° at 10.9, 19.7 and 26.4° 2θ, as determined on a diffractometer using Cu-Kα radiation. The diffractogram comprises additional peaks (±0.2°) at 20.8 and 25.3° 2θ. The free base is also characterized by its full X-ray powder diffractogram as substantially shown in FIG. 20. Major peaks in the XRPD pattern are shown in Table 5 below. In one embodiment, this disclosure provides a crystalline Compound II comprising two or more peaks (±0.2°) listed in the Table 5 below as determined on a diffractometer using Cu-Kα radiation.

TABLE 5

Major Peaks in the XRPD Pattern for Compound II

| °2θ (±0.2°) | d-space [Å] |
|---|---|
| 10.9 | 8.128 ± 0.149 |
| 13.6 | 6.500 ± 0.095 |
| 15.1 | 5.854 ± 0.077 |
| 17.6 | 5.043 ± 0.057 |
| 19.7 | 4.499 ± 0.045 |
| 20.2 | 4.391 ± 0.043 |
| 20.4 | 4.354 ± 0.042 |
| 20.8 | 4.259 ± 0.040 |
| 21.8 | 4.066 ± 0.037 |
| 22.7 | 3.912 ± 0.034 |
| 23.3 | 3.816 ± 0.032 |
| 23.9 | 3.719 ± 0.031 |
| 24.3 | 3.667 ± 0.030 |
| 25.3 | 3.515 ± 0.027 |
| 26.4 | 3.374 ± 0.025 |
| 27.5 | 3.243 ± 0.023 |
| 27.7 | 3.214 ± 0.023 |
| 28.1 | 3.178 ± 0.022 |
| 28.5 | 3.133 ± 0.022 |

Characterization of Crystalline Forms A-D of Compound I and Crystalline Compound II Compound I Form A Form A is unsolvated. Form A was obtained as described in Example 1 and was utilized as the source material for the polymorph screen. Form A was also obtained from the desolvation of Form D, which is a methanol solvate, under mild heating conditions.

The approximate solubility of Form A was calculated in a variety of solvents using the Solvent Addition Method discussed in the Examples and the results are as shown below.

| Approximate Solubility of Compound I Form A. | |
|---|---|
| Solvent | Solubility (mg/mL)[1] |
| Acetone | <2 |
| Acetonitrile (ACN) | <2 |
| Dichloromethane (DCM) | <2 |
| 1,4-Dioxane | <2 |
| Dimethyl Formamide (DMF) | >145 |
| Dimethyl Sulfoxide (DMSO) | >153 |
| Ethanol (EtOH) | 5 |
| Ethyl Acetate (EtOAc) | <2 |
| Heptane | <2 |
| Isopropyl alcohol (IPA) | 2 |
| Methanol (MeOH) | 31 |
| Methyl tert-Butyl Ether (MTBE) | <2 |
| Tetrahydrofuran (THF) | <2 |
| Toluene | <2 |
| Water | <2 |

[1]Solubilities are calculated based on the total solvent used to give a solution; actual solubilities may be greater because of the volume of the solvent portions utilized or a slow rate of dissolution. Solubilities are rounded to the nearest mg/mL.

The thermograms of the Form A are displayed in FIG. 2 and FIG. 3. The DSC curve exhibits a melt and concurrent decomposition endotherm with an onset temperature at 222° C. (signal maximum at 231° C.). A minor endotherm is also observed at about 76° C. This event is likely related to a phase transition based on physical stability and hotstage microscopy data. The TG curve exhibits a negligible weight loss up to 150° C., suggesting that it is not solvated. Weight loss above this temperature is due to decomposition.

These thermal events were investigated by hotstage microscopy. The material exhibits birefringence and extinction, typical for crystalline material. A change in birefringence was observed near 65° C. (consistent with the minor endotherm in the DSC above) followed by two distinct melt onsets (184 and 196° C.). These events suggest that a partial phase transformation occurred upon heating, resulting in a mixture of two forms, each with a distinct melt.

The physical stability of Form A was investigated in order to support the hotstage microscopy observations and the results are shown in the table below.

| Conditions | Description | XRPD Result |
|---|---|---|
| 80° C./7 d (<<100 mg) | White solid | C |
| 80° C./4 d (>100 mg) | Off-white solid | A |
| 80° C./4 d (8 d consecutive, >100 mg) | Off-white solid | A |
| RT/85% RH/14 d | White solid | A + minor C |
| 40° C./75% RH/14 d | White solid | A + C |

A small sample of Form A (<<100 mg) converted to Form C (unsolvated form) upon exposure to 80° C. for 7 days. A partial conversion to Form C was obtained when Form A was exposed to elevated humidity. In addition, complete conversion to Form C was obtained when Form A was slurried in ethanol for 21 days. This indicates that Form A is physically metastable (at the conditions investigated) and will undergo a phase transition to Form C.

The DVS isotherm suggests that Form A is hygroscopic (FIG. 4). During the sorption step, the material exhibits a weight gain of 0.6% from 5% to 75% RH and an additional 1.7% weight above 75% RH. Minor hysteresis was observed upon desorption. The resulting sample was Form A, by XRPD.

The $^1$H NMR spectrum is consistent with the structure of Compound I (FIG. 14, top one). Peaks at approximately 2.5 and 3.6 ppm are assigned to deuterated DMSO (due to residual protons in the NMR solvent) and water, respectively.

Raman and IR spectra (FIG. 5 and FIG. 15, respectively) of Form A were obtained for comparison with that of Form B. The spectra for each exhibit a flat baseline with generally well resolved and sharp bands. Differences within the Raman spectra between the forms were negligible. However, there are differences in intensities and band positions between the IR spectra, indicating that there are chemical and/or physical differences between the forms. Several obvious IR differences in intensities and band positions were noted at approximately 3500-2600 $cm^{-1}$, 1645 $cm^{-1}$, and 1110 $cm^{-1}$.

Thus, Form A is unsolvated. It is hygroscopic above 75% RH. Form A is physically metastable (at the conditions investigated) and can convert to Form C.

Compound I Form B

Form B was obtained as described in Example 2 and was utilized for an analytical comparison with other forms.

Figure 18:
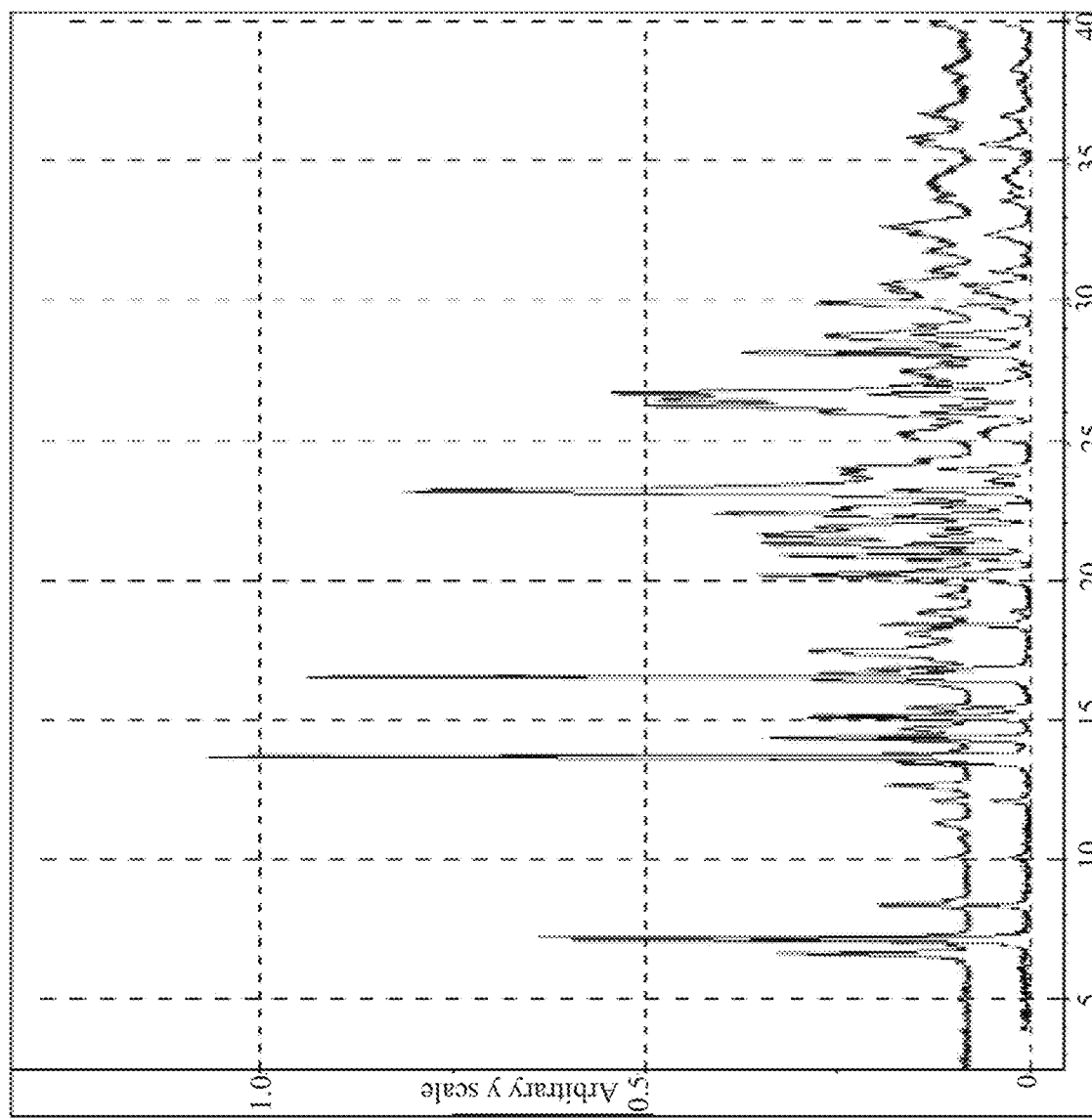
FIG. 18 is X-ray powder diffraction pattern comparison of Compound I Form B and Compound I Form C (from top to bottom).

The XRPD of Form B contains all the X-ray reflections observed in the pattern of Form C, as well as additional reflections. A comparison of both patterns is shown in FIG. 18. This suggests that Form B is a two phase mixture comprised of Form C (unsolvated form) and a hydrated form based on the characterization described below.

The thermograms of Form B are displayed in FIG. 7 and FIG. 8. The DSC curve exhibits a broad desolvation endotherm (with shoulder) with a signal maximum at 127° C. This event is associated with a TG weight loss of approximately 6.0% (up to 150° C.). Assuming this is due to the volatilization of water (no other solvents were identified by NMR), the weight loss corresponds to 1.5 moles of water for every mole of Compound I. Karl Fischer analysis indicates the material contains 3.45% water by weight. (The water content discrepancy between techniques may be due to losses upon ambient storage. While this explanation has not been confirmed, the KF analysis was performed 14 days after the TG analysis.) In the DSC curve, a minor exotherm and endotherm are also observed at 187 and 203° C., respectively. These events are likely related to a phase transition, based on physical stability and hotstage microscopy data (see below). A sharp endotherm with an onset temperature of 226° C. (signal maximum at 233° C.) is due to the melt and concurrent decomposition. Significant decomposition weight losses are observed at this temperature by TG.

These thermal events were investigated by hotstage microscopy. The material exhibits birefringence and extinction. A loss of birefringence and a solid to liquid transition was observed between about 70 and about 130° C., consistent with the desolvation event described by the TG and DSC thermograms above. Recrystallization was observed near 142° C. and was followed by a melt between about 192° C. and about 200° C.

The physical stability of Form B was investigated in order to support the hotstage microscopy observations. Desolvation/conversion to Form C (unsolvated form) was obtained by exposing Form B to about 150° C. for about 5 minutes.

The $^1$H NMR spectrum is consistent with the structure of Compound I (FIG. 14, middle one). Minor peaks at approximately 7.1, 7.25, and 7.38 ppm were not identified. Peaks at approximately 2.5 and 4.1 ppm are assigned to deuterated DMSO (due to residual protons in the NMR solvent) and water, respectively.

Raman and IR spectra (FIG. 9 and FIG. 16, respectively) of Form B were obtained for comparison with that of Form A (unsolvated). The spectra for each exhibit a flat baseline with generally well resolved and sharp bands. Differences within the Raman spectra between the forms were negligible. However, there are differences in intensities and band positions between the IR spectra, indicating that there are chemical and/or physical differences between the forms. Several obvious IR differences in intensities and band positions were noted at approximately 3500-2600 $cm^-$, 1645 $cm^{-1}$, and 1110 $cm^-$.

Thus, based on XRPD, Form B is a two phase mixture comprised of Form C and an unidentified hydrated form. Desolvation/conversion of Form B to Form C was obtained by exposing the material to about 150° C. for about 5 minutes.

Compound I Form C

Form C is unsolvated. Form C was obtained from a wide variety of experiments as discussed in Example 3 and, consequently, was the most frequently observed form. It was crystallized directly out of ethanol by a crash cool experiment, obtained from thermal conversion of Form A, and through the desolvation of Form B or Form D.

The thermograms of Form C are displayed in FIG. 11 and FIG. 12. The DSC curve exhibits a sharp endotherm, indicative of a melt, with an onset temperature at about 227° C. (signal maximum at 234° C.). The TG curve exhibits a negligible weight loss up to the melt endotherm, suggesting that the material is not solvated. Significant weight loss at and above this temperature indicate that decomposition occurs concurrently with the melt.

The DVS isotherm suggests that Form C is less hygroscopic than Form A (FIG. 13). During the sorption step, the material exhibits a weight gain of only 0.96% from 5% to 95% RH. Minor hysteresis was observed upon desorption. The resulting sample remained unchanged by XRPD.

Form C is more physically stable than Form A. As discussed above, Form C was obtained through the conversion of Form A by exposure to elevated temperature or humidity. In addition, a complete conversion to Form C was obtained when Form A was slurried in ethanol for 21 days (Example 3). This indicates that Form A is physically metastable and will undergo a solid state phase transition to Form C.

The $^1$H NMR spectrum is consistent with the structure of Compound I (FIG. 14, bottom one). Peaks at approximately 2.5 and 3.6 ppm are assigned to deuterated DMSO (due to residual protons in the NMR solvent) and water, respectively.

Thus, Form C is an unsolvated form that melts concurrently with decomposition at about 227° C. It is less hygroscopic than Form A. Form C is the physically stable unsolvated form.

Compound I Form D

Form D appears to be a methanol solvate. It was crystallized directly out of (88:12) acetone/MeOH by a slow cool experiment (Example 3). It was also obtained by exposing Form A to methanol vapor.

The DSC scan of Form D displays a broad endotherm with a peak maximum at approximately 70° C. that suggests loss of volatile components. Form D also exhibited approximately 5.3% weight loss upon equilibration at 5% RH, confirming that the material contained at least that amount of volatile easily removed at low RH conditions. During the sorption/desorption phases of the experiment, the sample exhibited negligible weight gain (0.9%)/loss (0.9%), similar to the isotherm observed for Form C. The TG curve exhibits about 6% weight loss up to 73° C.

The physical stability of Form D was investigated. The form desolvated to Form A upon exposure to 80° C. for 15 minutes. The material then converted to Form C upon continued exposure to 80° C. for 2 days.

Thus, based on the method of preparation and previous characterization data, Form D appears to be a methanol solvate. The form desolvates to Forms A or C upon exposure to elevated temperatures.

Compound I Amorphous

Figure 19:
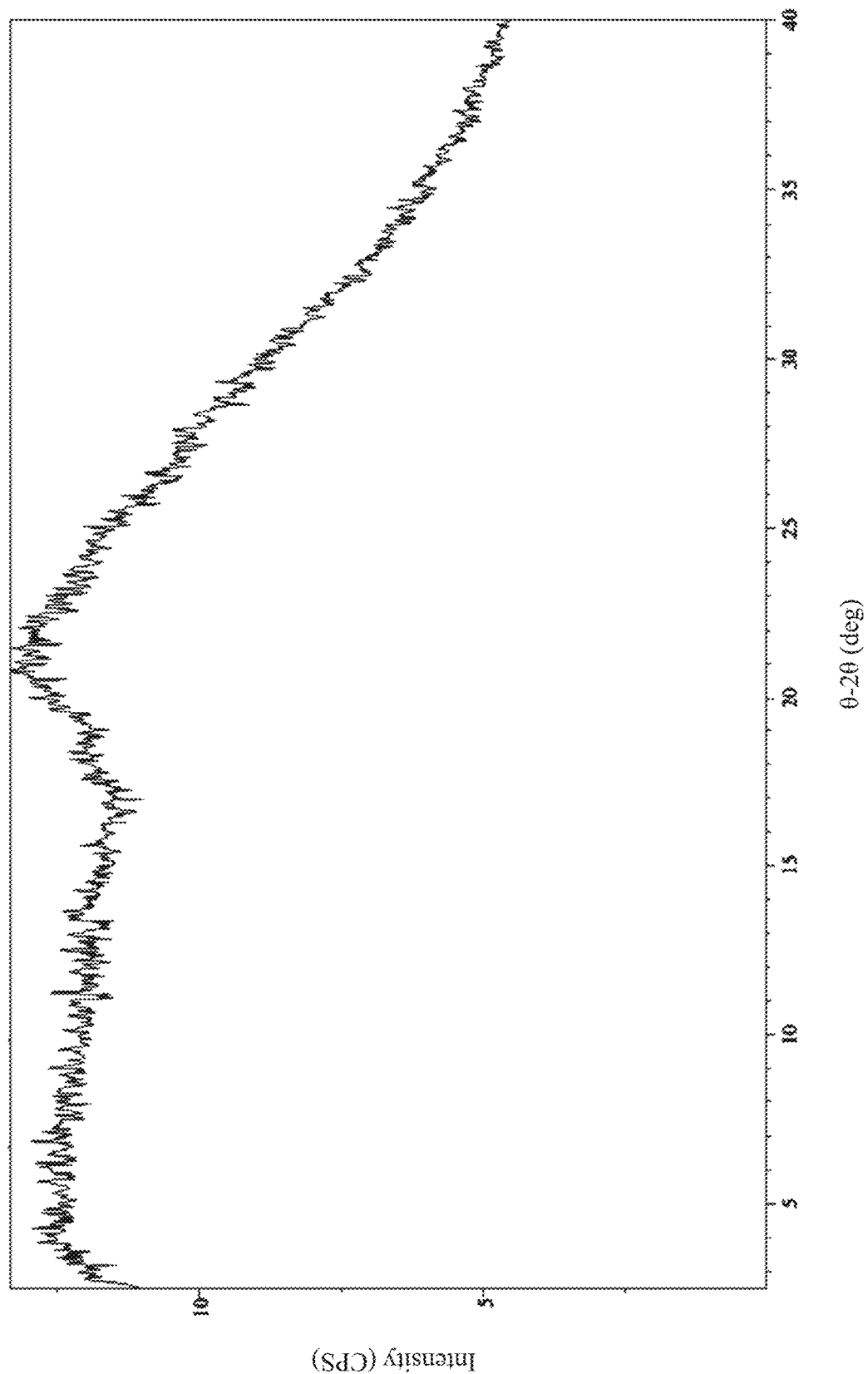
FIG. 19 is X-ray powder diffraction pattern of compound I amorphous.

Compound I amorphous was isolated through rotary evaporation from trifluroethanol. It was obtained by dissolving 20 mg of Compound I Form A in 100 µL of trifluoroethanol and rotary evaporation at 60° C. for 7 minutes provided the amorphous form as a white solid. The XRPD indicates amorphous material (FIG. 19).

Compound II

Compound II was prepared by the synthetic method above and the resulting crystals were characterized.

Figure 21:
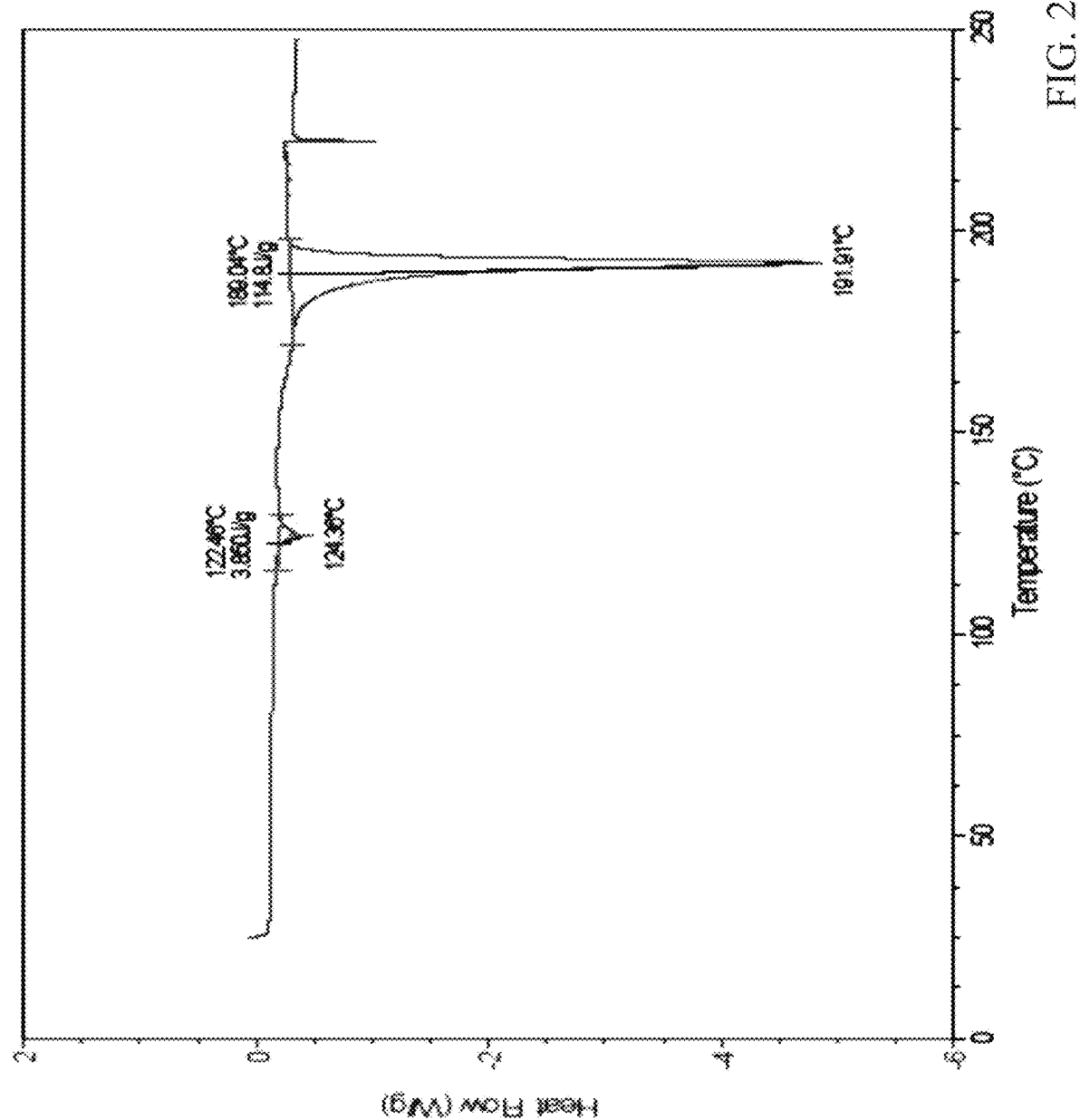
FIG. 21 is differential scanning calorimetry (DSC) curve of crystalline Compound II.

The DSC thermogram of free base is displayed in FIG. 21. The DSC curve displays a small endotherm at approximately 124° C. with a larger endotherm at approximately 192° C. that is consistent with sample melting.

Figure 22:
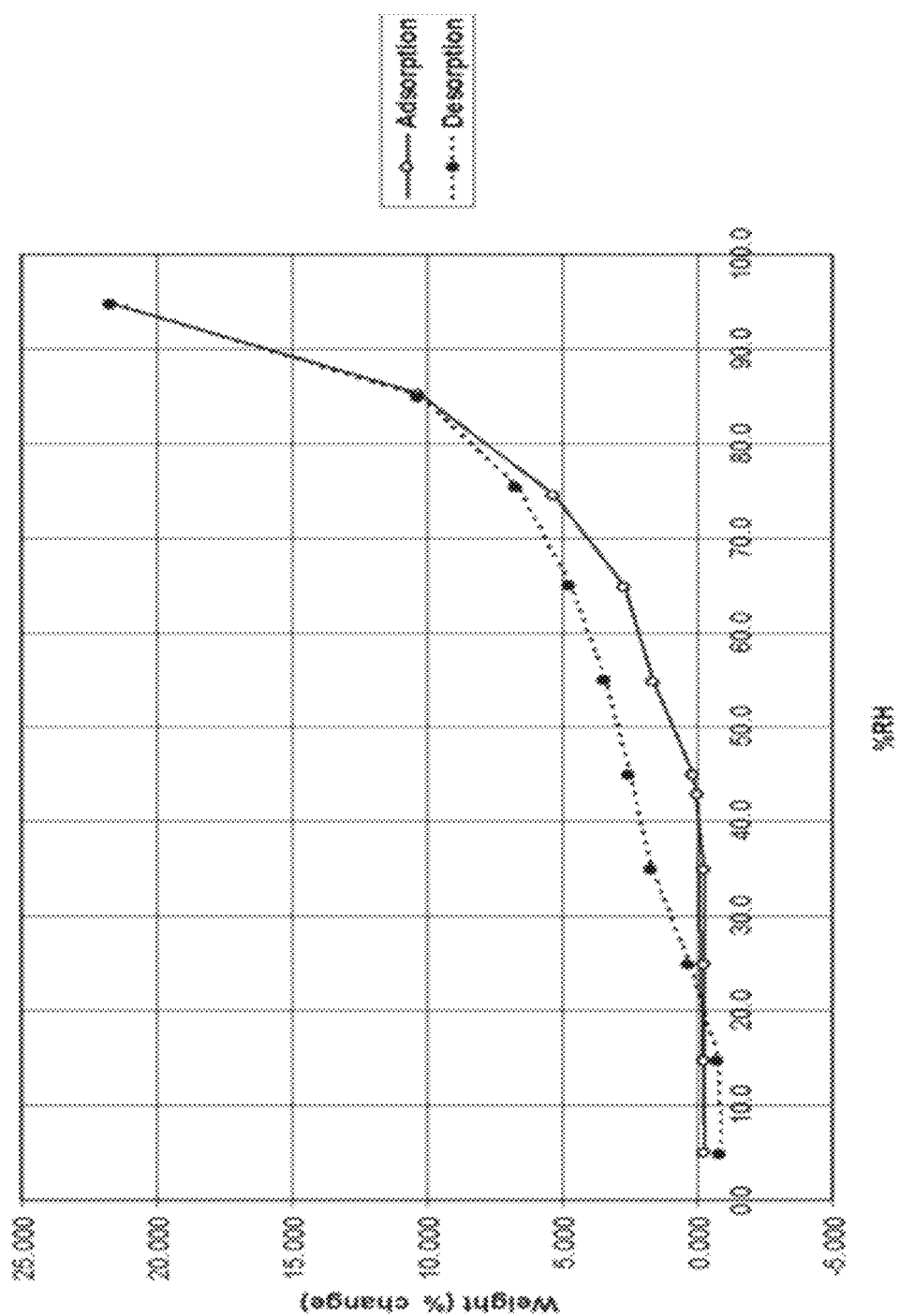
FIG. 22 is dynamic vapor sorption (DVS) curve of crystalline Compound II.

DVS results indicate 0.3-0.4% weight loss upon equilibration at 5% RH (FIG. 22). Results for the freebase show that the majority of the weight gained (~21.6%) is from 45% to 95% RH. The sample subsequently loses all weight gained during the desorption phase. The free base appears to be hygroscopic.

Light microscopy observations were made. The free base exhibits birefringence with extinction when the microscope stage is rotated. Additionally, it exhibits flow when pressure is applied to the cover glass, suggesting that the material is a mesophase or a condis crystal. Images of the free base show bladed-micaceous particles.

Salts of Compound II

In addition to the hydrochloride salt (Compound I), several other salts can be prepared for the free base (Compound II). In some embodiments, the salt is selected from acetate, besylate, bromide, calcium, citrate, decanoate/caprate, dimeglumine, dipropionate, fumarate, lactate, maleate, meglumine, mesylate, nitrate, pamoate, phosphate, potassium, sodium, succinate, sulfate, tartrate and trometamol. In other embodiment, the salt is selected from acetonide, aspartate, axetil, benzoate, butoxide, butyrate, camsylate, carbonate, cypionate, dimethyl sulfoxide, disoproxil, edisylate, enanthate, epolamine, erbumine, estolate, etabonate, etexilate, ethanolate, ethylsuccinate, fenofibrate, fosamil, furoate, gluconate, hexacetonide, hippurate, bromide/hydrobromide, iodide, isethionate, lysine, magnesium, malate, medoxomil, methylbromide, napsylate, olamine, oleate, oxalate, oxyquinoline, palmitate, pentanoate, peroxide, pivalate, pivoxil, polacrilex, polistirex, polylysine, polystyrate, probutate, proxetil, saccharate, stearate, subcitrate, subsalicylate, sulfadiazine, sulfonate, tosylate, triflate, valerate, xinafoate, and zinc. Each of the above-mentioned salts is prepared by methods known to one of skill in the art.

Compositions

In one embodiment, this disclosure provides a composition comprising a compound of this disclosure and a pharmaceutically acceptable carrier or excipient. In another embodiment, the compound is selected from Compound I Form A, Compound I Form B, Compound I Form C Compound I Form D and crystalline Compound II.

In one embodiment, this disclosure provides a composition comprising two or more compounds selected from the group consisting of Compound I Form A, Compound I Form B, Compound I Form C and Compound I Form D as described herein.

In another embodiment, the composition comprises Compound I Form A and Compound I Form C. In another embodiment, the composition comprises Compound I Form A and at least 10%, 15%, 20%, 25%, 30%, 35%, 40%, 45%, 50%, 55%, 60%, 65%, 70%, 75%, 80%, 85%, 90%, or 95% w/w of Compound I Form C. In yet another embodiment, the composition comprises Compound I Form A and at least 50% of w/w of Compound I Form C.

In another embodiment, the composition comprises Compound I Form B and Compound I Form C. In another embodiment, the composition comprises Compound I Form B and at least 10%, 15%, 20%, 25%, 30%, 35%, 40%, 45%, 50%, 55%, 60%, 65%, 70%, 75%, 80%, 85%, 90%, or 95% w/w of Compound I Form C. In yet another embodiment, the composition comprises Compound I Form B and at least 50% w/w of Compound I Form C.

Formulations and Administration

The methods and compounds will typically be used in therapy for human subjects. However, they may also be used to treat similar or identical indications in other animal subjects. Compounds described herein can be administered by different routes, including injection (i.e. parenteral, including intravenous, intraperitoneal, subcutaneous, and intramuscular), oral, transdermal, transmucosal, rectal, or inhalant. Such dosage forms should allow the compound to reach target cells. Other factors are well known in the art, and include considerations such as toxicity and dosage forms that retard the compound or composition from exerting its effects. Techniques and formulations generally may be found in Remington: The Science and Practice of Pharmacy, 21st edition, Lippincott, Williams and Wilkins, Philadelphia, Pa., 2005 (hereby incorporated by reference herein).

In some embodiments, compositions used in the methods of the present disclosure will comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium tri silicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-delta-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, di-fatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, and the like.

In some embodiments, oral administration may be used. Pharmaceutical preparations for oral use can be formulated into conventional oral dosage forms such as capsules, tablets, and liquid preparations such as syrups, elixirs, and concentrated drops. Compounds described herein may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone); oily excipients, including vegetable and animal oils, such as sunflower oil, olive oil, or codliver oil. The oral dosage formulations may also contain disintegrating agents, such as the cross-linked polyvinylpyrrolidone, agar, or alginic acid, or a salt thereof such as sodium alginate; a lubricant, such as talc or magnesium stearate; a plasticizer, such as glycerol or sorbitol; a sweetening such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations. Also provided are dragee cores with suitable coatings. For this purpose, concentrated sugar solutions may be used, which may optionally contain, for example, gum arabic, talc, poly-vinylpyrrolidone, carbopol gel, polyethylene glycol, and/or titanium dioxide, lacquer solutions, and suitable organic solvents or solvent mixtures.

In some embodiments, the formulation comprises a tablet or a capsule. In one embodiment, this disclosure provides a tablet comprising a compound of this disclosure and a pharmaceutically acceptable carrier or excipient. In another embodiment, the compound is selected from Compound I Form A, Compound I Form B, Compound I Form C, Compound I Form D and crystalline Compound II. In another embodiment, this disclosure provides a capsule comprising a compound of this disclosure and a pharmaceutically acceptable carrier or excipient. In a further embodiment, the compound is selected from Compound I Form A, Compound I Form B, Compound I Form C, Compound I Form D and crystalline Compound II.

In one embodiment, this disclosure provides a tablet comprising Compound I Form C and a pharmaceutically acceptable carrier or excipient. In some embodiments, the tablet comprises at least 10%, 15%, 20%, 25%, 30%, 35%, 40%, 45%, 50%, 55%, 60%, 65%, 70%, 75%, 80%, 85%, 90%, or 95% w/w of Compound I Form C.

In one embodiment, this disclosure provides a capsule comprising Compound I Form C and a pharmaceutically acceptable carrier or excipient. In some embodiments, the capsule comprises at least 10%, 15%, 20%, 25%, 30%, 35%, 40%, 45%, 50%, 55%, 60%, 65%, 70%, 75%, 80%, 85%, 90%, or 95% w/w of Compound I Form C.

In another embodiment, this disclosure provides a process of making a tablet or a capsule comprising combining a compound of this disclosure and a pharmaceutically acceptable carrier or excipient. In another embodiment, this disclosure provides a process of making a tablet comprising Compound I Form C by combining Compound I Form C with a pharmaceutically acceptable carrier or excipient. In another embodiment, this disclosure provides a process of making a capsule comprising Compound I Form C by combining Compound I Form C with a pharmaceutically acceptable carrier or excipient.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Compounds described herein for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, the compounds may be formulated in solid form, including, for example, lyophilized forms, and redissolved or suspended prior to use.

In some embodiments, transmucosal, topical or transdermal administration may be used. In such formulations of compounds described herein, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of compounds described herein for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than C12). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, compounds are administered as inhalants. Compounds described herein may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds described herein may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of various compounds to be administered can be determined by standard procedures taking into account factors such as the compound activity (in vitro, e.g. the Compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose is in the range of about 0.01 to 50 mg/kg, also about 0.1 to 20 mg/kg of the subject being treated. Typically, a dose of about 600 to 1200 mg/day is used. Multiple doses may be used.

The compounds described herein may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the disclosure or other therapeutics used in combination, e.g., reduction in the amount dosed relative to a compound or therapy used alone, by methods well known to those of ordinary skill in the art.

The compounds described herein may be used in combination with another chemotherapeutic agent or drug or a kinase inhibitor for treating the same disease. Such combination can be a fixed dose composition or be administered at different times, or co-administration of the compound and anther agent, drug or kinase inhibitor simultaneously or separately. In some embodiments, dosage may be modified for one or more of the compounds of the disclosure or another agent, drug or kinase inhibitor used in combination, e.g., reduction or increase in the amount dosed relative to a compound used alone to improve safety and/or efficacy, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound described herein, or at the same time as a compound described herein. Use in combination also includes use with a therapy or medical procedure that is administered once or infrequently, such as surgery, along with a compound described herein administered within a short time or longer time before or after the other therapy or procedure. In some embodiments, the present disclosure provides for delivery of a compound described herein and one or more other drug therapeutics delivered by a different route of administration or by the same route of administration. The use in combination for any route of administration includes delivery of a compound described herein and one or more other drug therapeutics delivered by the same route of administration together in any formulation, including formulations where the two compounds are chemically linked in such a way that they maintain their therapeutic activity when administered. In one aspect, the other drug therapy may be co-administered with a compound described herein. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound described herein and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

Methods of Treatment

In some embodiments, the disclosure provides a method for treating a disease or condition in a subject in need thereof, by administering to the subject a therapeutically effective amount one or more solid, crystalline or polymorphs of Compound I or solid or crystalline forms of Compound II, as described herein, or a composition thereof. Examples of Crystalline forms that can be used in the methods described herein include Compound I Form A, Compound I Form B, Compound I Form C, Compound I Form D, and crystalline Compound II.

In some embodiments, the disclosure provides a method of treating a disease or condition in a subject in need thereof, by administering to the subject a therapeutically effective amount of one or more solid, crystalline or polymorphs of Compound I or solid or crystalline Compound II as described herein, a prodrug of such compound, a pharmaceutically acceptable salt of such compound or prodrug, or a pharmaceutically acceptable formulation of such compound or prodrug in combination with one or more other suitable therapies for the disease or condition.

In some embodiments, the disclosure provides a method for treating a subject suffering from or at risk of a disease or condition mediated by c-Fms, c-Kit, Flt3, infiltration or activation of macrophages and/or microglias or combinations thereof. The method includes administering to the subject an effective amount of one or more solid, crystalline or polymorphs of Compound I or solid or crystalline Compound II as described herein, or a composition as described herein. In some embodiments, the method includes administering to the subject a therapeutically effective amount of Compound I Form A, Compound I Form B, Compound I Form C, Compound I Form D or crystalline Compound II. In some embodiments, the method includes administering to the subject a composition comprising a therapeutically effective amount of Compound I Form A, Compound I Form B, Compound I Form C, Compound I Form D or crystalline Compound II and a pharmaceutically acceptable excipient.

In certain embodiments, the method involves administering to the subject an effective amount of one or more solid, crystalline or polymorphs of Compound I or solid or crystalline Compound II as described herein in combination with one or more other suitable therapies for the disease or condition. In some embodiments, the disclosure provides a method for treating a subject suffering from a disease or condition mediated by tumor-associated macrophages (TAM). In certain embodiments, the disclosure provides a method for treating a subject suffering from a disease or condition, such as a tumor, where tumor-associated macrophages play a role in tumor proliferation, survival, and metastasis. In some embodiments, the disclosure provides a method for treating a subject suffering from a disease or condition, where reduction/depletion of macrophages or microglia provides a benefit. In certain instances, the disease or condition is as described herein. The method includes administering to the subject an effective amount of one or more solid, crystalline or polymorphs of Compound I or solid or crystalline Compound II as described herein and an agent or a drug as described herein. In some embodiments, the disclosure provides methods for treating a subject suffering from tumors that express aberrantly or otherwise Fms, CSF1R, CSF1 or IL-34, or activating mutations or translocations of any of the foregoing.

In some embodiments, the diseases treatable with one or more solid, crystalline or polymorphs of Compound I or solid or crystalline Compound II as described herein or compositions as described herein are c-Fms mediated disease selected from the group consisting of immune disorders, including, but not limiting to, rheumatoid arthritis, systemic lupus erythematosus (SLE), and transplant rejection; stem cell ablation and myelopreparation for stem cell transplant; inflammatory diseases including, but not limited to, osteoarthritis, inflammatory bowel syndrome, ulcerative colitis, Crohn's disease, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, increased risk of fracture, Paget's disease, hypercalcemia, infection-mediated osteolysis (e.g. osteomyelitis), peri-prosthetic or wear-debris-mediated osteolysis, and metastasis of cancer to bone; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the central nervous system, including, but not limited to, multiple sclerosis, stroke, Alzheimer's disease and Parkinson's disease; inflammatory and chronic pain, including, but not limited to, bone pain; and cancers, including, but not limited to, multiple myeloma, acute myeloid leukemia (AML), chronic myeloid leukemia (CML), monocytic leukemia, prostate cancer, breast cancer, ovarian cancer, melanoma, glioblastoma multiforme, tauopathies, metastasis of tumors to other tissues, and other chronic myeloproliferative diseases such as myelofibrosis. In some embodiments, the AML is associated with Fms-like tyrosine kinase 3 (Flt3) mutations that are internal tandem duplication (ITD) mutations. In some embodiments, the c-Fms mediated diseases include tumors that express aberrantly or otherwise Fms, CSF1R, CSF1 or IL-34, or activating mutations or translocations of any of the foregoing.

In other embodiments, the disease or condition is mediated by c-Fms and c-Kit and is selected from the group consisting of mast cell tumors, small cell lung cancer, testicular cancer, gastrointestinal stromal tumors, glioblastoma, astrocytoma, neuroblastoma, carcinomas of the female genital tract, sarcomas of neuroectodermal origin, colorectal carcinoma, carcinoma in situ, Schwann cell neoplasia, malignant peripheral nerve cell tumors, malignant peripheral nerve sheath tumors, pheochromocytomas cutaneous and plexiform neurofibromas, neurofibromatosis, neurofibromatosis-1 (NF1), leiomyo-adenomatoid tumor, leiomyo sarcoma, acute myeloid leukemia, acute lymphocytic leukemia, chronic myelogenous leukemia, multiple myeloma, mastocytosis, melanoma, breast cancer, ovarian cancer, prostate cancer, canine mast cell tumors, metastasis of cancer to bone or other tissues, chronic myeloproliferative diseases such as myelofibrosis, renal hypertrophy, asthma, rheumatoid arthritis, allergic rhinitis, multiple sclerosis, osteoarthritis, inflammatory bowel syndrome, transplant rejection, systemic lupus erythematosis, ulcerative colitis, Crohn's disease, chronic obstructive pulmonary disease, emphysema, Kawasaki's Disease, hemophagocytic syndrome (macrophage activation syndrome), multicentric reticulohistiocytosis, atherosclerosis, Type I diabetes, Type II diabetes, insulin resistance, hyperglycemia, obesity, lipolysis, hypereosinophilia, osteoporosis, increased risk of fracture, Paget's disease, hypercalcemia, infection-mediated osteolysis (e.g. osteomyelitis), peri-prosthetic or wear-debris-mediated osteolysis, endometriosis, glomerulonephritis, interstitial nephritis, Lupus nephritis, tubular necrosis, diabetic nephropathy, stroke, Alzheimer's disease, Parkinson's disease, inflammatory pain, chronic pain, and bone pain.

In some embodiments, the disease or condition treatable with one or more solid, crystalline or polymorphs of Compound I or solid or crystalline Compound II or compositions as described herein is selected from alopecia, baldness, wound healing, androgenetic alopecia (AGA), epilepsy, traumatic brain injury, tauopathies, Erdheim Chester Disease, Langerhans cell histocytosis, hairy cell leukemia, non-small cell lung cancer, cleroderma, anterior eye disease, posterior eye disease, lysosomal storage disease, stem cell ablation and myelopreparation for stem cell transplant, primary progressive multiple sclerosis, complex regional pain syndrome, reflex sympathetic dystrophy, muscular dystrophy, duchenne muscular dystrophy, causalgia, neuro-inflammation, neuroinflammatory disorders, benign forgetfulness, HIV, binswager type dementia, dementia with lewy bodie, prosencephaly, microencepahy, cerebral palsy, congenital hydrocephalus, abdominal dropsy, progressive supranuclear palsy, glaucoma, addiction disorders, dependencies, alcoholism, tremors, Wilson's disease, vascular dementias, multi infarct dementia, frontotemporal dementia, pseudo-dementia, bladder cancer, ureter cancer, urethra cancer, urachus cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer, melanoma, mesothelioma, pancreatic cancer, rectal cancer, renal cancer, squamous cell carcinoma, t cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, angiosarcomas, liposarcomas, ascites, malignant ascites, mesothelioma, salivary gland tumors, mucoepidermoid carcinoma of the salivary gland, acinic cell carcinoma of the salivary gland, gastrointestinal stromal tumors (GIST—which includes, without limitation, $1^{st}$ line, $2^{nd}$ line and neoadjuvant GIST), tumors that cause effusions in potential spaces of the body, pleural effusions, pericardial effusions, peritoneal effusions aka ascites, giant cell tumors (GCT), GCT of bone, pigmented villonodular synovitis (PVNS), tenosynovial giant cell tumor (TGCT), TCGT of tendon sheath (TGCT-TS), other sarcomas; tumor angiogenesis and paracrine tumor growth; and tumors that express aberrantly or otherwise Fms, CSF1R, CSF1 or IL-34, or activating mutations or translocations of any of the foregoing.

In the embodiments and aspects described in this disclosure, crystalline or polymorphs of Compound I are intended to include, without limitation, Compound I Form A, Compound I Form B, Compound I Form C according, and Compound I Form D.

In some embodiments, the disease or condition treatable with one or more solid, crystalline or polymorphs of Compound I or solid or crystalline Compound II or compositions as described herein is selected from primary progressive multiple sclerosis, malignant peripheral nerve sheath tumors (MPNST), plexiform neurofibromas, mesothelioma, multi infarct dementia, fronto temporal dementia, mucoepidermoid carcinoma of the salivary gland, gastrointestinal stromal tumors (GIST—which includes, without limitation, $1^{st}$ line, $2^{nd}$ line and neoadjuvant GIST), pigmented villonodular synovitis (PVNS) or tenosynovial giant cell tumor (TGCT).

In some embodiments, the disclosure provides a method for treating a subject suffering from or at risk of tenosynovial giant cell tumor (TGCT) comprising administering to the subject a therapeutically effective amount of Compound I Form A, Compound I Form B, Compound I Form C, Compound I Form D or crystalline Compound II or a composition comprising Compound I Form A, Compound I Form B, Compound I Form C, Compound I Form D, or crystalline Compound II and a pharmaceutically acceptable carrier. In some embodiments, the disclosure provides a method for treating a subject suffering from or at risk of pigmented villonodular synovitis (PVNS) comprising administering to the subject a therapeutically effective amount of Compound I Form A, Compound I Form B, Compound I Form C, Compound I Form D or crystalline Compound II or a composition comprising Compound I Form A, Compound I Form B, Compound I Form C, Compound I Form D or crystalline Compound II and a pharmaceutically acceptable carrier. In some embodiments, the disclosure provides a method for treating a subject suffering from or at risk of malignant peripheral nerve sheath tumors (MPNST) comprising administering to the subject a therapeutically effective amount of Compound I Form A, Compound I Form B, Compound I Form C, Compound I Form D or crystalline Compound II or a composition comprising Compound I Form A, Compound I Form B, Compound I Form C, Compound I Form D or crystalline Compound II and a pharmaceutically acceptable carrier. In some embodiments, the disclosure provides a method for treating a subject suffering from or at risk of plexiform neurofibromas comprising administering to the subject a therapeutically effective amount of Compound I Form A, Compound I Form B, Compound I Form C, Compound I Form D or crystalline Compound II or a composition comprising Compound I Form A, Compound I Form B, Compound I Form C, Compound I Form D or crystalline Compound II and a pharmaceutically acceptable carrier. In some embodiments, the disclosure provides a method for treating a subject suffering from or at risk of malignant peripheral nerve sheath tumors (MPNST) comprising administering to the subject a therapeutically effective amount of Compound I Form C, or a composition comprising Compound I Form C, and a pharmaceutically acceptable carrier. In some embodiments, the disclosure provides a method for treating a subject suffering from or at risk of plexiform neurofibromas comprising administering to the subject a therapeutically effective amount of Compound I Form C, or a composition comprising Compound I Form C, and a pharmaceutically acceptable carrier.

In some embodiments, the disclosure provides a method for treating a subject suffering from or at risk of solid tumors comprising administering to the subject a therapeutically effective amount of Compound I Form A, Compound I Form B, Compound I Form C, Compound I Form D or crystalline Compound II or a composition comprising Compound I Form A, Compound I Form B, Compound I Form C, Compound I Form D, or crystalline Compound II and a pharmaceutically acceptable carrier, and optionally further administering a therapeutically effective amount of paclitaxel. In some embodiments, the solid tumor is advanced, metastatic or non-resectable epithelial ovarian cancer, primary peritoneal cancer, or fallopian tube cancer. In some embodiments, the disclosure provides a method for treating a subject suffering from or at risk of advanced, metastatic or non-resectable epithelial ovarian cancer, primary peritoneal cancer, or fallopian tube cancer, comprising administering to the subject a therapeutically effective amount of Compound I Form C, or a composition comprising Compound I Form C, and a pharmaceutically acceptable carrier.

In aspects and embodiments involving treatment of a disease or condition with one or more solid, crystalline or polymorphs of Compound I or solid or crystalline Compound II described herein, the disclosure provides methods for treating a Kit-mediated disease or condition in a subject in need thereof (e.g. a mammal such as a human, other primates, sports animals, animals of commercial interest such as cattle, farm animals such as horses, or pets such as dogs and cats), e.g., a disease or condition characterized by abnormal Kit activity (e.g. kinase activity). In some embodiments, the methods may involve administering to the subject suffering from or at risk of a c-Kit-mediated disease or condition an effective amount of one or more compound(s) as described herein. In one embodiment, the Kit mediated disease is selected from the group consisting of malignancies, including, but not limited to, mast cell tumors, small cell lung cancer, non-small cell lung cancer (NSCLC), testicular cancer, pancreatic cancer, breast cancer, merkel cell carcinoma, carcinomas of the female genital tract, sarcomas of neuroectodermal origin, colorectal carcinoma, carcinoma in situ, gastrointestinal stromal tumors (GISTs—which includes, without limitation, $1^{st}$ line, $2^{nd}$ line and neoadjuvant GIST), tumor angiogenesis, glioblastoma, astrocytoma, neuroblastoma, neurofibromatosis (including Schwann cell neoplasia associated with neurofibromatosis), acute myeloid leukemia, acute lymphocytic leukemia, chronic myeloid leukemia, mastocytosis, melanoma, and canine mast cell tumors; cardiovascular disease, including but not limited to atherosclerosis, cardiomyopathy, heart failure, pulmonary arterial hypertension and pulmonary fibrosis; inflammatory and autoimmune indications, including, but not limited to, allergy, anaphylaxis, asthma, rheumatoid arthritis, allergic rhinitis, multiple sclerosis, inflammatory bowel disease, transplant rejection, hypereosinophilia, urticaria and dermatitis; gastrointestinal indications, including but not limited to gastroesophageal reflux disease (GERD), esophagitis, and gastrointestinal tract ulcers; ophthalmic indications, including but not limited to uveitis and retinitis; and neurologic indications, including, but not limiting to migraine and tumors that express aberrantly or otherwise Kit, SCFR, SCF, or activating mutations or translocations of any of the foregoing.

In aspects and embodiments involving treatment of a disease or condition with one or more solid, crystalline or polymorphs of Compound I or solid or crystalline Compound II as described herein, the disclosure provides methods for treating a Fms-mediated disease or condition in a subject in need thereof (e.g. a mammal such as a human, other primates, sports animals, animals of commercial interest such as cattle, farm animals such as horses, or pets such as dogs and cats), e.g., a disease or condition characterized by abnormal Fms activity (e.g. kinase activity). In some embodiments, the methods may involve administering to the subject suffering from or at risk of a Fms-mediated disease or condition an effective amount of one or more compound(s) as described herein. In one embodiment, the Fms mediated disease is selected from the group consisting of inflammatory and autoimmune indications, including, but not limited to, rheumatoid arthritis, osteoarthritis, psoriatic arthritis, psoriasis, dermatitis, ankylosing spondylitis, polymyositis, dermatomyositis, systemic sclerosis, juvenile idiopathic arthritis, polymyalgia rheumatica, Sjogren's disease, Langerhan's cell histiocytosis (LCH), Still's disease, inflammatory bowel disease, ulcerative colitis, Crohn's disease, systemic lupus erythematosis (SLE), immune thrombocytopenic purpura (ITP), myelopreparation for autologous transplantation, transplant rejection, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, osteodystrophy, increased risk of fracture, Paget's disease, hypercalcemia, infection-mediated osteolysis (e.g. osteomyelitis), and peri-prosthetic or wear-debris-mediated osteolysis; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the nervous system, including, but not limited to, demyelinating disorders (e.g. multiple sclerosis, Charcot Marie Tooth syndrome), amyotrophic lateral sclerosis (ALS), myasthenia gravis, chronic demyelinating polyneuropathy, other demyelinating disorders, stroke, Alzheimer's disease and Parkinson's disease; pain, including, but not limited to, chronic pain, acute pain, inflammatory pain, neuropathic pain, bone pain; malignancies, including, but not limited to, multiple myeloma, acute myeloid leukemia (AML), chronic myeloid leukemia (CIVIL), lung cancer, pancreatic cancer, prostate cancer, breast cancer, ovarian cancer, neuroblastoma, sarcoma, osteosarcoma, giant cell tumors, (e.g. giant cell tumor of bone, giant cell tumor of tendon sheath (TGCT)), pigmented villonodular synovitis (PVNS), tumor angiogenesis, melanoma, glioblastoma multiforme, a subset of glioblastoma, proneural subset of glioblastoma, glioma, other tumors of the central nervous system, metastasis of tumors to other tissues, osteolytic bone metastases, and other chronic myeloproliferative diseases such as myelofibrosis; vasculitis, including but not limited to collagen vascular disease, polyarteritis nodosa, Behcet's disease, sarcoidosis, familiar Mediterranean fever, Churg-Strauss vasculitis, temporal arteritis, giant cell arteritis, Takayasu's arteritis; ophthalmic indications, including but not limited to uveitis, scleritis, retinitis, age related macular degeneration, choroidal neovascularization, diabetic retinopathy; inherited disorders, including but not limited to cherubism, neurofibromatosis; infectious disease indications, including but not limited to infections associated with human immunodeficiency virus, hepatitis B virus, hepatitis C virus, human granulocytic anaplasmosis; lysosomal storage disorders, including but not limited to Gaucher's disease, Fabry's disease, Niemann-Pick disease; gastrointestinal indications, including but not limited to liver cirrhosis; pulmonary indications, including but not limited to pulmonary fibrosis, acute lung injury (e.g. ventilator-induced, smoke- or toxin-induced); surgical indications, including but not limited to (cardiopulmonary) bypass surgery, vascular surgery, and vascular grafts; and tumors that express aberrantly or otherwise Fms, CSF1R, CSF1 or IL-34, or activating mutations or translocations of any of the foregoing.

In another embodiment of this disclosure, the CSF1R (Fms) mediated disease that can be treated by any of compounds in this disclosure is epilepsy.

In another embodiment of this disclosure, the CSF1R (Fms) mediated disease that can be treated by any of compounds in this disclosure is traumatic brain injury.

In another embodiment of this disclosure, the CSF1R (Fms) mediated disease that can be treated by any of compounds in this disclosure, in combination with dovitinib or vatalanib, is glioblastoma (GBM).

In another embodiment of this disclosure, the CSF1R (Fms) mediated disease that can be treated by any of compounds in this disclosure include tauopathies.

In another embodiment of this disclosure, the CSF1R (Fms) mediated disease that can be treated by any of compounds in this disclosure include reducing viral reservoirs in patients.

In another embodiment of this disclosure, the CSF1R (Fms) mediated disease that can be treated by any of compounds in this disclosure include Erdheim Chester Disease/Langerhans cell histocytosis, hairy cell leukemia, and non-small cell lung cancer (NSCLC).

In another embodiment of this disclosure, disease that can be treated by any of compounds in this disclosure is scleroderma. In this embodiment, the compound of this disclosure is administered topically, and can be administered in a topical formulation such as a gel, cream or spray as non-limiting examples.

In another embodiment of this disclosure, the CSF1R (Fms) mediated disease that can be treated by any of compounds in this disclosure is anterior eye disease or posterior eye disease. Examples of these eye diseases include diseases of the cornea, conjunctiva, sclera, and lacrimal glands.

In aspects and embodiments involving treatment of a disease or condition with one or more solid, crystalline or polymorphs of Compound I or solid or crystalline Compound II as described herein, the disclosure provides methods for treating a disease or condition mediated by Fms and Kit in a subject in need thereof (e.g. a mammal such as a human, other primates, sports animals, animals of commercial interest such as cattle, farm animals such as horses, or pets such as dogs and cats), e.g., a disease or condition characterized by abnormal Fms activity and Kit activity (e.g. kinase activity). In some embodiments, the methods may involve administering to the subject suffering from or at risk of a disease or condition mediated by Fms and Kit an effective amount of one or more compound(s) as described herein. In one embodiment, the condition mediated by Fms and Kit is selected from the group consisting of rheumatoid arthritis, osteoarthritis, psoriatic arthritis, psoriasis, dermatitis, allergy, anaphylaxis, asthma, allergic rhinitis, ankylosing spondylitis, polymyositis, dermatomyositis, systemic sclerosis, juvenile idiopathic arthritis, polymyalgia rheumatica, Sjogren's disease, Langerhan's cell histiocytosis, Still's disease, inflammatory bowel disease, ulcerative colitis, Crohn's disease, systemic lupus erythematosis, immune thrombocytopenic purpura, myelopreparation for autologous transplantation, transplant rejection, chronic obstructive pulmonary disease, emphysema, Kawasaki's Disease, hemophagocytic syndrome, multicentric reticulohistiocytosis, hypereosinophilia, and urticaria type I diabetes, type II diabetes, insulin resistance, hyperglycemia, obesity, and lipolysis, osteoporosis, osteodystrophy, increased risk of fracture, Paget's disease, hypercalcemia, infection-mediated osteolysis, and peri-prosthetic or wear-debris-mediated osteolysis, endometriosis, nephritis, tubular necrosis, diabetes-associated renal complications, and renal hypertrophy, multiple sclerosis, Charcot Marie Tooth syndrome, amyotrophic lateral sclerosis, myasthenia gravis, chronic demyelinating polyneuropathy, other demyelinating disorders, stroke, Alzheimer's disease and Parkinson's disease, acute pain, neuropathic pain, inflammatory pain, chronic pain, migraine, multiple myeloma, acute lymphocytic leukemia, acute myeloid leukemia, chronic myeloid leukemia, mast cell tumors, canine mast cell tumors, lung cancer, testicular cancer, pancreatic cancer, prostate cancer, breast cancer, ovarian cancer, merkel cell carcinoma, carcinomas of the female genital tract, colorectal carcinoma, carcinoma in situ, gastrointestinal stromal tumors, tumor angiogenesis, astrocytoma, neuroblastoma, sarcoma, osteosarcoma, sarcomas of neuroectodermal origin, giant cell tumor of bone, giant cell tumor of tendon sheath, pigmented villonodular synovitis, melanoma, glioblastoma, glioblastoma multiforme, glioma, other tumors of the central nervous system, neurofibromatosis (including Schwann cell neoplasia associated with neurofibromatosis), mastocytosis, metastasis of tumors to other tissues, osteolytic bone metastases, and other chronic myeloproliferative diseases such as myelofibrosis, collagen vascular disease, polyarteritis nodosa, Behcet's disease, sarcoidosis, familiar Mediterranean fever, Churg-Strauss vasculitis, temporal arteritis, giant cell arteritis, Takayasu's arteritis, uveitis, scleritis, retinitis, age related macular degeneration, choroidal neovascularization, diabetic retinopathy, cherubism, neurofibromatosis, infections associated with human immunodeficiency virus, hepatitis B virus, hepatitis C virus, human granulocytic anaplasmosis, Gaucher's disease, Fabry's disease, Niemann-Pick disease, liver cirrhosis, gastroesophageal reflux disease, esophagitis, and gastrointestinal tract ulcers, pulmonary fibrosis, acute lung injury, bypass surgery, vascular surgery, and vascular grafts, atherosclerosis, cardiomyopathy, heart failure, and pulmonary arterial hypertension.

In aspects and embodiments involving treatment of a disease or condition with one or more solid, crystalline or polymorphs of Compound I or solid or crystalline Compound II as described herein, the disclosure provides methods for treating a disease or condition mediated by Fms and Flt-3 in a subject in need thereof (e.g. a mammal such as a human, other primates, sports animals, animals of commercial interest such as cattle, farm animals such as horses, or pets such as dogs and cats), e.g., a disease or condition characterized by abnormal Fms activity and Flt-3 activity (e.g. kinase activity). In some embodiments, the methods may involve administering to the subject suffering from or at risk of a disease or condition mediated by Fms and Flt-3 an effective amount of one or more compound(s) as described herein. In one embodiment, the condition mediated by Fms and Flt-3 is acute myeloid leukemia.

In aspects and embodiments involving treatment of a disease or condition with one or more solid, crystalline or polymorphs of Compound I or solid or crystalline forms of Compound II as described herein, the methods may involve administering an effective amount of one or more compound(s) or one or more composition(s) as described herein, and optionally in combination with another therapeutic agent or therapy as described herein, to a subject in need thereof suffering from or at risk of a disease or condition selected from the group consisting of rheumatoid arthritis, osteoarthritis, osteoporosis, peri-prosthetic osteolysis, systemic sclerosis, demyelinating disorders, multiple sclerosis, Charcot Marie Tooth syndrome, amyotrophic lateral sclerosis, Alzheimer's disease, Parkinson's disease, ulcerative colitis, Crohn's disease, immune thrombocytopenic purpura, atherosclerosis, systemic lupus erythematosis, myelopreparation for autologous transplantation, transplant rejection, glomerulonephritis, interstitial nephritis, Lupus nephritis, tubular necrosis, diabetic nephropathy, renal hypertrophy, type I diabetes, acute pain, inflammatory pain, neuropathic pain, acute myeloid leukemia, melanoma, multiple myeloma, metastatic breast cancer, prostate cancer, pancreatic cancer, lung cancer, ovarian cancer, gliomas, glioblastomas, neurofibromatosis, osteolytic bone metastases, brain metastases, gastrointestinal stromal tumors, and giant cell tumors.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of lysosomal storage disorders. Non-limiting examples of lysosomal storage disorders include mucolipodosis, alpha-mannosidosis, aspartylglucosaminuria, Batten disease, beta-mannosidosis, cystinosis, Danon disease, Fabry disease, Farber disease, fucosidosis, galactosialidosis, Gaucher disease, gangliosidosis (e.g., GM1 gangliosidosis and GM2-gangliosidosis AB variant), Krabbe disease, metachromatic leukodystrophy, mucopolysaccharidoses disorders (e.g., MPS 1—Hurler syndrome, MPS II—Hunter syndrome, MPS III—Sanfilippo (A,B,C, D), MPS IVA—Morquio, MPS IX—hyaluronidase, deficiency, MPS VI—Maroteaux-Lamy, or MPS VII—Sly syndrome), mucolipidosis type I (Sialidosis), mucolipidosis type II (I-Cell disease); mucolipidosis type III (Pseudo-Hurler polydystrophy), mucolipidosis type IV, multiple sulfatase deficiency, Niemann-Pick types A, B, C, Pompe disease (glycogen storage disease), pycnodysostosis, Sandhoff disease, Schindler disease, Salla disease/sialic acid storage disease, Tay-Sachs, and Wolman disease.

Further to any of the aspects and embodiments referred to herein, a compound as described herein also inhibits the effects of a mutation of the kinase (e.g. Fms mutant, Kit mutant, Flt-3 mutant, e.g., internal tandem duplications (ITD)), including, but not limiting to, a mutation that is related to a disease state, such as a cancer.

In aspects and embodiments involving treatment of a disease or condition with one or more solid, crystalline or polymorphs of Compound I or solid or crystalline forms of Compound II as described herein, the methods involve administering an effective amount of one or more compound(s) as described herein or a composition thereof as described herein, and optionally in combination with another therapeutic agent or therapy as described herein, to a subject in need thereof suffering from or at risk of a disease or condition selected from the group consisting of from stem cell ablation and myelopreparation for stem cell transplant, monocytic leukemia, primary progressive multiple sclerosis, complex regional pain syndrome, reflex sympathetic dystrophy, muscular dystrophy, duchenne muscular dystrophy, causalgia, malignant peripheral nerve cell tumors, malignant peripheral nerve sheath tumors, pheochromocytomas cutaneous and plexiform neurofibromas, neuro-inflammations, benign forgetfulness, HIV, binswager type dementia, dementia with lewy bodie, prosencephaly, microencephy, cerebral palsy, congenital hydrocephalus, tremors, Wilson's disease, vascular dementias/multi infarct dementia, fronto temporal type, pseudo-dementia, papillary thyroid cancer, anaplastic thyroid cancer, medullary thyroid cancer, follicular thyroid cancer, hurthle cell carcinoma, thyroid cancer, ascites, malignant ascites, abdominal dropsy, progressive supranuclear palsy, glaucoma, mesothelioma, salivary gland tumors, mucoepidermoid carcinoma of the salivary gland, acinic cell carcinoma of the salivary gland, and others), gastrointestinal stromal tumors (GIST—which includes, without limitation, $1^{st}$ line, $2^{nd}$ line and neoadjuvant GIST), tumors that cause effusions in potential spaces of the body, pleural effusions, pericardial effusions, peritoneal effusions aka ascites, giant cell tumors (GCT), GCT of bone, pigmented villonodular synovitis (PVNS), tenosynovial giant cell tumor (TGCT), TCGT of tendon sheath (TGCT-TS), other sarcomas, tumor angiogenesis and paracrine tumor growth; and tumors that express aberrantly or otherwise Fms, CSF1R, CSF1 or IL-34, or activating mutations or translocations of any of the foregoing, wherein the compound is an inhibitor of Kit.

In aspects and embodiments involving treatment of a disease or condition with one or more solid, crystalline or polymorphs of Compound I or solid or crystalline forms of Compound II as described herein, the methods may involve administering an effective amount of one or more solid, crystalline or polymorphs of Compound I or solid or crystalline forms of Compound II as described herein or a composition thereof as described herein, and optionally in combination with another therapeutic agent or therapy as described herein, to a subject in need thereof suffering from or at risk of a disease or condition selected from the group consisting of from alopecia, baldness, wound healing, androgenetic alopecia (AGA), epilepsy, traumatic brain injury, tauopathies, Erdheim Chester Disease, Langerhans cell histocytosis, hairy cell leukemia, non-small cell lung cancer, cleroderma, anterior eye disease, posterior eye disease, lysosomal storage disease, stem cell ablation and myelopreparation for stem cell transplant, primary progressive multiple sclerosis, complex regional pain syndrome, reflex sympathetic dystrophy, muscular dystrophy, duchenne muscular dystrophy, causalgia, neuro-inflammation, neuroinflammatory disorders, benign forgetfulness, HIV, binswager type dementia, dementia with lewy bodie, prosencephaly, microencephy, cerebral palsy, congenital hydrocephalus, abdominal dropsy, progressive supranuclear palsy, glaucoma, addiction disorders, dependencies, alcoholism, tremors, Wilson's disease, vascular dementias, multi infarct dementia, fronto temporal dementia, pseudo-dementia, bladder cancer, ureter cancer, urethra cancer, urachus cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer, melanoma, mesothelioma, pancreatic cancer, rectal cancer, renal cancer, squamous cell carcinoma, t cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, angiosarcomas, liposarcomas, ascites, malignant ascites, mesothelioma, salivary gland tumors, mucoepidermoid carcinoma of the salivary gland, acinic cell carcinoma of the salivary gland, gastrointestinal stromal tumors (GIST—which includes, without limitation, $1^{st}$ line, $2^{nd}$ line and neoadjuvant GIST), tumors that cause effusions in potential spaces of the body, pleural effusions, pericardial effusions, peritoneal effusions aka ascites, giant cell tumors (GCT), GCT of bone, pigmented villonodular synovitis (PVNS), tenosynovial giant cell tumor (TGCT), TCGT of tendon sheath (TGCT-TS), and other sarcomas; tumor angiogenesis and paracrine tumor growth and tumors that express aberrantly or otherwise Fms, CSF1R, CSF1 or IL-34, or activating mutations or translocations of any of the foregoing.

In aspects and embodiments involving treatment of a disease or condition with one or more solid, crystalline or polymorphs of Compound I or solid or crystalline forms of Compound II as described herein, the methods may involve administering an effective amount of one or more solid, crystalline or polymorphs of Compound I or solid or crystalline forms of Compound II as described herein, or a composition thereof as described herein, and optionally in combination with another therapeutic agent or therapy as described herein, to a subject in need thereof suffering from or at risk of a disease or condition selected from the group consisting of alopecia, baldness, wound healing, androgenetic alopecia (AGA), epilepsy, traumatic brain injury, tauopathies, Erdheim Chester Disease, Langerhans cell histocytosis, hairy cell leukemia, non-small cell lung cancer, cleroderma, anterior eye disease, posterior eye disease, lysosomal storage disease, stem cell ablation and myelopreparation for stem cell transplant, primary progressive multiple sclerosis, complex regional pain syndrome, reflex sympathetic dystrophy, muscular dystrophy, duchenne muscular dystrophy, causalgia, neuro-inflammation, neuroinflammatory disorders, benign forgetfulness, HIV, binswager type dementia, dementia with lewy bodie, prosencephaly, microencepahy, cerebral palsy, congenital hydrocephalus, abdominal dropsy, progressive supranuclear palsy, glaucoma, addiction disorders, dependencies, alcoholism, tremors, Wilson's disease, vascular dementias, multi infarct dementia, fronto temporal dementia, pseudo-dementia, bladder cancer, ureter cancer, urethra cancer, urachus cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer, melanoma, mesothelioma, pancreatic cancer, rectal cancer, renal cancer, squamous cell carcinoma, t cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, angiosarcomas, liposarcomas, ascites, malignant ascites, mesothelioma, salivary gland tumors, mucoepidermoid carcinoma of the salivary gland, acinic cell carcinoma of the salivary gland, gastrointestinal stromal tumors (GIST—which includes, without limitation, $1^{st}$ line, $2^{nd}$ line and neoadjuvant GIST), tumors that cause effusions in potential spaces of the body, pleural effusions, pericardial effusions, peritoneal effusions aka ascites, giant cell tumors (GCT), GCT of bone, pigmented villonodular synovitis (PVNS), tenosynovial giant cell tumor (TGCT), TCGT of tendon sheath (TGCT-TS), other sarcomas; tumor angiogenesis and paracrine tumor growth and tumors that express aberrantly or otherwise Fms, CSF1R, CSF1 or IL-34, or activating mutations or translocations of any of the foregoing, wherein the compound is a dual Fms/Kit inhibitor.

In aspects and embodiments involving treatment of a disease or condition with one or more solid, crystalline or polymorphs of Compound I or solid or crystalline forms of Compound II as described herein, the methods may involve administering an effective amount one or more solid, crystalline or polymorphs of Compound I or solid or crystalline forms of Compound II as described herein, or a composition thereof as described herein, and optionally in combination with another therapeutic agent or therapy as described herein, to a subject in need thereof suffering from or at risk of acute myeloid leukemia, wherein the compound is a dual Fms/Flt-3 inhibitor.

In another aspect, the disclosure provides kits that include one or more solid, crystalline or polymorphs of Compound I or solid or crystalline Compound II or composition thereof as described herein. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a Fms and/or Kit protein kinase mediated disease or condition; the disclosure kit includes written instructions for use and/or other indication that the compound or composition is suitable or approved for administration to a mammal, e.g., a human, for a Fms and/or Kit protein kinase-mediated disease or condition; and the compound or composition is packaged in unit dose or single dose form, e.g., single dose pills, capsules, or the like.

In yet another aspect, one or more solid, crystalline or polymorphs of Compound I or solid or crystalline forms of Compound II as described herein, or a composition thereof as described herein, and optionally in combination with another therapeutic agent or therapy as described herein, can be used in the preparation of a medicament for the treatment of a Kit-mediated disease or condition as described herein, a Fms-mediated disease or condition as described herein, a Fms-mediated and Kit-mediated disease or condition as described herein, a Flt3-mediated disease or condition as described herein or a Fms-mediated and Flt3-mediated disease or condition as described herein, wherein the Kit, Fms or Flt3 kinases can include any mutations thereof. In other embodiments, the disclosure provides one or more compounds or compositions as described herein for use in treating a Fms-mediated and Kit-mediated disease or condition as described herein. In yet other embodiments, the disclosure provides one or more compounds or compositions as described herein for use in treating a Kit-mediated disease or condition as described herein. In still other embodiments, the disclosure provides one or more compounds or compositions as described herein for use in treating a Fms-mediated disease or condition as described herein.

In some embodiments, one or more solid, crystalline or polymorphs of Compound I or solid or crystalline forms of Compound II as described herein, or a composition thereof as described herein, and optionally in combination with another therapeutic agent or therapy as described herein, can be used in the preparation of a medicament for the treatment of a disease or condition selected from the group consisting of alopecia, baldness, wound healing, androgenetic alopecia (AGA), epilepsy, traumatic brain injury, tauopathies, Erdheim Chester Disease, Langerhans cell histocytosis, hairy cell leukemia, non-small cell lung cancer, cleroderma, anterior eye disease, posterior eye disease, lysosomal storage disease, stem cell ablation and myelopreparation for stem cell transplant, primary progressive multiple sclerosis, complex regional pain syndrome, reflex sympathetic dystrophy, muscular dystrophy, duchenne muscular dystrophy, causalgia, neuro-inflammation, neuroinflammatory disorders, benign forgetfulness, HIV, binswager type dementia, dementia with lewy bodie, prosencephaly, microencepahy, cerebral palsy, congenital hydrocephalus, abdominal dropsy, progressive supranuclear palsy, glaucoma, addiction disorders, dependencies, alcoholism, tremors, Wilson's disease, vascular dementias, multi infarct dementia, fronto temporal dementia, pseudo-dementia, bladder cancer, ureter cancer, urethra cancer, urachus cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer, melanoma, mesothelioma, pancreatic cancer, rectal cancer, renal cancer, squamous cell carcinoma, t cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, angiosarcomas, liposarcomas, ascites, malignant ascites, mesothelioma, salivary gland tumors, mucoepidermoid carcinoma of the salivary gland, acinic cell carcinoma of the salivary gland, gastrointestinal stromal tumors (GIST— which includes, without limitation, $1^{st}$ line, $2^{nd}$ line and neoadjuvant GIST), tumors that cause effusions in potential spaces of the body, pleural effusions, pericardial effusions, peritoneal effusions aka ascites, giant cell tumors (GCT), GCT of bone, pigmented villonodular synovitis (PVNS), tenosynovial giant cell tumor (TGCT), TCGT of tendon sheath (TGCT-TS), other sarcomas; tumor angiogenesis and paracrine tumor growth; and tumors that express aberrantly or otherwise Fms, CSF1R, CSF1 or IL-34, or activating mutations or translocations of any of the foregoing.

In some embodiments, one or more solid, crystalline or polymorphs of Compound I or solid or crystalline forms of Compound II as described herein, or a composition thereof as described herein, that are Kit inhibitors can be used, optionally in combination with another therapeutic agent or therapy as described herein, in the preparation of a medicament for the treatment of neuro-inflammations, benign forgetfulness, HIV, binswager type dementia, dementia with lewy bodie, prosencephaly, microencepahy, cerebral palsy, congenital hydrocephalus, tremors, Wilson's disease, vascular dementias/multi infarct dementia, fronto temporal type, pseudo-dementia, papillary thyroid cancer, anaplastic thyroid cancer, medullary thyroid cancer, follicular thyroid cancer, hurthle cell carcinoma, thyroid cancer, ascites and malignant ascites.

In some embodiments, one or more solid, crystalline or polymorphs of Compound I or solid or crystalline forms of Compound II as described herein, or a composition thereof as described herein, that are Fms inhibitors can be used, optionally in combination with another therapeutic agent or therapy as described herein, in the preparation of a medicament for the treatment of neuro-inflammations, benign forgetfulness, HIV, binswager type dementia, dementia with lewy bodie, prosencephaly, microencepahy, cerebral palsy, congenital hydrocephalus, tremors, Wilson's disease, vascular dementias/multi infarct dementia, fronto temporal type, pseudo-dementia, papillary thyroid cancer, anaplastic thyroid cancer, medullary thyroid cancer, follicular thyroid cancer, hurthle cell carcinoma, thyroid cancer, ascites, and malignant ascites.

In some embodiments, one or more solid, crystalline or polymorphs of Compound I or solid or crystalline forms of Compound II as described herein, or a composition thereof as described herein, that are Fms inhibitors that effectively cross the blood brain barrier can be used, optionally in combination with another therapeutic agent or therapy as described herein, in the preparation of a medicament for the treatment of multiple sclerosis, glioblastoma, Alzheimer's disease, or Parkinson's disease.

In some embodiments, one or more solid, crystalline or polymorphs of Compound I or solid or crystalline forms of Compound II as described herein, or a composition thereof as described herein, that are Fms inhibitors that do not effectively cross the blood brain barrier can be used, optionally in combination with another therapeutic agent or therapy as described herein, in the preparation of a medicament for the treatment of rheumatoid arthritis, osteoarthritis, atherosclerosis, systemic lupus erythematosus, glomerulonephritis, interstitial nephritis, Lupus nephritis, tubular necrosis, diabetic nephropathy, or renal hypertrophy.

In some embodiments, one or more solid, crystalline or polymorphs of Compound I or solid or crystalline forms of Compound II as described herein, or a composition thereof as described herein, that are dual Fms/Kit inhibitors can be used, optionally in combination with another therapeutic agent or therapy as described herein, in the preparation of a medicament for the treatment of metastatic breast cancer, prostate cancer, multiple myeloma, melanoma, acute myeloid leukemia, brain metastases, neurofibromatosis, gastrointestinal stromal tumors, rheumatoid arthritis, or multiple sclerosis.

In some embodiments, one or more solid, crystalline or polymorphs of Compound I or solid or crystalline forms of Compound II as described herein, or a composition thereof as described herein, that are dual Fms/Kit inhibitors can be used, optionally in combination with another therapeutic agent or therapy as described herein, in the preparation of a medicament for the treatment of neuro-inflammations, benign forgetfulness, HIV, binswager type dementia, dementia with lewy bodie, prosencephaly, microencepahy, cerebral palsy, congenital hydrocephalus, primary progressive multiple sclerosis, complex regional pain syndrome, reflex sympathetic dystrophy, muscular dystrophy, duchenne muscular dystrophy, causalgia, tremors, Wilson's disease, vascular dementias/multi infarct dementia, fronto temporal type, pseudo-dementia, papillary thyroid cancer, anaplastic thyroid cancer, medullary thyroid cancer, follicular thyroid cancer, hurthle cell carcinoma, thyroid cancer, ascites, and malignant ascites.

In some embodiments, one or more solid, crystalline or polymorphs of Compound I or solid or crystalline forms of Compound II as described herein, or a composition thereof as described herein, that are dual Fms/Flt-3 inhibitors can be used, optionally in combination with another therapeutic agent or therapy as described herein, in the preparation of a medicament for the treatment of acute myeloid leukemia. In some embodiments, the disclosure provides a method for treating a subject suffering from or at risk of acute myeloid leukemia comprising administering to the subject a therapeutically effective amount of Compound I Form A, Compound I Form B, Compound I Form C, Compound I Form D or crystalline Compound II or a composition comprising Compound I Form A, Compound I Form B, Compound I Form C, Compound I Form D or crystalline Compound II and a pharmaceutically acceptable carrier.

In some embodiments, one or more solid, crystalline or polymorphs of Compound I or solid or crystalline forms of Compound II, or a composition thereof as described herein, and optionally in combination with another therapeutic agent or therapy as described herein, can be used for the treatment of a Kit-mediated disease or condition as described herein, a Fms-mediated disease or condition as described herein, a Fms-mediated and Kit-mediated disease or condition as described herein, a Flt3-mediated disease or condition as described herein or a Fms-mediated and Flt3-mediated disease or condition as described herein, wherein the Kit, Fms or Flt3 kinases can include any mutations thereof. In other embodiments, the disclosure provides one or more compounds or compositions as described herein, and optionally in combination with another therapeutic agent or therapy as described herein, for use in treating a Fms-mediated and Kit-mediated disease or condition as described herein. In yet other embodiments, the disclosure provides one or more compounds or compositions as described herein, and optionally in combination with another therapeutic agent or therapy as described herein, for use in treating a Kit-mediated disease or condition as described herein. In still other embodiments, the disclosure provides one or more compounds or compositions as described herein, and optionally in combination with another therapeutic agent or therapy as described herein, for use in treating a Fms-mediated disease or condition as described herein.

In some embodiments, one or more solid, crystalline or polymorphs of Compound I or solid or crystalline forms of Compound II as described herein, or a composition thereof as described herein, and optionally in combination with another therapeutic agent or therapy as described herein can be used for the treatment of a disease or condition selected from the group consisting of alopecia, baldness, wound healing, androgenetic alopecia (AGA), epilepsy, traumatic brain injury, tauopathies, Erdheim Chester Disease, Langerhans cell histocytosis, hairy cell leukemia, non-small cell lung cancer, cleroderma, anterior eye disease, posterior eye disease, lysosomal storage disease, stem cell ablation and myelopreparation for stem cell transplant, primary progressive multiple sclerosis, complex regional pain syndrome, reflex sympathetic dystrophy, muscular dystrophy, duchenne muscular dystrophy, causalgia, neuro-inflammation, neuroinflammatory disorders, benign forgetfulness, HIV, binswager type dementia, dementia with lewy bodie, prosencephaly, microencepahy, cerebral palsy, congenital hydrocephalus, abdominal dropsy, progressive supranuclear palsy, glaucoma, addiction disorders, dependencies, alcoholism, tremors, Wilson's disease, vascular dementias, multi infarct dementia, fronto temporal dementia, pseudo-dementia, bladder cancer, ureter cancer, urethra cancer, urachus cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer, melanoma, mesothelioma, pancreatic cancer, rectal cancer, renal cancer, squamous cell carcinoma, t cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, angiosarcomas, liposarcomas, ascites, malignant ascites, mesothelioma, salivary gland tumors, mucoepidermoid carcinoma of the salivary gland, acinic cell carcinoma of the salivary gland, gastrointestinal stromal tumors (GIST—which includes, without limitation, $1^{st}$ line, $2^{nd}$ line and neoadjuvant GIST), tumors that cause effusions in potential spaces of the body, pleural effusions, pericardial effusions, peritoneal effusions aka ascites, giant cell tumors (GCT), GCT of bone, pigmented villonodular synovitis (PVNS), tenosynovial giant cell tumor (TGCT), TCGT of tendon sheath (TGCT-TS), other sarcomas, tumor angiogenesis and paracrine tumor growth. In some embodiments, one or more solid, crystalline or polymorphs of Compound I or solid or crystalline forms of Compound II as described herein, or a composition thereof as described herein, and optionally in combination with another therapeutic agent or therapy as described herein can be used for the treatment of tumors that express aberrantly or otherwise Fms, CSF1R, CSF1 or IL-34, or activating mutations or translocations of any of the foregoing. In other embodiments, one or more solid, crystalline or polymorphs of Compound I or solid or crystalline forms of Compound II as described herein, or a composition thereof as described herein, and optionally in combination with another therapeutic agent or therapy as described herein, can be used for the treatment of tumors that express aberrantly or otherwise Kit, SCFR, SCF, or activating mutations or translocations of any of the foregoing. In yet other embodiments, one or more solid, crystalline or polymorphs of Compound I or solid or crystalline forms of Compound II as described herein, or a composition thereof as described herein, and optionally in combination with another therapeutic agent or therapy as described herein can be used for the treatment of tumors that express aberrantly or otherwise Flt3, Flt3 ligand, or activating mutations or translocations of any of the foregoing.

In some embodiments, the disclosure provides a method for regulating/modulating tumor associated macrophages (TAM), for example, by depleting, inhibiting or reducing TAM or blocking proliferation, migration or activation of TAM in a subject. The method includes administering to the subject an effective amount of one or more solid, crystalline or polymorphs of Compound I or solid or crystalline forms of Compound II as described herein, or a composition thereof as described herein, and optionally in combination with another therapeutic agent or therapy as described herein. In certain embodiments, the disclosure provides a method for treating a cancer mediated or modulated by TAM. The method includes administering to the subject an effective amount one or more solid, crystalline or polymorphs of Compound I or solid or crystalline forms of Compound II as described herein, or a composition thereof as described herein, and optionally in combination with another therapeutic agent or therapy as described herein. In other embodiments, the disclosure provides a method for inhibiting infiltrating macrophages. The methods include administering to the subject an effective amount of one or more solid, crystalline or polymorphs of Compound I or solid or crystalline forms of Compound II as described herein, or a composition thereof as described herein, and optionally in combination with another therapeutic agent or therapy as described herein.

In some embodiments, the disclosure provides a method for inhibiting, reducing, or blocking proliferation, migration or activation of microglia in a subject. The method includes administering to the subject an effective amount of one or more solid, crystalline or polymorphs of Compound I or solid or crystalline forms of Compound II as described herein or a composition thereof as described herein. In one embodiment, the disclosure provides a method for depleting and/or eliminating microglia in a subject. The method includes administering to the subject an effective amount of one or more solid, crystalline or polymorphs of Compound I or solid or crystalline forms of Compound II as described herein, or a composition thereof as described herein, and optionally in combination with another therapeutic agent or therapy as described herein.

In some embodiments, the disclosure provides a method for inhibiting, reducing, or blocking proliferation, migration or activation of monocytes in a subject. In certain instances, the monocytes are CD14+CD16++ monocytes. In another instance, the monocytes are CD11b+ monocytes. The method includes administering to the subject an effective amount of one or more solid, crystalline or polymorphs of Compound I or solid or crystalline forms of Compound II as described herein, or a composition as described herein, and optionally in combination with another therapeutic agent or therapy as described herein.

In some embodiments, the disclosure provides a method for inhibiting, reducing, or blocking proliferation, migration or activation of mast cells in a subject. The method includes administering to the subject an effective amount of one or more solid, crystalline or polymorphs of Compound I or solid or crystalline forms of Compound II as described herein, or a composition thereof as described herein, and optionally in combination with another therapeutic agent or therapy as described herein.

In some embodiments, the disclosure provides a method for inhibiting, reducing, or blocking proliferation, migration or activation of osteoclasts in a subject. The method includes administering to the subject an effective amount of one or more solid, crystalline or polymorphs of Compound I or solid or crystalline forms of Compound II as described herein, or a composition thereof as described herein, and optionally in combination with another therapeutic agent or therapy as described herein.

In certain embodiments, the disclosure provides a method for treating bone osteolysis and/or bone pain. The method includes administering to the subject in need thereof an effective amount of a compound, or a composition as described herein, and optionally in combination with another therapeutic agent or therapy as described herein.

In certain embodiments, the disclosure provides a method for preventing bone and joint destruction and/or protecting bone damages from tumor cells. The method includes administering to the subject in need thereof an effective amount of one or more solid, crystalline or polymorphs of Compound I or solid or crystalline forms of Compound II as described herein, or a composition thereof as described herein, and optionally in combination with another therapeutic agent or therapy as described herein.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of stem cell ablation and myelo-preparation for stem cell transplant.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of monocytic leukemia.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of acute myeloid leukemia.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of melanoma.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of malignant peripheral nerve cell tumors.

In another aspect, one or more solid, crystalline or polymorphs of Compound I or solid or crystalline forms of Compound II as described herein, or a composition thereof as described herein, and optionally in combination with another therapeutic agent or therapy as described herein, can be used for the treatment of malignant peripheral nerve sheath tumors (MPNST).

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of pheochromocytomas cutaneous and plexiform neurofibromas. In certain aspects, one or more solid, crystalline or polymorphs of Compound I or solid or crystalline forms of Compound II as described herein can be used for the treatment of plexiform neurofibromas.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of neuro-inflammation.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of benign forgetfulness.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of binswager type dementia.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of dementia with lewy bodie.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of prosencephaly.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of microencepahy.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of cerebral palsy.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of congenital hydrocephalus.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of tremors.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of Wilson's disease.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of vascular dementias/multi infarct dementia.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of fronto temporal type, pseudo-dementia.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of thyroid cancer.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of papillary thyroid cancer.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of anaplastic thyroid cancer.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of medullary thyroid cancer.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of follicular thyroid cancer.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of hurthle cell carcinoma.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of ascites.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of malignant ascites.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of abdominal dropsy.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of progressive supranuclear palsy.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of glaucoma.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of mesothelioma.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of salivary gland tumors.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of mucoepidermoid carcinoma of the salivary gland.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of acinic cell carcinoma of the salivary gland, and others.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of gastrointestinal stromal tumors (GIST—which includes, without limitation, 1$^{st}$ line, 2$^{nd}$ line and neoadjuvant GIST).

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of tumors that cause effusions in potential spaces of the body.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of pleural effusions.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of pericardial effusions.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of peritoneal effusions aka ascites.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of giant cell tumors (GCT).

In certain aspects, one or more solid, crystalline or polymorphs of Compound I or solid or crystalline forms of Compound II as described herein, optionally in combination with another therapeutic agent or therapy as described herein, can be used for the treatment of GCT of bone.

In certain aspects, one or more compounds or a composition as described herein, optionally in combination with another therapeutic agent or therapy as described herein, can be used for the treatment of pigmented villonodular synovitis (PVNS).

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of tenosynovial giant cell tumor (TGCT).

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of TCGT of tendon sheath (TGCT-TS).

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of sarcomas.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of glioblastoma.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of breast cancer. In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of metastatic breast cancer.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of ovarian cancer. In a certain embodiment, Compound I Form C can be used for the treatment of ovarian cancer.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of prion diseases. Non-limiting examples of prion diseases include protein folding and aggregation disorders, and protein accumulation/metabolism disorders Protein folding disorders are classified as amyloidoses as well as other disorders associated with abnormal protein folding. accumulation/metabolism disorders include Gacuher, Niemann-Pick and lysosomal storage disorders. In a certain embodiment, one or more solid, crystalline or polymorphs of Compound I or solid or crystalline forms of Compound II as described herein, or a composition thereof as described herein, and optionally in combination with another therapeutic agent or therapy as described herein, can be used for the treatment of prion diseases. In a certain embodiment Compound I Form C, or a composition thereof as described herein, and optionally in combination with another therapeutic agent or therapy as described herein, can be used for the treatment of prion diseases.

In certain aspects, one or more solid, crystalline or polymorphs of Compound I or solid or crystalline forms of Compound II as described herein, or a composition thereof as described herein, and optionally in combination with another therapeutic agent or therapy as described herein, can be used for the treatment of Lysosomal Storage disorders. Non-limiting examples of lysosomal storage disorders include mucolipodosis, alpha-mannosidosis, aspartylglucosaminuria, Batten disease, beta-mannosidosis, cystinosis, Danon disease, Fabry disease, Farber disease, fucosidosis, galactosialidosis, Gaucher disease, gangliosidosis (e.g., GM1 gangliosidosis and GM2-gangliosidosis AB variant), Krabbe disease, metachromatic leukodystrophy, mucopolysaccharidoses disorders (e.g., MPS 1—Hurler syndrome, MPS II—Hunter syndrome, MPS III—Sanfilippo (A,B,C, D), MPS IVA—Morquio, MPS IX—hyaluronidase, deficiency, MPS VI—Maroteaux-Lamy, or MPS VII—Sly syndrome), mucolipidosis type I (Sialidosis), Mucolipidosis type II (I-Cell disease); Mucolipidosis type III (Pseudo-Hurler polydystrophy), Mucolipidosis type IV, multiple sulfatase deficiency, Niemann-Pick types A, B, C, Pompe disease (glycogen storage disease), pycnodysostosis, Sandhoff disease, Schindler disease, Salla disease/sialic acid storage disease, Tay-Sachs, and Wolman disease. In a certain embodiment, Compound I Form C, or a composition thereof as described herein, and optionally in combination with another therapeutic agent or therapy as described herein, can be used for the treatment of Lysosomal Storage disorders.

Combinations

In one aspect, the disclosure provides methods for treating a Fms protein kinase mediated disease or condition in an animal subject in need thereof, wherein the method involves administering to the subject an effective amount of any one or more compound(s) as described herein. In some embodiments, the method involves administering to the subject a therapeutically effective amount of Compound I Form A, Compound I Form B, Compound I Form C, Compound I Form D or crystalline Compound II. In one embodiment, the method involves administering to the subject an effective amount of subject a therapeutically effective amount of Compound I Form A, Compound I Form B, Compound I Form C, Compound I Form D or crystalline Compound II as described herein in combination with one or more other therapies for the disease or condition.

In another aspect, the disclosure provides methods for treating a Kit protein kinase mediated disease or condition in an animal subject in need thereof, wherein the method involves administering to the subject an effective amount of any one or more compound(s) as described herein. In some embodiments, the method involves administering to the subject a therapeutically effective amount of Compound I Form A, Compound I Form B, Compound I Form C, Compound I Form D or crystalline Compound II. In one embodiment, the method involves administering to the subject a therapeutically effective amount of Compound I Form A, Compound I Form B, Compound I Form C, Compound I Form D or crystalline Compound II as described herein in combination with one or more other therapies for the disease or condition.

In another aspect, compositions are provided that include a therapeutically effective amount of any one or more compound(s) as described herein and at least one pharmaceutically acceptable carrier, excipient, and/or diluent, including combinations of any two or more compounds as described herein. The composition can further include a plurality of different pharmacologically active compounds, which can include a plurality of compounds as described herein. In certain embodiments, the composition can include any one or more compound(s) as described herein along with one or more compounds that are therapeutically effective for the same disease indication. In one aspect, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer. The compounds can be administered simultaneously or sequentially.

In another aspect, methods are provided for modulating the activity of a Fms and/or Kit and/or Flt-3 protein kinase, including any mutations thereof, by contacting the protein kinase with an effective amount of any one or more compound(s) as described herein.

In another aspect, the disclosure provides methods for treating a disease or condition mediated by Fms and/or Kit and/or Flt-3, including any mutations thereof, in a subject in need thereof by administering to the subject an effective amount of a compound as described herein or a composition including any one or more compound(s) as described herein. In one embodiment, the disclosure provides methods for treating a disease or condition mediated by Fms and/or Kit, including any mutations thereof, in a subject in need thereof by administering to the subject an effective amount of a compound as described herein or a composition including any one or more compound(s) as described herein in combination with one or more other suitable therapies for treating the disease.

In another aspect, the disclosure provides methods for treating a disease or condition mediated by Fms, including any mutations thereof, in a subject in need thereof by administering to the subject an effective amount of a compound as described herein or a composition including any one or more compound(s) as described herein. In one embodiment, the disclosure provides methods for treating a disease or condition mediated by Fms, including any mutations thereof, in a subject in need thereof by administering to the subject an effective amount of a compound as described herein or a composition including any one or more compound(s) as described herein in combination with one or more other suitable therapies for treating the disease.

In another aspect, the disclosure provides methods for treating a disease or condition mediated by Kit, including any mutations thereof, in a subject in need thereof by administering to the subject an effective amount of a compound as described herein or a composition including any one or more compound(s) as described herein. In one embodiment, the disclosure provides methods for treating a disease or condition mediated by Kit, including any mutations thereof, in a subject in need thereof by administering to the subject an effective amount of a compound as described herein or a composition including any one or more compound(s) as described herein in combination with one or more other suitable therapies for treating the disease.

In another aspect, the disclosure provides methods for treating a disease or condition mediated by Flt-3, including any mutations thereof, in a subject in need thereof by administering to the subject an effective amount of a compound as described herein or a composition including any one or more compound(s) as described herein. In one embodiment, the disclosure provides methods for treating a disease or condition mediated by Flt-3, including any mutations, such as an internal tandem duplication (ITD) mutation thereof, in a subject in need thereof by administering to the subject an effective amount of a composition including any one or more compound(s) as described herein in combination with one or more other suitable therapies for treating the disease. In some embodiments, the Flt3 mutant encoded by Flt3 gene with ITD mutations has one or more mutations at residues F691, D835, Y842 or combinations thereof. In some embodiments, the Flt3 mutant has one or more mutations selected from F691L, D835V/Y, Y842C/H or combinations thereof.

In another aspect, the disclosure provides methods for treating a disease or condition mediated by Fms and Flt-3, including any mutations thereof, in a subject in need thereof by administering to the subject an effective amount of a compound as described herein or a composition including any one or more compound(s) as described herein. In one embodiment, the disclosure provides methods for treating a disease or condition mediated by Fms and Flt-3, including any mutations thereof, in a subject in need thereof by administering to the subject an effective amount of a composition including any one or more compound(s) as described herein in combination with one or more other suitable therapies for treating the disease.

In another aspect, the disclosure provides methods for treating a disease or condition mediated by Fms and Kit, including any mutations thereof, in a subject in need thereof by administering to the subject an effective amount of a compound as described herein or a composition including any one or more compound(s) as described herein. In one embodiment, the disclosure provides methods for treating a disease or condition mediated by Fms and Kit, including any mutations thereof, in a subject in need thereof by administering to the subject an effective amount of a composition including any one or more compound(s) as described herein in combination with one or more other suitable therapies for treating the disease.

In some embodiments, the disclosure provides a method of treating a subject suffering from a disease or condition described in this disclosure, said method comprising administering to the subject an effective amount of Compound I Form A, Compound I Form B, Compound I Form C, Compound I Form D or crystalline Compound II or a composition including any one or more compound(s) as described herein, in combination with immunotherapy such as i) a PD-L1 inhibitor (such as durvalumab, nivolumab, panitumumab, pertuzumab, rituximab, tositumomab, trastuzumab, and 90 Y ibritumomab tiuxetan, ii) a PD-1 inhibitor or iii) an IDO inhibitor (such as indoximod). In some embodiments, the method of treating a subject suffering from a disease or condition described in this disclosure comprises administering to the subject an effective amount of Compound I Form C, or a composition thereof, in combination a therapeutically effective amount of an IDO inhibitor (such as indoximod) for treating an infectious disease. Non-limiting examples of infectious diseases include a viral infections such as influenza, hepatitis C virus (HCV), human papilloma virus (HPV), cytomegalovirus (CMV), Epstein-Barr virus (EBV), poliovirus, varicella zoster virus, coxsackie virus, and human immunodeficiency virus (HIV). In some embodiments, the method of treating a subject suffering from a disease or condition described in this disclosure comprises administering to the subject an effective amount of Compound I Form C, or a composition thereof, in combination a therapeutically effective amount of PD-L1 inhibitor (such as durvalumab, nivolumab, panitumumab, pertuzumab, rituximab, tositumomab, trastuzumab, and 90 Y ibritumomab tiuxetan, for treating a c-Kit or c-Fms related disease as described in this disclosure.

Compound I and II can deplete microglia which can inhibit tau propogation. Exosome inhibitors halt tau propagation. In some embodiments, the method of treating a subject suffering from a disease or condition described in this disclosure comprises administering to the subject an effective amount of Compound I Form C, or a composition thereof, in combination with a therapeutically effective amount of an exosome inhibitor wherein the disease or condition is modulated by Tau propagation. Non-limiting examples of diseases or conditions that are modulated by Tau propagation include Alzheimers disease, Parkinson's disease and dementia.

In some embodiments, the disclosure provides a method of treating a subject suffering from a disease or condition described in this disclosure, said method comprising administering to the subject an effective amount of Compound I Form A, Compound I Form B, Compound I Form C, Compound I Form D or crystalline Compound II or a composition including any one or more compound(s) as described herein, in combination with a c-Kit protein kinase inhibitor or mutant c-Kit protein kinase inhibitor. In another embodiment, the mutant c-Kit protein kinase inhibitor is selected from (2-phenyl-1H-pyrrolo[2,3-b]pyridin-5-yl)-(3-pyridyl)methanol, (2-phenyl-1H-pyrrolo[2,3-b]pyridin-5-yl)-(3-pyridyl)methanone, N-(3-carbamoylphenyl)-2-phenyl-1H-pyrrolo[2,3-b]pyridine-5-carboxamide, 2-phenyl-N-(1H-pyrazol-3-yl)-1H-pyrrolo[2,3-b]pyridine-5-carboxamide, 4-bromo-N-(2-phenyl-1H-pyrrolo[2,3-b]pyridin-5-yl)-1H-pyrazole-5-carboxamide, ethyl 3-[(2-phenyl-1H-pyrrolo[2,3-b]pyridin-5-yl)carbamoylamino]propanoate, 3,4-dimethyl-N-(2-phenyl-1H-pyrrolo[2,3-b]pyridin-5-yl)-1H-pyrazole-5-carboxamide, 4-methyl-3-phenyl-N-(2-phenyl-1H-pyrrolo[2,3-b]pyridin-5-yl)-1H-pyrazole-5-carboxamide, 3-cyclopropyl-N-(2-phenyl-1H-pyrrolo[2,3-b]pyridin-5-yl)-1H-pyrazole-5-carboxamide, 5-fluoro-N-(2-phenyl-1H-pyrrolo[2,3-b]pyridin-5-yl)-1H-indazole-3-carboxamide, N-(2-phenyl-1H-pyrrolo[2,3-b]pyridin-5-yl)pyrimidine-4-carboxamide, 3-fluoro-N-(2-phenyl-1H-pyrrolo[2,3-b]pyridin-5-yl)pyridine-2-carboxamide, 3,5-dimethyl-N-(2-phenyl-1H-pyrrolo[2,3-b]pyridin-5-yl)isoxazole-4-carboxamide, N-(2-phenyl-1H-pyrrolo[2,3-b]pyridin-5-yl)pyridazine-3-carboxamide, N-(2-phenyl-1H-pyrrolo[2,3-b]pyridin-5-yl)-2H-triazole-4-carboxamide, 3-methyl-N-(2-phenyl-1H-pyrrolo[2,3-b]pyridin-5-yl)pyridine-2-carboxamide, 4,5-dimethyl-N-(2-phenyl-1H-pyrrolo[2,3-b]pyridin-5-yl)isoxazole-3-carboxamide or N-(2-phenyl-1H-pyrrolo[2,3-b]pyridin-5-yl)-1H-pyrazole-4-sulfonamide. In another embodiment, Compound I, Form C, is combined with any of the mutant c-Kit mutant inhibitors described in this specification for treating GIST—which includes, without limitation, $1^{st}$ line, $2^{nd}$ line and neoadjuvant GIST.

In some embodiments, the disclosure provides a method of treating a cancer in a subject in need thereof by administering to the subject an effective amount of a compound or a composition including any one or more compound(s) as described herein, in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. X-ray, γ-ray, or electron, proton, neutron, or α particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), oncolytic viral or bacterial therapy, surgery, or bone marrow and stem cell transplantation. In certain embodiments, the disclosure provides a method of treating a cancer in a subject in need thereof by administering to the subject an effective amount of a compound as described herein and applying a radiation treatment as described herein either separately or simultaneously. In one embodiment, the disclosure provides a method for treating a cancer in a subject in need thereof by administering an effective amount of a compound as described herein to the subject followed by a radiation treatment (e.g. X-ray, γ-ray, or electron, proton, neutron, or α particle beam). In another embodiment, the disclosure provides a method for treating a cancer in a subject in need thereof by applying a radiation treatment (e.g. X-ray, γ-ray, or electron, proton, neutron, or α particle beam) to the subject followed by administering an effective amount of a compound as described herein to the subject. In yet another embodiment, the disclosure provides a method for treating a cancer in a subject in need thereof by administering a compound as described herein and a radiation therapy (e.g. X-ray, γ-ray, or electron, proton, neutron, or a particle beam) to the subject simultaneously.

In some embodiments, the disclosure provides a method for treating glioblastoma in a subject. In some embodiments, the method of treating glioblastoma in a subject comprises administering to the subject a therapeutically effective amount of Compound I Form A, Compound I Form B, Compound I Form C, Compound I Form D or crystalline Compound II or a composition comprising of Compound I Form A, Compound I Form B, Compound I Form C, Compound I Form D or crystalline Compound II and a pharmaceutically acceptable excipient. In some embodiments, the method treating glioblastoma in a subject further comprises administering a therapeutically effective amount of a PD-1 inhibitor or a PD-L1 inhibitor to the subject. In some embodiments, the method treating glioblastoma in a subject further comprises administering to the subject a therapeutically effective amount of Compound I Form C, or a composition comprising of Compound I Form C, and a therapeutically effective amount of a PD-1 inhibitor or an PD-L1 inhibitor. In some embodiments, the method treating glioblastoma in a subject further comprises applying an radiation therapy to the subject which may occur before or after administering to the subject a compound or a composition as described herein. In one instance, the treatment has a single dose of 12 Gy ionizing radiation. In another instance, a compound or a composition as described herein is administered to the subject at a dose of about 600 to 1200 mg/day. In some embodiments, such methods further comprise administering to the subject a therapeutically effective amount of temozolomide. In other instances, the method includes applying an ionizing radiation treatment to the subject followed by administering to the subject temozolomide (marketed as Temodar®) and a compound or a composition as described herein. In some embodiments, the method of treating glioblastoma in a subject comprises administering to the subject a therapeutically effective amount of Compound I Form C, or a composition comprising of Compound I Form C, and a pharmaceutically acceptable excipient in combination with (1) applying radiation therapy, and (2) administering a therapeutically effective amount of temozolamide.

In another aspect, the disclosure provides a method for treating a cancer in a subject in need thereof by administering to the subject an effective amount of a compound or a composition including any one or more compound(s) as described herein, in combination with one or more suitable chemotherapeutic agents. The compounds can be administered simultaneously or sequentially. In some embodiments, the cancer is any cancer mediated by a protein kinases selected from c-Fms, c-Kit, Flt3 or combinations thereof and/or macrophages or microglia or a cancer as described herein. In one embodiment, the one or more suitable chemotherapeutic agents is selected from an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, and uramustine; an antibiotic, including, but not limited to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limited to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, raltitrexed, tegafur-uracil, thioguanine, trimethoprim, trimetrexate, and vidarabine; an immunotherapy, an antibody therapy, including, but not limited to, alemtuzumab, bevacizumab, cetuximab, galiximab, gemtuzumab, panitumumab, pertuzumab, rituximab, brentuximab, tositumomab, trastuzumab, 90 Y ibritumomab tiuxetan, ipilimumab, tremelimumab and anti-CTLA-4 antibodies; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, larotaxel, ortataxel, paclitaxel, DHA-paclitaxel, and tesetaxel; a retinoid, including, but not limited to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), enzalutamide, ABT-510, 2-methoxyestradiol, lenalidomide, and thalidomide; a topoisomerase inhibitor, including, but not limited to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not limited to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), vemurafenib, dabrafenib, selumetinib, and vatalanib; a targeted signal transduction inhibitor including, but not limited to bortezomib, geldanamycin, and rapamycin; a biological response modifier, including, but not limited to, imiquimod, interferon-α, and interleukin-2; and other chemotherapeutics, including, but not limited to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. sirolimus, temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. geldanamycin, radicicol, tanespimycin), farnesyltransferase inhibitors (e.g. tipifarnib), and Aromatase inhibitors (anastrozole letrozole exemestane). In some embodiments, the method of treating a cancer involves administering to the subject an effective amount of a composition including any compound as described herein in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-α, interleukin-2, or erlotinib. In another embodiment, the chemotherapeutic agent is a Mek inhibitor. Exemplary Mek inhibitors include, but are not limited to, AS703026, AZD6244 (Selumetinib), AZD8330, BIX 02188, CI-1040 (PD184352), GSK1120212 (JTP-74057), PD0325901, PD318088, binimetinib, PD98059, RDEA119(BAY 869766), TAK-733 and U0126-EtOH. In another embodiment, the chemotherapeutic agent is a tyrosine kinase inhibitor. Exemplary tyrosine kinase inhibitors include, but are not limited to, AEE788, AG-1478 (Tyrphostin AG-1478), AG-490, Apatinib (YN968D1), AV-412, AV-951(Tivozanib), Axitinib, AZD8931, BIBF1120 (Vargatef), BIBW2992 (Afatinib), BMS794833, BMS-599626, Brivanib (BMS-540215), Brivanib alaninate (BMS-582664), Cediranib (AZD2171), Chrysophanic acid (Chrysophanol), Crenolanib (CP-868569), CUDC-101, CYC116, Dovitinib Dilactic acid (TKI258 Dilactic acid), E7080, Erlotinib Hydrochloride (Tarceva, CP-358774, OSI-774, NSC-718781), Foretinib (GSK1363089, XL880), Gefitinib (ZD-1839 or Iressa), Imatinib (Gleevec), Imatinib Mesylate, Ki8751, KRN 633, Lapatinib (Tykerb), Linifanib (ABT-869), Masitinib (Masivet, AB1010), MGCD-265, Motesanib (AMG-706), MP-470, Mubritinib (TAK 165), Neratinib (HKI-272), NVP-BHG712, OSI-420 (Desmethyl Erlotinib, CP-473420), OSI-930, Pazopanib HCl, PD-153035 HCl, PD173074, Pelitinib (EKB-569), PF299804, Ponatinib (AP24534), PP121, RAF265 (CHIR-265), Raf265 derivative, Regorafenib (BAY 73-4506), Sorafenib Tosylate (Nexavar), Sunitinib Malate (Sutent), Telatinib (BAY 57-9352), TSU-68 (SU6668), Vandetanib (Zactima), Vatalanib dihydrochloride (PTK787), WZ3146, WZ4002, WZ8040, XL-184 (Cabozantinib), XL647, EGFR siRNA, FLT4 siRNA, KDR siRNA, Antidiabetic agents such as metformin, PPAR agonists (rosiglitazone, pioglitazone, bezafibrate, ciprofibrate, clofibrate, gemfibrozil, fenofibrate, indeglitazar), and DPP4 inhibitors (sitagliptin, vildagliptin, saxagliptin, dutogliptin, gemigliptin, alogliptin). In another embodiment, the agent is an EGFR inhibitor. Exemplary EGFR inhibitors include, but are not limited to, AEE-788, AP-26113, BIBW-2992 (Tovok), CI-1033, GW-572016, Iressa, LY2874455, RO-5323441, Tarceva (Erlotinib, OSI-774), CUDC-101 and WZ4002.

In some embodiments, the disclosure provides a method of treating a subject suffering from a disease or condition described in this disclosure, said method comprising administering to the subject an effective amount of Compound I Form A, Compound I Form B, Compound I Form C, Compound I Form D or crystalline Compound II or a composition including any one or more compound(s) as described herein, in combination with a therapeutically effective amount of another therapeutic agent, wherein the other therapeutic agent is: i) an alkylating agent (such as adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, or treosulfan); ii) an antibiotic (such as bleomycin, dactinomycin, daunorubicin, doxorubicin, epirubicin, idarubicin, menogaril, mitomycin, mitoxantrone, neocarzinostatin, pentostatin, or plicamycin); iii) an antimetabolite (such as azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, or trimetrexate); iv) an antibody therapy agent selected from alemtuzumab, bevacizumab, cetuximab, galiximab, gemtuzumab, pembrolizumab, nivolumab, durvalumab, panitumumab, pertuzumab, rituximab, tositumomab, trastuzumab, and 90 Y ibritumomab tiuxetan; v) a hormone or hormone antagonist (such as anastrozole, androgens, buserelin, diethylstilbestrol, exemestane, flutamide, fulvestrant, goserelin, idoxifene, letrozole, leuprolide, magestrol, raloxifene, tamoxifen, or toremifene); vi) a taxane (such as DJ-927, docetaxel, TPI 287, paclitaxel or DHA-paclitaxel); vii) a retinoid (such as alitretinoin, bexarotene, fenretinide, isotretinoin, or tretinoin); viii) an alkaloid (such as etoposide, homoharringtonine, teniposide, vinblastine, vincristine, vindesine, or vinorelbine); ix) an antiangiogenic agent (such as AE-941 (GW786034, Neovastat), ABT-510, 2-methoxyestradiol, lenalidomide, or thalidomide); x) a topoisomerase inhibitor (such as amsacrine, edotecarin, exatecan, irinotecan (also active metabolite SN-38 (7-ethyl-10-hydroxy-camptothecin)), rubitecan, topotecan, or 9-aminocamptothecin; xi) a kinase inhibitor [such as PI3K inhibitors (e.g. BEZ235, GDC-0941, XL147, XL765), Cdk4 inhibitors (e.g. PD-332991), Akt inhibitors, a Mek inhibitor (such as AS703026, AZD6244 (Selumetinib), AZD8330, BIX 02188, CI-1040 (PD184352), GSK1120212 (JTP-74057), PD0325901, PD318088, binimetinib, PD98059, RDEA119 (BAY 869766), TAK-733 or U0126-EtOH), an EGFR inhibitor, erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib, trametinib, cobimetinib, cabozantinib, selumetinib, dovitinib, or vatalanib]; xii) a targeted signal transduction inhibitor (such as bortezomib, geldanamycin, or rapamycin); xiii) a biological response modifier (such as imiquimod, interferon-alpha, or interleukin-2); xiv) a chemotherapeutic agent (such as 3-amino-2-carboxyaldehyde thiosemicarbazone, mTOR inhibitors (such as sirolimus, temsirolimus, everolimus, deforolimus), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, or tiazofurin); xv) an Hsp90 inhibitor (e.g. geldanamycin, radicicol, tanespimycin); xvi) a farnesyltransferase inhibitors (e.g. tipifarnib); xvii) an aromatase inhibitor (such as anastrozole, letrozole or exemestane); xviii) an IDO inhibitor; xix) a histone acetyltransferase (HAT) inhibitor; xx) histone deacetylase (HDAC) inhibitor; xxi) a sirtuin (SIRT) inhibitor; xxii) a BET inhibitor (such as BRD2, BRD3, BRD4 and/or BRDT); or xxiii) an antiangiogenic agent, (such as AE-941 (GW786034, Neovastat), enzalutamide, ABT-510, 2-methoxyestradiol, lenalidomide or thalidomide.

Bromodomains (e.g., BET proteins, such as BRD2, BRD3, BRD4, and/or BRDT), and e.g., diseases related to abnormal expression of bromodomains, including cell proliferative disorders, cancers, chronic autoimmune, inflammatory conditions, among others. Non-limiting examples of BET inhibitors include GSK1210151A and GSK525762.

The histone deacetylase inhibitors (HDAC inhibitors) are cytostatic agents that inhibit the proliferation of tumor cells in culture and in vivo by inducing cell cycle arrest, differentiation and/or apoptosis. HDAC inhibitors exert their anti-tumor effects via the induction of expression changes of oncogenes or tumour suppressor, through modulating that the acetylation/deactylation of histones and/or non-histone proteins such as transcription factors. Histone acetylation and deacetylation play important roles in the modulation of chromatin topology and the regulation of gene transcription. Non-limiting examples of HDAC inhibitors include vorinostat, romidepsin, chidamide, panobinostat, belinostat, valproic acid, mocetinostat, abexinostat, entinostat, resminostat, givinostat, and quisinostat. HDAC inhibitors have been used extensively in psychiatry and neurology as mood stabilzers and anti-epileptics. One example of this is valproic acid, marketed as a drug under the trade names Depakene, Depakote, and Divalproex. HDAC inhibitors are also being used as a mitigator for neurodegenerative diseases such as Alzheimer's disease and Huntington's disease.

In some embodiments, the disclosure provides a composition, which includes (i) a compound as described herein and (ii) a chemotherapeutic agent as described herein. The composition can be used for treating a disease or condition mediated by a protein kinases selected from c-Fms, c-Kit, Flt3 or combinations thereof and/or macrophages or microglia. Exemplary diseases or conditions include, but are not limited to, alopecia, baldness, wound healing, androgenetic alopecia (AGA), epilepsy, traumatic brain injury, tauopathies, Erdheim Chester Disease, Langerhans cell histocytosis, hairy cell leukemia, non-small cell lung cancer, cleroderma, anterior eye disease, posterior eye disease, lysosomal storage disease, stem cell ablation and myelopreparation for stem cell transplant, primary progressive multiple sclerosis, complex regional pain syndrome, reflex sympathetic dystrophy, muscular dystrophy, duchenne muscular dystrophy, causalgia, neuro-inflammation, neuroinflammatory disorders, benign forgetfulness, HIV, binswager type dementia, dementia with lewy bodie, prosencephaly, microencephaly, cerebral palsy, congenital hydrocephalus, abdominal dropsy, progressive supranuclear palsy, glaucoma, addiction disorders, dependencies, alcoholism, tremors, Wilson's disease, vascular dementias, multi infarct dementia, fronto temporal dementia, pseudo-dementia, bladder cancer, ureter cancer, urethra cancer, urachus cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer, melanoma, mesothelioma, pancreatic cancer, rectal cancer, renal cancer, squamous cell carcinoma, t cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, angiosarcomas, liposarcomas, ascites, malignant ascites, mesothelioma, salivary gland tumors, mucoepidermoid carcinoma of the salivary gland, acinic cell carcinoma of the salivary gland, gastrointestinal stromal tumors (GIST— which includes, without limitation, $1^{st}$ line, $2^{nd}$ line and neoadjuvant GIST), tumors that cause effusions in potential spaces of the body, pleural effusions, pericardial effusions, peritoneal effusions aka ascites, giant cell tumors (GCT), GCT of bone, pigmented villonodular synovitis (PVNS), tenosynovial giant cell tumor (TGCT), TCGT of tendon sheath (TGCT-TS), other sarcomas, tumor angiogenesis, or paracrine tumor growth. In some embodiments, the compositions can be used to treat tumors that express aberrantly or otherwise Fms, CSF1R, CSF1 or IL-34, or activating mutations or translocations of any of the foregoing; or tumors that express aberrantly or otherwise Kit, SCFR, SCF, or activating mutations or translocations of any of the foregoing; or and tumors that express aberrantly or otherwise Flt3, Flt3 ligand, or activating mutations or translocations of any of the foregoing.

In some embodiments, the disclosure provides a composition including a Raf inhibitor and a compound described herein. In certain embodiments, the disclosure provides a composition including vemurafenib and a compound or a composition as described herein. In certain embodiments, the disclosure provides a composition including dabrafenib and a compound described herein. In certain embodiments, the Raf inhibitor is a B-raf inhibitor as disclosed in U.S. Pat. No. 7,863,288, which is incorporated herein by reference in its entirety.

In some embodiments, the disclosure provides a composition including taxol and a compound described herein.

In some embodiments, the disclosure provides a method for treating mesothelioma in a subject. The method includes administering a composition comprising taxol and a compound as described herein. In some embodiments, the method includes administering to the subject a therapeutically effective amount of Compound I Form A, Compound I Form B, Compound I Form C or Compound I Form D, crystalline Compound II or a composition comprising of Compound I Form A, Compound I Form B, Compound I Form C, Compound I Form D or crystalline Compound II and a pharmaceutically acceptable excipient. In such embodiments, the method further comprises administering to the subject a therapeutically effective amount of taxol. In certain embodiments, the method includes administering to the subject in need thereof an effective amount of a composition comprising taxol and a therapeutically effective amount of Compound I Form A, Compound I Form B, Compound I Form C, Compound I Form D or crystalline Compound II or a composition comprising of Compound I Form A, Compound I Form B, Compound I Form C, Compound I Form D or crystalline Compound II and a pharmaceutically acceptable excipient. In certain embodiments, the method includes administering to the subject in need thereof an effective amount of a composition comprising taxol and a compound or a composition as described herein. In some embodiments, taxol and a compound described herein can be administered simultaneously or separately. In certain embodiments, the disclosure provides a method for treating mesothelioma in a subject. The method includes administering to the subject in need thereof taxol followed by administering to the subject a compound or a composition as described herein. In certain embodiments, the disclosure provides a method for treating a mesothelioma in a subject, wherein the method includes administering to the subject in need thereof a compound or a composition as described herein followed by administering taxol to the subject.

In some embodiments, the disclosure provides a method for treating a melanoma or a metastatic melanoma in a subject. In certain embodiments, the disclosure provides a method for treating melanoma with a KIT mutation in a subject. In certain embodiments, the disclosure provides a method for treating melanoma with a BRAF mutation in a subject. In some embodiments, the method of treating unresectable or metastatic melanoma with a KIT mutation in a subject, or unresectable or metastatic melanoma with a BRAF mutation in a subject, includes administering to the subject a therapeutically effective amount of Compound I Form A, Compound I Form B, Compound I Form C or Compound I Form D, crystalline Compound II or a composition comprising of Compound I Form A, Compound I Form B, Compound I Form C, Compound I Form D or crystalline Compound II and a pharmaceutically acceptable excipient. In some embodiments, the method of treating unresectable or metastatic melanoma with a KIT mutation in a subject includes administering to the subject a therapeutically effective amount of Compound I Form C, or a composition comprising of Compound I Form C and a pharmaceutically acceptable excipient. The method of treating unresectable or metastatic melanoma with a BRAF mutation may further comprises administering to the subject a therapeutically effective amount of vemurafenib. In some embodiments, vemurafenib and a compound described herein can be administered simultaneously or separately. In certain instances, the melanoma is mediated by a mutant B-raf protein kinase. In other instances, the melanoma is mediated by a V600 mutant B-raf. In yet other instances, the melanoma is mediated by a V600A, V600M, V600R, V600E, V600K or V600G B-raf mutant. In other instances, the melanoma is mediated by a V600E mutant B-raf.

In some embodiments, the disclosure provides a method for treating a subject suffering from or at risk of malignant peripheral nerve sheath tumors (MPNST). In some embodiments, the method of treating a subject suffering from or at risk of MPNST includes administering to the subject a therapeutically effective amount of Compound I Form A, Compound I Form B, Compound I Form C, Compound I Form D or crystalline Compound II or a composition comprising of Compound I Form A, Compound I Form B, Compound I Form C, Compound I Form D or crystalline Compound II and a pharmaceutically acceptable excipient. In such embodiments, the method of treating a subject suffering from or at risk of MPNST further comprises administering to the subject a therapeutically effective amount of sirolimus. In certain embodiments, the method of treating a subject suffering from or at risk of MPNST includes administering to the subject in need thereof an effective amount of a composition comprising sirolimus and a compound or a composition as described herein. In certain embodiments, the method of treating a subject suffering from or at risk of MPNST includes administering to the subject in need thereof an effective amount of a composition comprising sirolimus and Compound I Form C, or a composition thereof, as described herein. In some embodiments, sirolimus and a compound or composition described herein can be administered simultaneously or separately.

In some embodiments, the disclosure provides a method for treating a subject suffering from or at risk of breast cancer. In some embodiments, the breast cancer is metatstatic breast cancer. In some embodiments, the method of treating a subject suffering from or at risk of breast cancer includes administering to the subject a therapeutically effective amount of Compound I Form A, Compound I Form B, Compound I Form C, Compound I Form D or crystalline Compound II or a composition comprising of Compound I Form A, Compound I Form B, Compound I Form C, Compound I Form D or crystalline Compound II and a pharmaceutically acceptable excipient. In some embodiments, the method of treating a subject suffering from or at risk of breast cancer further comprises administering to the subject a therapeutically effective amount of eribulin. In some embodiments, the method of treating a subject suffering from or at risk of breast cancer further comprises administering to the subject a therapeutically effective amount of paclitaxel. In certain embodiments, the method of treating a subject suffering from or at risk of breast cancer includes administering to the subject in need thereof an effective amount of a composition comprising eribulin and a compound or a composition as described herein. In certain embodiments, the method of treating a subject suffering from or at risk of breast cancer includes administering to the subject in need thereof an effective amount of a composition comprising paclitaxel and a compound or a composition as described herein. In certain embodiments, the method of treating a subject suffering from or at risk of breast cancer includes administering to the subject in need thereof an effective amount of a composition comprising eribulin and Compound I Form C, or a composition thereof, as described herein. In certain embodiments, the method of treating a subject suffering from or at risk of metastatic breast cancer includes administering to the subject in need thereof an effective amount of a composition comprising eribulin and Compound I Form C, or a composition thereof, as described herein. In certain embodiments, the method of treating a subject suffering from or at risk of metastatic breast cancer includes administering to the subject in need thereof an effective amount of a composition comprising paclitaxel and Compound I Form C, or a composition thereof, as described herein. In some embodiments, eribulin and a compound or composition described herein can be administered simultaneously or separately. In certain embodiments, the method includes administering to the subject in need thereof an effective amount of a composition comprising paclitaxel and a compound or a composition as described herein. In some embodiments, paclitaxel and a compound or composition described herein can be administered simultaneously or separately.

In some embodiments, the disclosure provides a method for treating a subject suffering from or at risk of ovarian cancer. In some embodiments, the method of treating a subject suffering from or at risk of ovarian cancer comprises administering to the subject a therapeutically effective amount of Compound I Form A, Compound I Form B, Compound I Form C, Compound I Form D or crystalline Compound II or a composition comprising of Compound I Form A, Compound I Form B, Compound I Form C, Compound I Form D or crystalline Compound II and a pharmaceutically acceptable excipient. In some embodiments, the method of treating a subject suffering from or at risk of ovarian cancer further comprises administering to the subject a therapeutically effective amount of paclitaxel. In certain embodiments, the method of treating a subject suffering from or at risk of ovarian cancer includes administering to the subject in need thereof an effective amount of a composition comprising paclitaxel and a compound or a composition as described herein. In certain embodiments, the method of treating a subject suffering from or at risk of ovarian cancer includes administering to the subject in need thereof an effective amount of a composition comprising paclitaxel and Compound I Form C, or a composition thereof, as described herein. In some embodiments, paclitaxel and a compound or composition as described herein can be administered to the subject in need thereof simultaneously or separately. In some embodiments, paclitaxel and Compound I Form C can be administered to the subject in need thereof simultaneously or separately.

In some embodiments, the disclosure provides a method for treating a subject suffering from or at risk solid tumors, comprising administering to the subject a therapeutically effective amount of Compound I Form A, Compound I Form B, Compound I Form C, Compound I Form D or crystalline Compound II or a composition comprising of Compound I Form A, Compound I Form B, Compound I Form C, Compound I Form D or crystalline Compound II and a pharmaceutically acceptable excipient. In some embodiments, the method of treating a subject suffering from or at risk of melanoma further comprises administering to the subject a therapeutically effective amount of pembrolizumab. In certain embodiments, the method of treating a subject suffering from or at risk of melanoma includes administering to the subject in need thereof an effective amount of a composition comprising pembrolizumab and a compound or a composition as described herein. In certain embodiments, the method of treating a subject suffering from or at risk of melanoma includes administering to the subject in need thereof an effective amount of a composition comprising pembrolizumab and Compound I Form C, or a composition thereof, as described herein. In some embodiments, pembrolizumab and a compound or composition described herein can be administered simultaneously or separately.

Kinase Activity Assays

A number of different assays for kinase activity can be utilized for assaying for active modulators and/or determining specificity of a modulator for a particular kinase or group of kinases, such as those described in U.S. Pat. Pub. No. 2014/0037617, which is hereby incorporated by reference in its entirety. One of ordinary skill in the art can readily identify other assays that can be utilized and can modify an assay for a particular application. For example, numerous papers concerning kinases describe assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

EXAMPLES

A. Experimental Methods
Approximate Solubility—Solvent Addition Method

A weighed sample was treated with aliquots of the test solvent at room temperature. The mixture was sonicated between additions to facilitate dissolution. Complete dissolution of the test material was determined by visual inspection. Solubility was estimated based on the total solvent used to provide complete dissolution. The actual solubility may be greater than the value calculated because of the use of solvent aliquots that were too large or due to a slow rate of dissolution. If complete dissolution was achieved as a result of only one aliquot addition, the solubility is expressed as "greater than."

Crystallization Screen

Both thermodynamic and kinetic crystallization techniques were employed. These techniques are described in more detail below. Once solid samples were harvested from crystallization attempts, they were either examined under a microscope for birefringence and morphology or observed with the naked eye. Solid samples were then analyzed by XRFD, and the crystalline patterns compared to each other to identify new crystalline forms.

Ambient Solution (AS)

Solutions were prepared in various solvents at ambient temperature. The solution was filtered through a 0.2-μm filter. An antisolvent was added until turbidity was achieved or until a maximum volume was obtained. Solutions were capped and then allowed to sit at ambient.

Crash Cool (CC)

Saturated solutions were prepared in various solvents at elevated temperature. The solutions were filtered through a pre-warmed 0.2-μm filter and then placed directly into a freezer.

Fast Evaporation (FE)

Solutions were prepared in various solvents and sonicated between aliquot additions to assist in dissolution. Once a mixture reached complete dissolution, as judged by visual observation, the solution was filtered through a 0.2-μm filter. The filtered solution was allowed to evaporate at ambient in an uncapped vial.

Grinding (Mixer Mill)

A solid sample was placed into a ceramic grinding jar with a grinding ball. A small amount of solvent may have also been added. The sample was then ground at 30 Hz on a Retesh type MM220 mixer mill for 20 minutes. The solids were isolated and analyzed.

Rotary Evaporation (RE)

Solutions prepared in various solvents were placed on the rotary evaporator and removed when dry. Some samples were further dried in a vacuum oven at elevated temperature.

Slow Cool (SC)

Saturated solutions were prepared in various solvents at elevated temperatures and filtered through a 0.2-μm filter into a vial while still warm. The vial was sealed and allowed to cool slowly to room temperature (some samples started directly from ambient temperature). The presence or absence of solids was noted. If there were no solids present, or if the amount of solids was judged too small for XRPD analysis, the vial was placed in a refrigerator. Again, the presence or absence of solids was noted and if there were none, the vial was placed in a freezer. Solids that formed were isolated by filtration and allowed to dry prior to analysis.

Slow Evaporation (SE)

Solutions were prepared in various solvents and sonicated between aliquot additions to assist in dissolution. Once a mixture reached complete dissolution, as judged by visual observation, the solution was filtered through a 0.2 μm filter. The solution was allowed to evaporate at ambient in a vial covered with aluminum foil perforated with pinholes unless otherwise noted.

Slurry Experiments

Solutions were prepared by adding enough solids to a given solvent so that excess solids were present. The mixture was then agitated in a sealed vial at either ambient or a set temperature.

Solid Vapor Stress (VS)

A solid sample was placed into a small glass vial, and then placed into a large capped vial containing solvent. The vials were left vertically and undisturbed at ambient.

Stress Experiments

Solids were stressed under different temperature and/or relative humidity (RH) environments for a measured time period. Specific RH values were achieved by placing the sample inside sealed chambers containing saturated salt solutions. The salt solutions were selected and prepared following an ASTM standard procedure.

B. Instrumental Techniques

Differential Scanning Calorimetry (DSC)

The data acquisition parameters are displayed on each thermogram in the Data section of this report. Each sample was placed into an aluminum DSC pan, and the weight accurately recorded. Indium metal was used as the calibration standard.

Dynamic Vapor Sorption/Desorption (DVS)

Moisture sorption/desorption data were collected on a VTI SGA-100 Vapor Sorption Analyzer under a nitrogen purge. Equilibrium criteria and the relative humidity (RH) range used for analysis are displayed on each spreadsheet record in the Data section of this report. Data were not corrected for the initial moisture content of the samples. Sodium chloride and polyvinypyrrolidine were used as calibration standards.

Hot Stage Microscopy

Hot stage microscopy was performed using a Linkam hot stage (model FTIR 600) mounted on a Leica DM LP microscope equipped with a SPOT Insight™ color digital camera. Temperature calibrations were performed using USP melting point standards. Samples were placed on a cover glass, and a second cover glass was placed on top of the sample. As the stage was heated, each sample was visually observed using a 20× objective with crossed polarizers and a first order red compensator. Images were captured using SPOT software (v. 4.5.9).

Coulometric Karl-Fischer Analysis (KF)

Coulometric Karl Fischer (KF) analysis for water determination was performed using a Mettler Toledo DL39 Karl Fischer titrator. The sample was placed in the KF titration vessel containing of Hydranal—Coulomat AD and mixed for 60 seconds to ensure dissolution. The sample was then titrated by means of a generator electrode which produces iodine by electrochemical oxidation: $2\ I^- \Rightarrow I_2 + 2e$. The sample size was optimized by performing a scoping experiment. Two replicates were obtained to ensure reproducibility. The value reported is the average of the two replicates.

Infrared Spectroscopy (IR)

IR spectra were acquired on a Magna-IR 860® Fourier transform infrared (FT-IR) spectrophotometer (Thermo Nicolet) equipped with an Ever-Glo mid/far IR source, an extended range potassium bromide (KBr) beamsplitter, and a deuterated triglycine sulfate (DTGS) detector. An attenuated total reflectance (ATR) accessory (Thunderdome™, Thermo Spectra-Tech), with a germanium (Ge) crystal was used for data acquisition. The data acquisition parameters for each spectrum are displayed above the image in the Data section of this report. A background data set was acquired with a clean Ge crystal. A Log 1/R (R=reflectance) spectrum was acquired by taking a ratio of these two data sets against each other. Wavelength verification was performed using NIST SRM 1921b (polystyrene).

Nuclear Magnetic Resonance (NMR)

The solution phase $^1$H NMR spectra were collected at Spectra Data Services, Inc. The spectra acquisition parameters are printed on each spectrum in the Data section of this report. Spectra were referenced to internal tetramethylsilane at 0.0 ppm.

Raman Spectroscopy

Raman spectra were acquired on a Raman accessory module interfaced to a Magna-IR 860® Fourier transform infrared (FT-IR) spectrophotometer (Thermo Nicolet) equipped with an indium gallium arsenide (InGaAs) detector. Wavelength verification was performed using sulfur and cyclohexane. Each sample was prepared for analysis by pressing into a pellet and placing it into a pellet holder. The data acquisition parameters for each spectrum are displayed above the image in the Data section of this report.

Thermogravimetry (TG)

The data acquisition parameters are displayed on each thermogram in the Data section of this report. The sample was placed in an aluminum sample pan and inserted into the TG furnace. Nickel and Alumel™ were used as the calibration standards.

X-Ray Powder Diffraction (XRPD)

XRPD patterns of some forms of Compound I were collected with a PANalytical X'Pert PRO MPD diffractometer using the following experimental setting: 45 kV, 40 mA, Kα1=1.5406 Å, scan range 1.01-39.98° 2θ, step size 0.017° 2θ, collection time: 1936 s. XRPD patterns of some other forms of Compound I were collected with a Intel XRG-3000 Diffractometer using the following experimental setting: 40 kV, 30 mA, step size 0.03° 2θ, collection time: 300 s.

Figure 6:
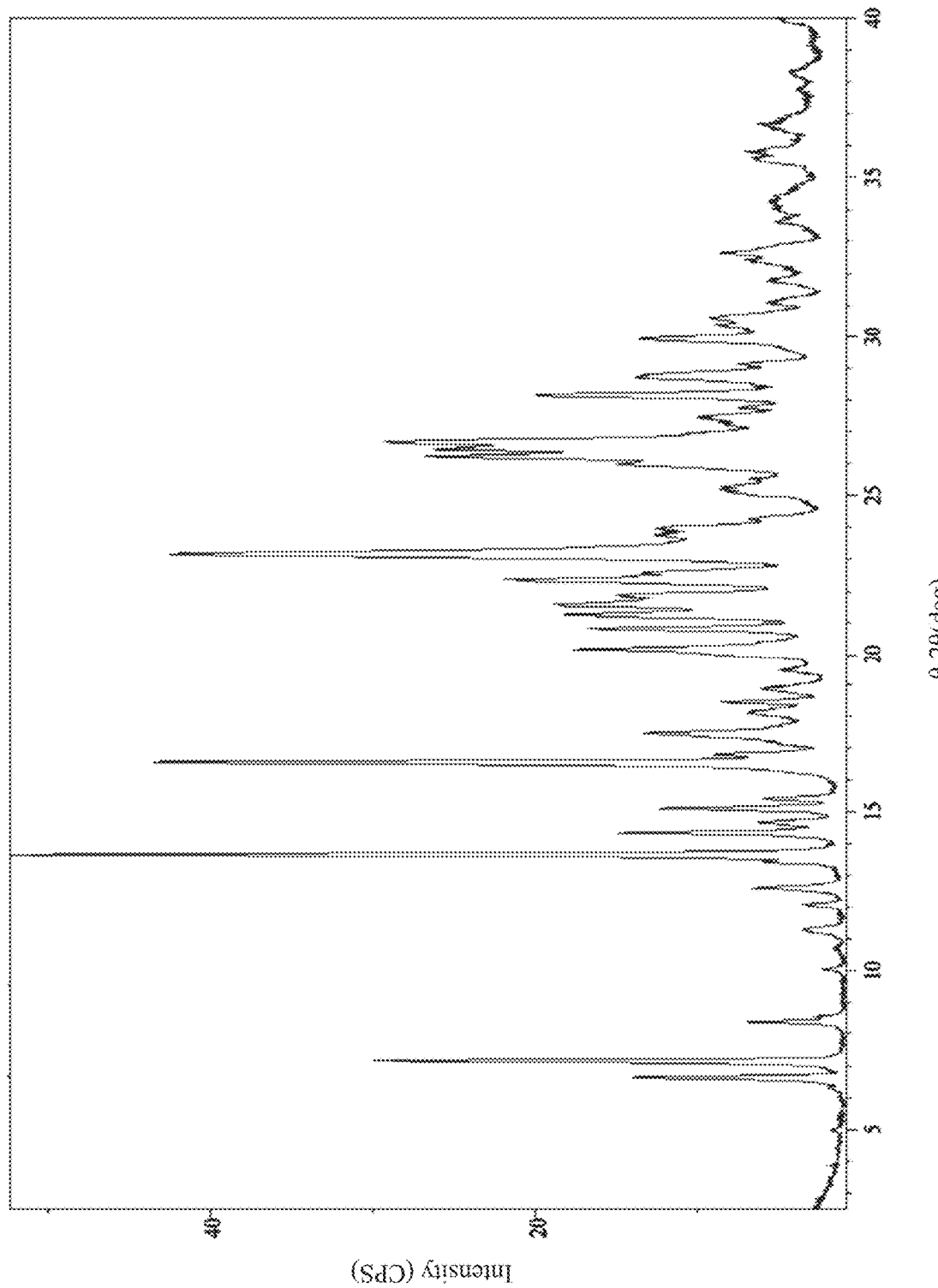
FIG. 6 is an X-ray powder diffraction pattern of Compound I Form B.
Figure 10:
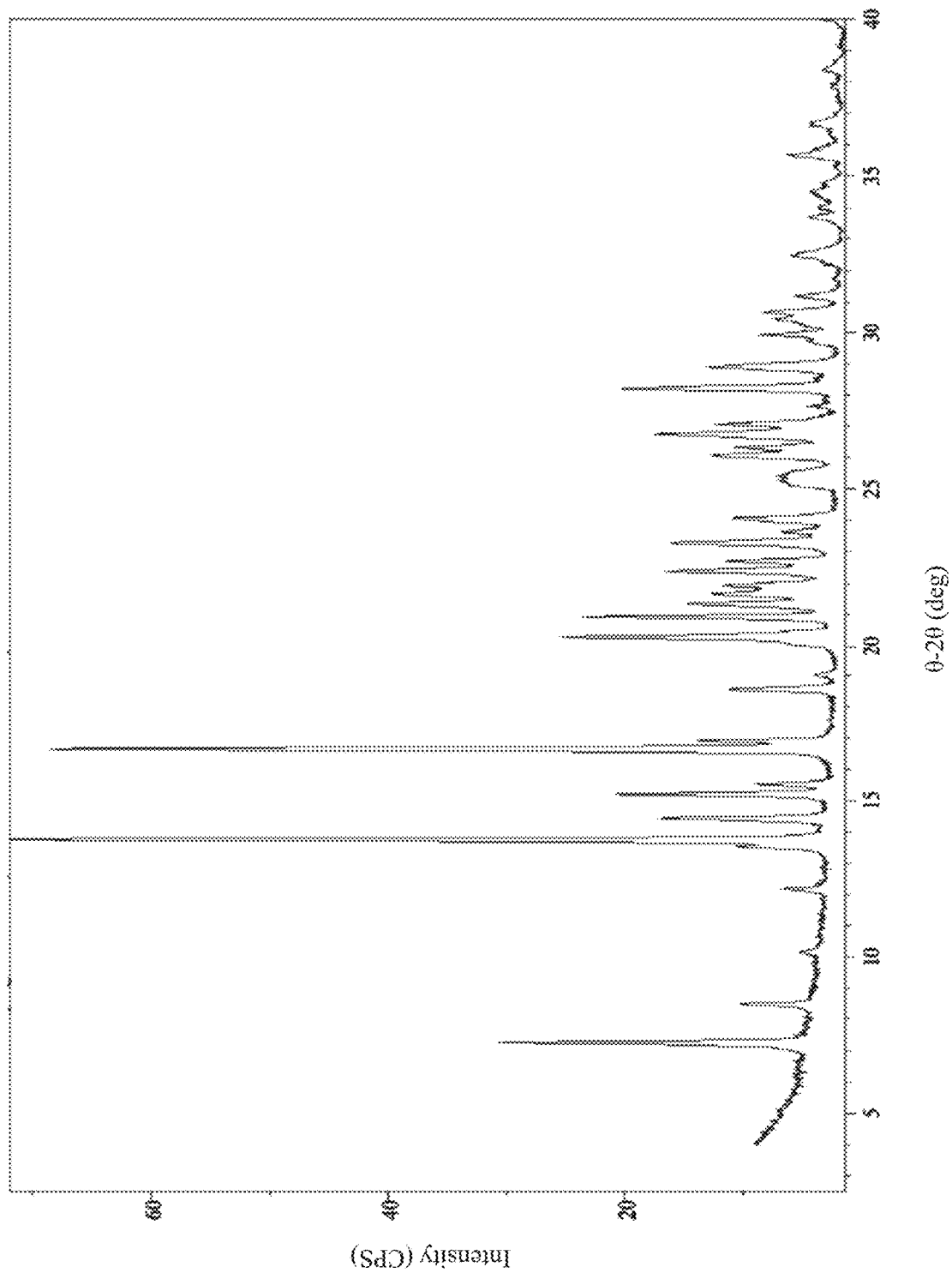
FIG. 10 is an X-ray powder diffraction pattern of Compound I Form C.
Figure 17:
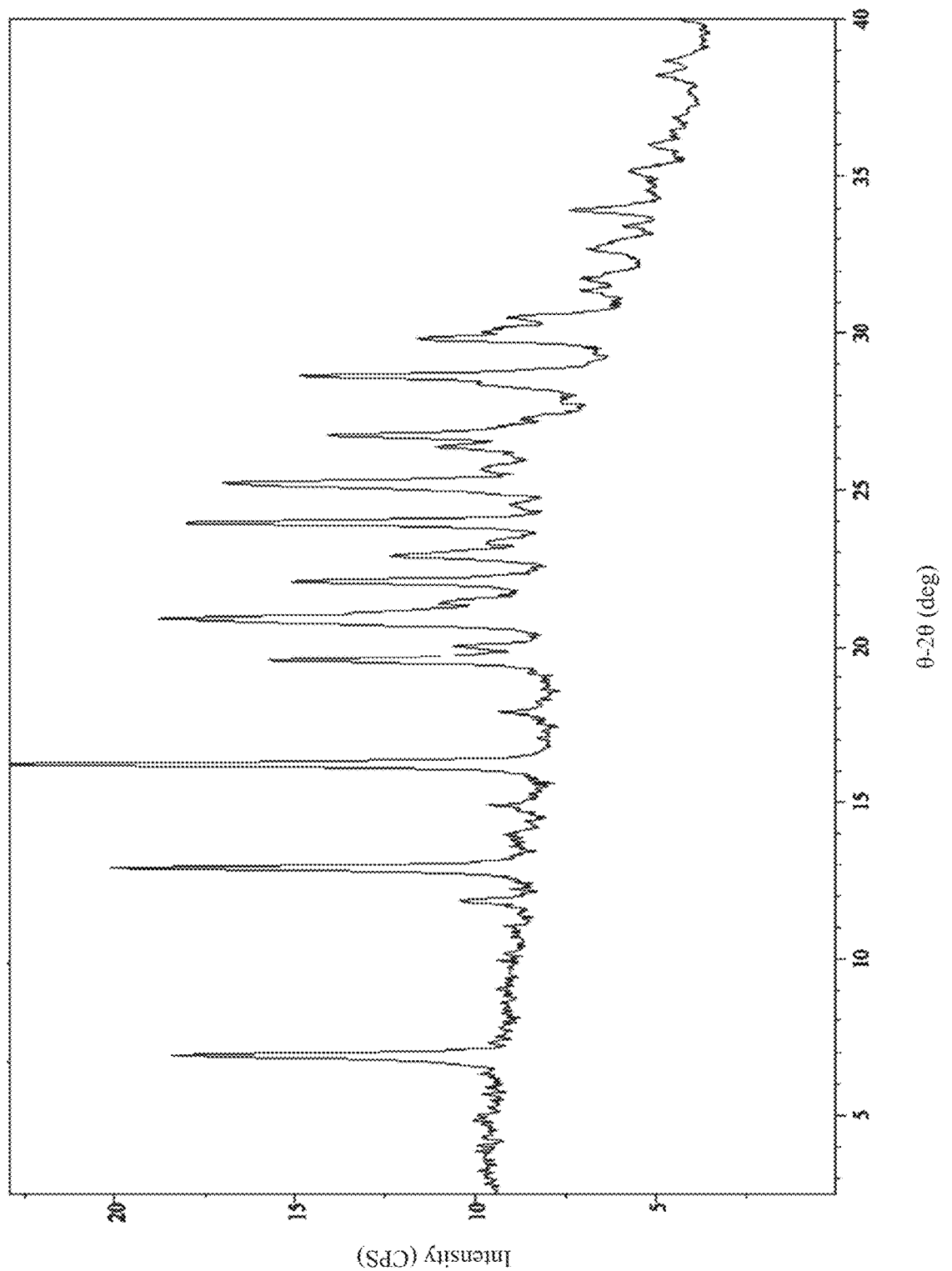
FIG. 17 is X-ray powder diffraction pattern of Compound I Form D.

XRPD data shown in FIGS. 1, 6 and 10 was collected using PANalytical X'Pert Pro Diffractometer and the XRPD data shown in FIG. 17 was collected using Intel XRG-3000 Diffractometer.

The data presented contain X-ray diffraction patterns with tables with peak lists. The range of data collected is instrument dependent. Under most circumstances, peaks within the range of up to about 30° 2θ were selected. Rounding algorithms were used to round each peak to the nearest 0.1° or 0.01° 2θ, depending upon the instrument used to collect the data and/or the inherent peak resolution. The location of the peaks along the x-axis (° 2θ) in both the figures and the tables were determined using proprietary software (TRIADS, version 2) and rounded to one or two significant figures after the decimal point based upon the above criteria. Peak position variabilities are given to within ±0.2° 2θ based upon recommendations outlined in the USP discussion of variability in X-ray powder diffraction (United States Pharmacopeia, USP 37, NF 32, through S2 <941>, 503, Dec. 1, 2014). The accuracy and precision associated with any particular measurement reported herein has not been determined. Moreover, third party measurements on independently prepared samples on different instruments may lead to variability which is greater than ±0.2° 2θ. For d-space listings, the wavelength used to calculate d-spacings was 1.5405929 Å, the Cu-K$_{α1}$ wavelength (*Phys. Rev.* A56(6) 4554-4568 (1997). Variability associated with d-spacing estimates was calculated from the USP recommendation, at each d-spacing, and provided in the respective data tables.

Per USP guidelines, variable hydrates and solvates may display peak variances greater than 0.2° 2θ and therefore peak variances of 0.2° 2θ are not applicable to these materials.

If multiple diffraction patterns are available, then assessments of particle statistics (PS) and/or preferred orientation (PO) are possible. Reproducibility among XRPD patterns from multiple samples analyzed on a single diffractometer indicates that the particle statistics are adequate. Consistency of relative intensity among XRPD patterns from multiple diffractometers indicates good orientation statistics. Alternatively, the observed XRPD pattern may be compared with a calculated XRPD pattern based upon a single crystal structure, if available. Two-dimensional scattering patterns using area detectors can also be used to evaluate PS/PO. If the effects of both PS and PO are determined to be negligible, then the XRPD pattern is representative of the powder average intensity for the sample and prominent peaks may be identified as "Representative Peaks". In general, the more data collected to determine Representative Peaks, the more confident one can be of the classification of those peaks.

"Characteristic peaks", to the extent they exist, are a subset of Representative Peaks and are used to differentiate one crystalline polymorph from another crystalline polymorph (polymorphs being crystalline forms having the same chemical composition). Characteristic peaks are determined by evaluating which representative peaks, if any, are present in one crystalline polymorph of a compound against all other known crystalline polymorphs of that compound to within ±0.2° 2θ. Not all crystalline polymorphs of a compound necessarily have at least one characteristic peak.

Intel XRG-3000 Diffractometer

XRPD patterns were collected using an Inel XRG-3000 diffractometer equipped with a curved position sensitive detector with a 2θ range of 120°. Prior to the analysis, a silicon standard (NIST SRM 640c) was analyzed to verify the Si 111 peak position. Samples were prepared for analysis by packing them into thin-walled glass capillaries. Each capillary was mounted onto a goniometer head and rotated during data acquisition.

PANalytical X'Pert Pro Diffractometer

The specimen was analyzed using Cu radiation produced using an Optix long fine-focus source. An elliptically graded multilayer mirror was used to focus the Cu Kα X-rays of the source through the specimen and onto the detector. The specimen was sandwiched between 3-micron thick films, analyzed in transmission geometry, and rotated to optimize orientation statistics. A beam-stop was used to minimize the background generated by air scattering. Soller slits were used for the incident and diffracted beams to minimize axial divergence. Diffraction patterns were collected using a scanning position-sensitive detector (X'Celerator) located 240 mm from the specimen. Prior to the analysis a silicon specimen (NIST SRM 640c) was analyzed to verify the position of the silicon 111 peak.

Light Microscopy

Light microscopy was performed using a Leica DM LP microscope equipped with Spot Insight color camera (model 3.2.0). A 10×, 20×, or 40× objective was used with cross polarizers and a first order red compensator in place to view samples. Samples were placed on a glass slide, then a cover glass was then placed over each sample. Samples were analyzed as a dry mount and suspended in mineral oil. Images were acquired at ambient temperature using Spot software (v.4.5.9 for Windows). Micron bars were inserted onto the images as a reference for particle size.

Example 1: Preparation of [5-(5-chloro-1H-pyrrolo[2,3-b]pyridin-3-ylmethyl)-pyridin-2-yl]-(6-trifluoromethyl-pyridin-3-ylmethyl)-amine HCl Salt (Compound I Form A)

Compound I Form A was obtained via recrystallization of Compound I from methanol and water. Compound I (100 gm) was charged into a flask and 800 mL methanol was added. The reaction mixtures was heated to 65° C. and 600 mL water was added as a steady steam maintaining the temperature at 60° C. The solution was filtered while hot (60° C.) to remove the insolubles. Heating was discontinued and the filtrate was cooled to room temperature stirring for at least four hours. White solid precipitated out that was filtered, washed with water (2×200 mL) and dried under high vacuum at 60° C. to provide 78 gm of Compound I Form A with a purity of 99.8% by HPLC.

Compound I Form A was also obtained from the desolvation of Form D under mild heating conditions.

The XRPD pattern for Compound I Form A is shown in FIG. 1. The differential scanning calorimetry (DSC) curve of Form A is shown in FIG. 2. The thermogravimetric analysis (TGA) of Form A comprising a thermogram is shown in FIG. 3. The dynamic vapor sorption (DVS) of Form A is shown in FIG. 4. The Raman spectrum of Form A is shown in FIG. 5. The nuclear magnetic resonance spectrum ($^1$H NMR) of Form A is shown in shown in FIG. 14. The IR spectrum of form A is shown in FIG. 15.

Example 2: Preparation of [5-(5-chloro-1H-pyrrolo[2,3-b]pyridin-3-ylmethyl)-pyridin-2-yl]-(6-trifluoromethyl-pyridin-3-ylmethyl)-amine HCl Salt (Compound I Form B)

Compound I Form B was obtained by converting the Compound I free base to hydrochloride salt.

The XRPD pattern for Compound I Form B is shown in FIG. 6. The differential scanning calorimetry (DSC) curve of Form B is shown in FIG. 7. The thermogravimetric analysis (TGA) of Form B comprising a thermogram is shown in FIG. 8. The Raman spectrum of Form B is shown in FIG. 9. The nuclear magnetic resonance spectrum ($^1$H NMR) of Form B is shown in shown in FIG. 14. The IR spectrum of form B is shown in FIG. 16.

Example 3: Preparation of [5-(5-chloro-1H-pyrrolo[2,3-b]pyridin-3-ylmethyl)-pyridin-2-yl]-(6-trifluoromethyl-pyridin-3-ylmethyl)-amine HCl Salt (Compound I Forms C and D)

Compound I Forms C and D were obtained via recrystallization of Compound I Form A from a variety of solvents under a variety of conditions. The following table summarizes the crystallization experiments of Compound I Form A.

TABLE 1

Crystallization Experiments of Compound I Form A

| Solvent (v/v) | Conditions[1] | Description[2] | XRPD Result[3] |
| --- | --- | --- | --- |
| Acetone | VS | White solid | C |
|  | Slurry (55° C./1 d) | White solid | Amorph + pks |
| 1,4-Dioxane | VS | White solid | C |
| EtOH | SE | White solid, B, UM | C |
|  | VS | White solid | C |
|  | CC (60° C. to fzr) | White solid | C |
|  | SC (60° C. to RT) | White solid | C |
|  | Slurry (RT/21 d) | White solid | C |
| MeOH | SE | White solid, no B/E, UM | A |
|  | VS | White solid | D |
|  | Slurry (RT/21 d) | White solid | C |
| Acetone/MeOH (88:12) | SC (60° C. to rfg) | White solid, B, needles | D |
| IPA/water (88:12) | FE | White solid | C |
|  | SC (60° C. to rfg) | White solid, B, needles | C |
| MeOH/water (10:90) | Slurry (RT/21 d) | White solid | Amorph + pks |
| MeOH/water (57:43) | Slurry (60° C./1 d) | White solid | Disordered |
| Water | VS | White solid | A + C |

[1]CC = Crash Cool, SC = Slow Cool, SE = Slow evaporation, FE = Fast evaporation, VS = Vapor stress, d = days, RT = Room temperature, fzr = freezer, rfg = refrigerator, times and temperatures are approximate.
[2]B = birefringent, B/E = birefringence with extinction, UM = unknown morphology.
[3]Amorph = X-ray amorphous.

TABLE 2

| Ambient Solution Crystallization of Compound I Form A | | | |
|---|---|---|---|
| Solvent | Antisolvent | Description | XRPD Result |
| EtOH | EtOAc | White solid | A + C |
| EtOH | EtOAc[1] | White solid, not birefringent, needles. | C |
| MeOH | EtOAc | White solid | C |

[1]Precooled in freezer for about 20 minutes.

TABLE 3

| Solvent Grinding of Compound I Form A | | |
|---|---|---|
| Solvent | Description | XRPD Result |
| EtOH | White solid | C |
| MeOH | White solid | A + C + D |
| IPA | White solid | C |
| Water | White solid | A + C |

The XRPD pattern for Compound I Form C is shown in FIG. 10. The differential scanning calorimetry (DSC) curve of Form C is shown in FIG. 11. The thermogravimetric analysis (TGA) of Form C comprising a thermogram is shown in FIG. 12. The dynamic vapor sorption (DVS) of Form C is shown in FIG. 13. The nuclear magnetic resonance spectrum ($^1$H NMR) of Form C is shown in shown in FIG. 14.

The XRPD pattern for Compound I Form D is shown in FIG. 17. The thermogravimetric analysis (TGA) of Form B comprising a thermogram is shown in FIG. 23.

Example 4: Preparation of Crystalline [5-(5-chloro-1H-pyrrolo[2,3-b]pyridin-3-ylmethyl)-pyridin-2-yl]-(6-trifluoromethyl-pyridin-3-ylmethyl)-amine (Free Base of Compound I)

Compound II was prepared as disclosed above in Scheme I.

What is claimed is:

1. A process of preparing a capsule comprising a crystalline form of Compound I:

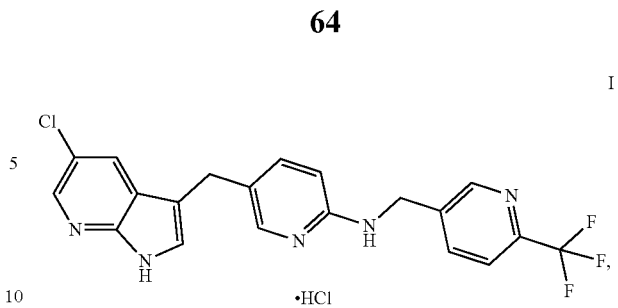

which is Compound I Form C, characterized by an X-ray powder diffractogram comprising peaks (±0.2°) at 7.3, 23.3 and 28.2° 2θ as determined on a diffractometer using Cu-Kα radiation, comprising combining Compound I Form C with a pharmaceutically acceptable carrier or excipient.

2. The process of claim 1, wherein the capsule comprises at least 35% w/w of Compound I Form C.

3. A process of preparing a tablet comprising a crystalline form of Compound I:

I which is Compound I Form C, characterized by an X-ray powder diffractogram comprising peaks (±0.2°) at 7.3, 23.3 and 28.2° 2θ as determined on a diffractometer using Cu-Kα radiation, comprising combining Compound I Form C with a pharmaceutically acceptable carrier or excipient.

4. The process of claim 1, wherein the tablet comprises at least 35% w/w of Compound I Form C.

* * * * *